US008349858B2

(12) United States Patent
Tulshian et al.

(10) Patent No.: US 8,349,858 B2
(45) Date of Patent: Jan. 8, 2013

(54) POLYCYCLIC GUANINE DERIVATIVES AND USE THEREOF

(75) Inventors: Deen Tulshian, Lebanon, NJ (US);
William B. Geiss, Athens, NY (US);
Gregory S. Martin, Guilderland, NY (US); Van-Duc Le, Selkirk, NY (US);
James C. Haber, Jr., Scotia, NY (US);
Julius J. Matasi, Monmouth Junction, NJ (US); Michael F. Czarniecki, Watchung, NJ (US); Stephanie Nicole Cooke, Plainsboro, NJ (US)

(73) Assignee: Merck Sharp & Dohme, Rahway, NJ (US)

( * ) Notice: Subject to any disclaimer, the term of this patent is extended or adjusted under 35 U.S.C. 154(b) by 393 days.

(21) Appl. No.: 12/663,727

(22) PCT Filed: Jun. 18, 2008

(86) PCT No.: PCT/US2008/007592
§ 371 (c)(1), (2), (4) Date: Jun. 11, 2010

(87) PCT Pub. No.: WO2009/002423
PCT Pub. Date: Dec. 31, 2008

(65) Prior Publication Data
US 2011/0065738 A1 Mar. 17, 2011

Related U.S. Application Data

(60) Provisional application No. 60/945,452, filed on Jun. 21, 2007.

(51) Int. Cl.
*A01N 43/54* (2006.01)
*A61K 31/505* (2006.01)
*C07D 239/00* (2006.01)
*C07D 487/00* (2006.01)

(52) U.S. Cl. ........................................ 514/267; 544/251

(58) Field of Classification Search .................. 514/267; 544/251
See application file for complete search history.

(56) References Cited

U.S. PATENT DOCUMENTS

| | | | |
|---|---|---|---|
| 5,393,755 | A | 2/1995 | Neustadt et al. |
| 5,856,129 | A | 1/1999 | Hillman et al. |
| 5,985,603 | A | 11/1999 | Valera et al. |
| 6,194,162 | B1 | 2/2001 | Valera et al. |
| 2002/0168625 | A1 | 11/2002 | Weaver |
| 2002/0182646 | A1 | 12/2002 | Ke et al. |
| 2004/0253650 | A1 | 12/2004 | Denlinger et al. |
| 2005/0054013 | A1 | 3/2005 | Ke et al. |
| 2005/0123925 | A1 | 6/2005 | Ashkenazi et al. |
| 2005/0238650 | A1 | 10/2005 | Crowley et al. |
| 2007/0054361 | A1 | 3/2007 | Ashkenazi et al. |
| 2007/0072903 | A1 | 3/2007 | Elliott et al. |
| 2007/0172815 | A1 | 7/2007 | Weaver |
| 2007/0249666 | A1 | 10/2007 | Bratcher et al. |

FOREIGN PATENT DOCUMENTS

| | | |
|---|---|---|
| EP | 0 119 372 | 9/1984 |
| WO | WO 99/55901 | 11/1999 |
| WO | WO 2006/130676 | 12/2006 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
West, Anthony R., Solid State Chemistry and Its Applications, Wiley, New York, 1988, 358.*
Hide, Mechanism of Production and Release of Tumor Necrosis Factor Implicated in Inflammatory Diseases, Nihon Yakurigaku Zasshi. Folia Pharmacologica Japonica, vol. 121, No. 3, pp. 163-73 (Mar. 2003).*
Boyle, et al., Optimization of Purine Based PDE1/PDE5 Inhibitors to a Potent and Selective PDE5 Inhibitor for the Treatment of Male ED, Bioorganic & Medicinal Chemistry Letters, 15(9), 2365-2369 (2005).*
Abramson, Steven B., et al. 2006. Biologics in development for rheumatoid arthritis: relevance to osteoarthritis. *Advanced Drug Delivery Reviews*, vol. 58, pp. 212-225.
Cheewatrakoolpong, Boonlert, et al. 2005. Identification and characterization of splice variants of the human $P2X_7$ ATP channel. *Biochemical and Biophysical Research Communications*. vol. 332, pp. 17-27.
Chen, L., et al. 2006. Regulation of immune response by P2X7 receptor. *Critical Reviews in Immunology*, vol. 26, pp. 499-513.
Chessell, Iain P., et al. 2005. Disruption of the P2X7 purinoceptor gene abolishes chronic inflammatory and neuropathic pain. *Pain*, vol. 114, pp. 386-396.
Combe, Rachel, et al. 2004. The monosodium iodoacetate model of osteoarthritis: a model of chronic nociceptive pain in rats? *Neuroscience Letters*, vol. 370, pp. 236-240.
Conlon, David A. et al., 2006. Process Development and Large-Scale Synthesis of a PDE4 Inhibitor, *Organic Process Research & Development*, vol. 10, pp. 36-45.
Fernihough, Janet, et al. 2004. Pain related behaviour in two models of osteoarthritis in the rat knee. *Pain*, vol. 112, pp. 83-93. Ferrari, Davide, et al. 2006. The $P2X_7$ Receptor: A Key Player in IL-1 Processing and Release. *The Journal of Immunology*, vol. 176, pp. 3877-3883.
Firestein, Gary S. 2003. Evolving concepts of rheumatoid arthritis. *Nature*, vol. 423, pp. 356-361.
Fonfria, E., et al. 2005. Species- and temperature-dependent effects of a novel P2X7 receptor antagonist on recombinant and native P2X7 receptors. *Abstract—Society for Neuroscience*: Program No. 958.1.
Guerra, Alma N., et al. 2003. Purinergic receptor regulation of LPS-induced signaling and pathophysiology. *Journal of Endotoxin Research*, vol. 9, No. 4, pp. 256-263.
Honore, Prisca et al. 2006. A-740003 [N-(1-{[(cyanoimino)(5-quinolinylamino) methyl]amino)- 2,2-dimethylpropyl)-2-(3,4-dimethoxyphenypacetamide], a novel and selective $P2X_7$ receptor antagonist, dose-dependently reduces neuropathic pain in the rat. *Journal of Pharmacology Experimental Therapeutics*, vol. 319, No. 3, pp. 1376-1385.

(Continued)

*Primary Examiner* — Erich A Leeser
(74) *Attorney, Agent, or Firm* — Sylvia A. Ayler; Gerard M. Devlin

(57) ABSTRACT

The present invention relates to Polycyclic Guanine Derivatives, compositions comprising the Polycyclic Guanine Derivatives and methods of using the Polycyclic Guanine Derivatives to treat pain or an inflammatory disease.

34 Claims, No Drawings

OTHER PUBLICATIONS

Inoue, Atsuko et al. 1999. Interleukin-1β induces substance P release from primary afferent neurons through the cyclooxygenase-2 system. *The Journal of Neurochemistry*, vol. 73, pp. 2206-2213.

Ivanavicius, Stefan P., et al. 2007. Structural pathology in a rodent model of osteoarthritis is associated with neuropathic pain: increased expression of ATF-3 and pharmacological characterisation. *Pain*, vol. 128, pp. 272-282.

Kobayashi, Kiyoshi et al. 2003. Sodium iodoacetate-induced experimental osteoarthritis and associated pain model in rats. *Journal of Veterinary Medical Science*. vol. 65, No. 11, pp. 1195-1199.

Labasi, Jeffrey. M., et al. 2002. Absence of the $P2X_7$ receptor alters leukocyte function and attenuates an inflammatory response. *The Journal of Immunology*, vol. 168, pp. 6436-6445.

Lappin, S. C., et al. 2005. Reversal of mechanical hyperalgesia in a rat model of inflammatory pain by a potent and selective P2X7 antagonist.*Abstract—Society for Neuroscience*: Program No. 958.2.

Lister, Martin F., et al. 2007. The role of the purinergic $P2X_7$ receptor in inflammation. *Journal of inflammation*, vol. 4, No. 5, pp. 1-14.

Wüller-Ladner, et al. 2005. Mechanisms of Disease: the molecular and cellular basis of joint destruction in rheumatoid arthritis. *Nature Clinical Practice Rheumatology*. vol. 1, No. 2, pp. 102-110.

Pelegrin, Pablo et al. 2007. Pannexin-1 couples to maitotoxin- and nigericin-induced interleukin-1β release through a dye uptake-independent pathway. *The Journal of Biological Chemistry*. vol. 282, No. 4, pp. 2386-2394.

Pomonis, James D., et al. 2005. Development and pharmacological characterization of a rat model of osteoarthritis pain. *Pain*, vol. 114, pp. 339-346.

Sim, Joan A., et al. 2004. Reanalysis of P2X7 receptor expression in rodent brain. *The Journal of Neuroscience*. vol. 24, No. 28, pp. 6307-6314.

Solle, Mike et al. 2001. Altered Cytokine Production in Mice Lacking $P2X_7$ Receptors. *The Journal of Biological Chemistry*. vol. 276, No. 1, pp. 125-132.

Taylor, Peter C. 2003. Antibody therapy for rheumatoid arthritis. *Current Opinion in Pharmacology*, vol. 3, pp. 323-328.

Terato, Kuniaki et al. 1995. Collagen-Induced Arthritis in Mice: Synergistic Effect of *E. coli* Lipopolysaccharide Bypasses Epitope Specificity in the Induction of Arthritis with Monoclonal Antibodies to Type II Collagen. *Autoimmunity*, vol. 22, pp. 137-147.

Terato, Kuniaki et al. 1992. Induction of Arthritis with Monoclonal Antibodies to Collagen. *The Journal of Immunology*. vol. 148, No. 7, pp. 2103-2108.

Wieland, Heike A., et al. 2005. Osteoarthritis—An Untreatable Disease? *Nature Reviews Drug Discovery*, vol. 4, pp. 331-344.

PCT Written Opinion for corresponding International Application PCT/US2008/007592; (8 pages) for IM06678US01.

International Search Report for corresponding International Application PCT/US2008/007592, mailed Mar. 5, 2009 (4 pages) for IM06678US01.

* cited by examiner

POLYCYCLIC GUANINE DERIVATIVES AND USE THEREOF

FIELD OF THE INVENTION

The present invention relates to Polycyclic Guanine Derivatives, compositions comprising the Polycyclic Guanine Derivatives and methods of using the Polycyclic Guanine Derivatives to treat or prevent pain or an inflammatory disease.

BACKGROUND OF THE INVENTION $P2X_7$ is a ligand-gated ion channel that responds to elevated ATP levels, commonly found at sites of injury and inflammation, by mediating the cellular efflux of $K^+$ and the influx of $Ca^{++}$ and Nat $P2X_7$ is expressed by leukocytes, in particular by T cells, B cells, neutrophils and monocytes/macrophages, and by chondrocytes, synoviocytes, microglia and astrocytes. The major downstream effector function of $P2X_7$ activation is the processing and release of mature forms of the proinflammatory cytokines IL-1β and IL-18 which involves the activation of caspase-1 (ICE). This occurs through the action of NALP3/cryopyrin-dependent inflammasomes. Activation of $P2X_7$ also has been shown to increase levels of other mediators of inflammation including MMPs, $PGE_2$ and TNF-α, although the mechanisms for these effects are not as well studied. There are data supporting a role for $P2X_7$ in signaling cascades such as NF-κB and these pathways might provide a link to non-inflammasome-based mediator production. Current knowledge of $P2X_7$ inhibitors indicates that antagonism of $P2X_7$ in vivo reduces inflammatory cytokines and inflammation and reduces both inflammatory hyperalgesia and neuropathic pain.

Rheumatoid arthritis is another disease linked to the activity of $P2X_7$. Rheumatoid arthritis is characterized by significant synovial inflammation and destruction of extracellular matrix and articular structures including cartilage and bone. Cytokine pathways, including TNF-α, IL-1β, IL-18 and IL-6, are thought to play significant roles in this process. This has been clinically validated for TNF-α and IL-6. Inflamed syriovium contains a variety of cells, including macrophage, T cells, B cells, synoviocytes, fibroblasts and chondrocytes which are known to express $P2X_7$ and contribute to the production of these cytokines. Therefore, $P2X_7$ antagonists are potentially useful as they may inhibit the inflammatory cascade observed in rheumatoid arthritis.

The expression of $P2X_7$ on immune cells and its role in cytokine production also suggest the potential utility of $P2X_7$ antagonists in the treatment of chronic obstructive pulmonary disease (COPD), asthma and inflammatory bowel disease (IBD). $P2X_7$-expressing cells including macrophage, T cells and neutrophils through their mediators such as IL-18 and proteases play important roles in the cascade of events leading to lung tissue destruction and reduced lung function in COPD patients. Similarly, macrophage and T cells and their mediators play important roles in the path physiology of asthma and IBD.

There remains a need in the art for novel compounds which are useful for treating inflammatory diseases and pain. This invention addresses that need.

SUMMARY OF THE INVENTION

In one aspect, the present invention provides compounds having the formula:

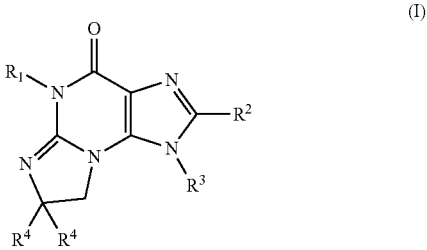

(I)

and pharmaceutically acceptable salts, solvates, esters and prodrugs thereof,
wherein:
$R^1$ is —$C_1$-$C_6$ alkyl or -alkylene-O—$C_1$-$C_6$ alkyl;
$R^2$ is alkyl, aryl, -alkylene-aryl, heterocycloalkyl or heteroaryl, any of which may be optionally substituted with $R^5$;
$R^3$ is alkyl, -alkylene-aryl, cycloalkyl, -alkylene-cycloalkyl or -alkylene-heterocycloalkyl, wherein an aryl, cycloalkyl or heterocycloalkyl group can be optionally substituted with $R^7$;
each occurrence of $R^4$ is independently H or —$C_1$-$C_6$ alkyl, or both $R^4$ groups together with the carbon atom to which they are attached, join to form a 3- to 7-membered cycloalkyl group, which can be optionally fused with a benzene ring;
$R^5$ represents from 1 to 3 groups, each independently selected from alkenyl, alkynyl, aryl, heterocycloalkyl, heteroaryl, halo, —CN, —C(O)OR$^6$, —C(O)R$^6$, —C(O)N(R$^6$)$_2$, —S(O)$_2$NHR$^6$, —OH, —O-alkyl, haloalkyl, —O-haloalkyl and —NHC(O)N(R$^6$)$_2$, where an aryl, heterocycloalkyl or heteroaryl group may be optionally substituted with up to 3 groups, each independently selected from —$C_1$-$C_6$ alkyl, halo, —C(O)OR$^6$ and —C(O)N(R$^6$)$_2$;
each occurrence of $R^6$ is independently H, —$C_1$-$C_6$ alkyl, aryl or heterocycloalkyl, wherein an aryl or heterocycloalkyl group can be optionally substituted with up to 3 groups, each independently selected from alkyl, —O-alkyl, halo, —CN, haloalkyl, -alkylene-C(O)N(R$^8$)$_2$, —C(O)N(R$^8$)$_2$, —C(O)OR$^8$, —C(O)-heterocycloalkyl, —C(O)-alkyl or —N(R$^8$)$_2$;
$R^7$ represents from 1 to 3 groups, each independently selected from —$C_1$-$C_6$ alkyl, halo, aryl, —N(R$^8$)$_2$, —C(O)OR$^8$, —C(O)N(R$^8$)$_2$ and haloalkyl; and
each occurrence of $R^8$ is independently H, —$C_1$-$C_6$ alkyl or aryl:
In another aspect, the invention provides compounds having the formula:

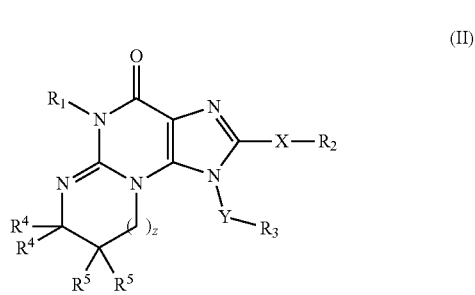

(II)

and pharmaceutically acceptable salts, solvates, esters and prodrugs thereof, wherein:

X is -alkylene-, -alkenylene-, -alkynylene-, -cycloalkylene-, -arylene-, —NH—, —O—, —S—, —S(O)—, —S(O)$_2$—, -heterocycloalkylene- or -heteroarylene-, or X is absent;

Y is -alkylene-, -alkenylene-, -alkynylene-, -cycloalkylene-, -arylene-, —NH—, —O—, —S—, —S(O)—, —S(O)$_2$—, -heterocycloalkylene- or -heteroarylene-, or Y is absent;

$R^1$ is H, alkyl, -(alkylene)$_n$-aryl, -(alkylene)$_n$-cycloalkyl, -(alkylene)$_n$-heteroaryl, -(alkylene)$_n$-heterocycloalkyl, hydroxyalkyl, haloalkyl, -alkylene-alkoxy or -alkylene-N(R$^7$)$_2$, wherein an aryl, cycloalkyl, heterocycloalkyl or heteroaryl group may be optionally substituted with $R^6$;

$R^2$ is H, alkyl, aryl, cycloalkyl, heterocycloalkyl, heteroaryl, hydroxyalkyl, haloalkyl, -alkylene-alkoxy or —N(R$^7$)$_2$, wherein an aryl, cycloalkyl, heterocycloalkyl or heteroaryl group may be optionally substituted with $R^6$;

$R^3$ is H, alkyl, aryl, cycloalkyl, heterocycloalkyl, heteroaryl, hydroxyalkyl, haloalkyl, -alkylene-alkoxy or —N(R$^7$)$_2$, wherein an aryl, cycloalkyl, heterocycloalkyl or heteroaryl group may be optionally substituted with $R^6$;

each occurrence of $R^4$ is independently H, alkyl, -(alkylene)$_n$-aryl, -(alkylene)$_n$-cycloalkyl, -(alkylene)$_n$-heteroaryl, -(alkylene)$_n$-heterocycloalkyl, hydroxyalkyl, haloalkyl, -alkylene-alkoxy or -alkylene-N(R$^7$)$_2$, or both $R^4$ groups together with the carbon atom to which they are attached, join to form a 3-10 membered monocyclic or bicyclic cycloalkyl group or a 3-10 membered monocyclic or bicyclic heterocycloalkyl group, wherein any aryl, cycloalkyl, heterocycloalkyl or heteroaryl group may be optionally substituted with $R^6$;

each occurrence of $R^5$ is independently H, alkyl, -(alkylene)$_n$-aryl, -(alkylene)$_n$-cycloalkyl, -(alkylene)$_n$-heteroaryl, -(alkylene)$_n$-heterocycloalkyl, hydroxyalkyl, haloalkyl, -alkylene-alkoxy or -alkylene-N(R$^7$)$_2$, or both $R^5$ groups together with the carbon atom to which they are attached, join to form a 3-10 membered monocyclic or bicyclic cycloalkyl group or a 3-10 membered monocyclic or bicyclic heterocycloalkyl group having 1 or 2 ring heteroatoms independently selected from —S—, —N—, —O—, —S(O)— and S(O)$_2$—, or any $R^4$ group and any $R^5$ group, together with the carbon atoms to which each are attached, join to form a 3-10 membered monocyclic or bicyclic cycloalkyl group or a 3-10 membered monocyclic or bicyclic heterocycloalkyl group having 1 or 2 ring heteroatoms independently selected from —S—, —N—, —O—, —S(O)— and S(O)$_2$—, wherein any aryl, cycloalkyl, heterocycloalkyl or heteroaryl group may be optionally substituted with $R^6$;

$R^6$ represents from 1 to 3 groups, each independently selected from H, alkyl, aryl, cycloalkyl, heterocycloalkyl, heteroaryl, halo, —CN, —C(O)OR$^7$, —C(O)N(R$^7$)$_2$, —NHC(O)R$^7$, —OC(O)R$^7$, —OH, alkyl, —O-alkyl, aryl, —O-aryl, —NO$_2$, —NHSOR$^7$, —NHSOR$^7$, -(alkylene)$_n$-N(R$^7$)$_2$, haloalkyl, hydroxyalkyl, —O-haloalkyl, —C(O)R$^7$, —NHC(O)N(R$^7$)$_2$ and —NC(O)—OR$^7$;

each occurrence of $R^7$ is independently H, alkyl, -(alkylene)$_n$-aryl, -(alkylene)$_n$-cycloalkyl, -(alkylene)$_n$-heterocycloalkyl or -(alkylene)$_n$-heteroaryl, wherein any aryl, cycloalkyl, heterocycloalkyl or heteroaryl group may be optionally substituted with $R^6$; and Z is 0 or 1.

The Compounds of Formula (I) and (II) and pharmaceutically acceptable salts, solvates, esters and prodrugs thereof (referred to herein as the "Polycyclic Guanine Derivatives") can be useful for treating or preventing pain or an inflammatory disease (each being a "Condition") in a patient.

The invention also provides pharmaceutical compositions, comprising an effective amount of one or more Polycyclic Guanine Derivatives of formula (I) or a pharmaceutically acceptable salt, solvate, ester or prodrug thereof, and a pharmaceutically acceptable carrier. The compositions can be useful for treating or preventing a Condition in a patient.

The invention further provides pharmaceutical compositions comprising an effective amount of one or more Polycyclic Guanine Derivatives of formula (II) or a pharmaceutically acceptable salt, solvate, ester or prodrug thereof, and a pharmaceutically acceptable carrier. The compositions can be useful for treating or preventing a Condition in a patient.

The invention also provides methods for treating or preventing a Condition in a patient, comprising administering to the patient an effective amount of one or more Polycyclic Guanine Derivatives of formula (I).

The invention also provides methods for treating or preventing a Condition in a patient, comprising administering to the patient an effective amount of one or more Polycyclic Guanine Derivatives of formula (II).

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides Polycyclic Guanine Derivatives of Formula (I), pharmaceutical compositions comprising one or more Polycyclic Guanine Derivatives, and methods of using the Polycyclic Guanine Derivatives for treating or preventing a Condition in a patient.

DEFINITIONS AND ABBREVIATIONS

As used above, and throughout this disclosure, the following terms, unless otherwise indicated, shall be understood to have the following meanings:

The term "Polycyclic Guanine Derivative," as used herein, refers collectively to Compounds of Formula (I) and Compounds of Formula (II). In one embodiment, a Polycyclic Guanine Derivative is a compound of formula (I). In another embodiment, a Polycyclic Guanine Derivative is a compound of formula (II). In another embodiment, a Polycyclic Guanine Derivative is any one of illustrative compounds 1-160.

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "effective amount" as used herein, refers to an amount of a Polycyclic Guanine Derivative and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

The term "alkyl," as used herein, refers to an aliphatic hydrocarbon group which may be straight or branched and which contains from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkyl, aryl, cycloalkyl, haloalkyl, —CN, —OH, —O-alkyl, —O-aryl, -alkylene-O-alkyl, —S-alkyl, —NH(cycloalkyl), —O—C(O)-alkyl, —O—C(O)-aryl, —O—C(O)-cycloalkyl, —C(O)OH, —C(O)O-alkyl, —C(O)N($R^{50}$)$_2$ or —N($R^{50}$)$_2$, wherein each occurrence of $R^{50}$ is independently H, alkyl or aryl. In one embodiment, an alkyl group is unsubstituted. In another embodiment, an alkyl group is linear. In another embodiment, an alkyl group is branched.

The term "alkenyl," as used herein, refers to an aliphatic hydrocarbon group containing at least one carbon-carbon double bond and which may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkyl, aryl, cycloalkyl, haloalkyl, —CN, —OH, —O-alkyl, —O-aryl, -alkylene-O-alkyl, —S-alkyl, —NH(cycloalkyl), —O—C(O)-alkyl, —O—C(O)-aryl, —O—C(O)-cycloalkyl, —C(O)OH, —C(O)O-alkyl, —C(O)N($R^{50}$)$_2$ and —N($R^{50}$)$_2$, wherein each occurrence of $R^{50}$ is independently H, alkyl or aryl. In one embodiment, an alkenyl group is unsubstituted.

The term "alkynyl," as used herein, refers to an aliphatic hydrocarbon group containing at least one carbon-carbon triple bond and which may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkyl, aryl, cycloalkyl, haloalkyl, —CN, —OH, —O-alkyl, —O-aryl, -alkylene-O-alkyl, —S-alkyl, —NH(cycloalkyl), —O—C(O)-alkyl, —O—C(O)-aryl, —O—C(O)-cycloalkyl, —C(O)OH, —C(O)O-alkyl, —C(O)N($R^{50}$)$_2$ and —N($R^{50}$)$_2$, wherein each occurrence of $R^{50}$ is independently H, alkyl or aryl. In one embodiment, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$— and —CH$_2$CH(CH$_3$)CH$_2$—. An alkylene group may be unsubstituted or substituted by one or more substituents which may be the same or different, each substituent being independently selected from the group consisting of halo, alkyl, aryl, cycloalkyl, haloalkyl, —CN, —OH, —O-alkyl, —O-aryl, -alkylene-O-alkyl, —S-alkyl, —NH(cycloalkyl), —O—C(O)-alkyl, —O—C(O)-aryl, —O—C(O)-cycloalkyl, —C(O)OH, —C(O)O-alkyl, —C(O)N($R^{50}$)$_2$ and —N($R^{50}$)$_2$, wherein each occurrence of $R^{50}$ is independently H, alkyl or aryl. In one embodiment, an alkylene group is unsubstituted. In another embodiment, an alkylene group has from 1 to about 6 carbon atoms. In another embodiment, an alkylene group is branched. In still another embodiment, an alkylene group is linear.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH$_2$CH═CH—, —CH$_2$CH═CHCH$_2$—, —CH═CHCH$_2$CH$_2$—, —CH$_2$CHCH═CH—, —CH(CH$_3$)CH═CH— and —CH═C(CH$_3$)CH$_2$—. In one embodiment, an alkenylene group has from 2 to about 6 carbon atoms.

The term "alkynylene," as used herein, refers to an alkynyl group, as defined above, wherein one of the alkynyl group's hydrogen atoms has been replaced with a bond. Non-limiting examples of alkynylene groups include —C≡C—, —CH$_2$C≡C—, —CH$_2$C≡CCH$_2$—, —C≡CCH$_2$CH$_2$—, —CH$_2$CHC≡C—, —CH(CH$_3$)C≡C— and —C≡CCH$_2$—. In one embodiment, an alkynylene group has from 2 to about 6 carbon atoms "Aryl" means an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. Non-limiting examples of aryl groups include phenyl and naphthyl. In one embodiment, an aryl group is unsubstituted. In another embodiment, an aryl group is phenyl. In another embodiment, an aryl group is naphthyl. In another embodiment, an aryl group is a phenyl group which is substituted with one F atom. In still another embodiment, an aryl group is a phenyl group which is substituted with two F atoms.

The term "arylene," as used herein, refers to an aryl group, as defined above, wherein one of the aryl group's hydrogen atoms has been replaced with a bond. Non-limiting examples of arylene groups include:

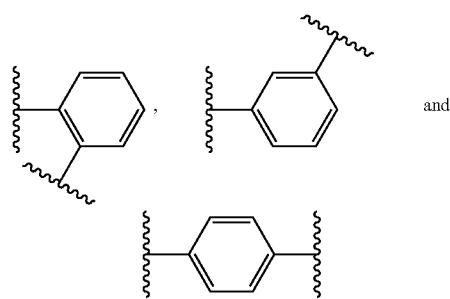

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 5 to about 7 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted.

The term "cycloalkylene," as used herein, refers to a cycloalkyl group, as defined above, wherein one of the cycloalkyl group's hydrogen atoms has been replaced with a bond. Non-limiting examples of cycloalkylene groups include:

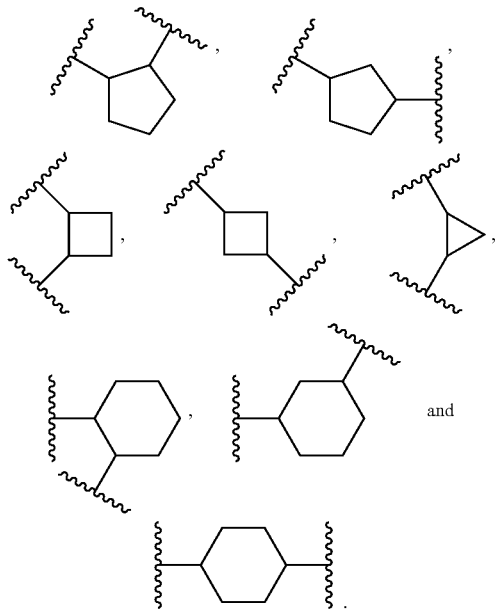

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which has been fused to a benzene ring. Non-limiting examples of heteroaryls include pyridyl, pyrazinyl, furanyl, thienyl, pyrimidinyl, pyridone (including N-substituted pyridones); isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl.

The term "heteroarylene," as used herein, refers to a heteroaryl group, as defined above, wherein one of the heteroaryl group's hydrogen atoms has been replaced with a bond. Non-limiting examples of heteroarylene groups include:

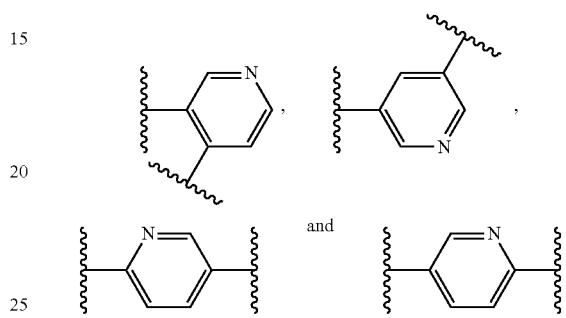

The term "heterocycloalkyl," as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone; and the like. A ring carbon atom of a heterocycloalkyl group may be functionalized as a carbonyl group. An illustrative example of such a heterocycloalkyl group is pyrrolidonyl:

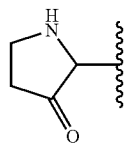

In one embodiment, a heterocycloalkyl group is unsubstituted. In another embodiment, a heterocycloalkyl group is a 5-membered heterocycloalkyl. In another embodiment, a heterocycloalkyl group is a 6-membered heterocycloalkyl.

The term "cycloalkylene," as used herein, refers to a cycloalkyl group, as defined above, wherein one of the cycloalkyl group's hydrogen atoms has been replaced with a bond. Non-limiting examples of cycloalkylene groups include:

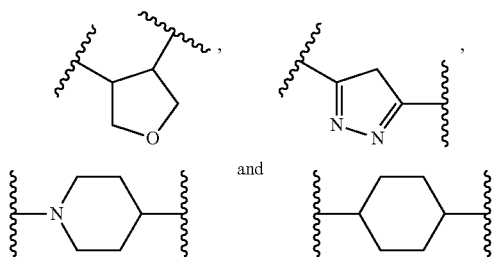

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -alkylene-heteroaryl, -alkenylene-heteroaryl, -alkynylene-heteroaryl, hydroxy, hydroxyalkyl, haloalkyl, —O-alkyl, -alkylene-O-alkyl, —O-aryl, aralkoxy, acyl, aroyl, halo, nitro, cyano, carboxy, —C(O)O-alkyl, —C(O)O-aryl, —C(O)O-alkelene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

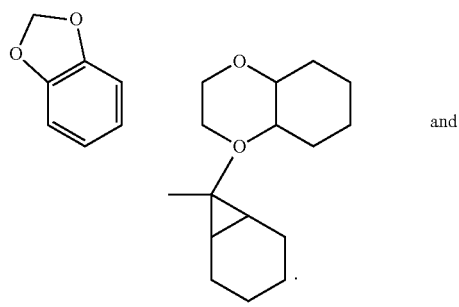

"Halo" means —F, —Cl, —Br or —I. In one embodiment, halo is —Cl or —F. In another embodiment, halo is —F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "purified", "in purified form" or "in isolated and purified form" for a compound refers to the physical state of the compound after being isolated from a synthetic process (e.g. from a reaction mixture), or natural source or combination thereof. Thus, the term "purified", "in purified form" or "in isolated and purified form" for a compound refers to the physical state of the compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, R$^2$, etc.) occurs more than one time in any constituent or in Formula (I) or (II), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a Polycyclic Guanine Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Polycyclic Guanine Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a Polycyclic Guanine Derivative contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, $P(O)(OH)_2$, —$P(O)(O (C_1-C_6)$alkyl$)_2$ or glycosyl (the radical resulting from the removal of a hydroxyl group of the hemiacetal form of a carbohydrate), and the like.

If a Polycyclic Guanine Derivative incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is $H_2O$.

One or more compounds of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Polycyclic Guanine Derivatives can form salts which are also within the scope of this invention. Reference to a Polycyclic Guanine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Polycyclic Guanine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) or (II) may be formed, for example, by reacting a Polycyclic Guanine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared using chiral starting materials or by employing salt resolution techniques. Also, some of the Polycyclic Guanine Derivatives may be atropisomers (e.g., substituted biaryls) and are considered as part of this invention. Enantiomers can also be separated by use of chiral HPLC column.

It is also possible that the Polycyclic Guanine Derivatives may exist in different tautomeric forms, and all such forms are embraced within the scope of the invention. For example, all keto-enol and imine-enamine forms of the compounds are included in the invention and it is understood that tautomeric forms such as, for example, the moieties:

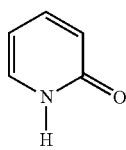 and 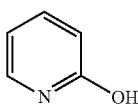

are considered equivalent in certain embodiments of this invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a Polycyclic Guanine Derivative incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Polycyclic Guanine Derivatives (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled Polycyclic Guanine Derivatives can generally be prepared using synthetic chemical procedures analogous to those disclosed herein for making the Compounds of Formulas (I) and (II), by substituting an appropriate isotopically labelled starting material or reagent for a non-isotopically labelled starting material or reagent.

Polymorphic forms of the Polycyclic Guanine Derivatives, and of the salts, solvates, hydrates, esters and prodrugs of the Polycyclic Guanine Derivatives, are intended to be included in the present invention.

The following abbreviations are used below and have the following meanings: t-butyl is tertiary butyl, DIPEA is diisopropylethylamine, DMA is N,N-dimethylacetamide, DME is dimethoxyethane, DMF is N,N-dimethylformamide, DMSO is dimethylsulfoxide, EtOAc is ethyl acetate, EtOH is ethanol, Et$_3$N is triethylamine, i-Pr is isopropyl, LCMS is liquid chromatography mass spectrometry, MeOH is methanol, NaOMe is sodium methoxide, NBS is N-bromosuccinimide, NMP is N-methylpyrrolidone, NMR is nuclear magnetic resonance, Ph is phenyl and THF is tetrahydrofuran.

The Polycyclic Guanine Derivatives

The present invention provides Polycyclic Guanine Derivatives of formulas (I) and (II), compositions thereof and methods of use thereof for treating or preventing a Condition in a patient.

The Polycyclic Guanine Derivatives of Formula (I)

In one embodiment, the present invention provides compound having the formula:

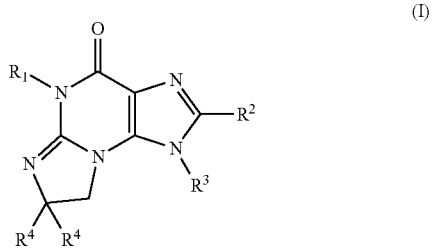

and pharmaceutically acceptable salts, solvates, esters and prodrugs thereof, wherein $R^1$, $R^2$, $R^3$ and $R^4$ are defined above for the Compounds of Formula (I).

In one embodiment, $R^1$ is —$C_1$-$C_6$ alkyl.
In another embodiment, $R^1$ is methyl or ethyl.
In another embodiment, $R^1$ is ethyl.
In one embodiment, $R^2$ is aryl.
In another embodiment, $R^2$ is -alkylene-aryl.
In another embodiment, $R^2$ is heteroaryl.
In another embodiment, $R^2$ is heterocycloalkyl.
In one embodiment, $R^2$ is phenyl, which can be substituted with $R^5$.
In another embodiment, $R^2$ is benzyl, which can be optionally substituted with $R^5$.
In another embodiment, $R^2$ is pyridyl, which can be optionally substituted with $R^5$.
In another embodiment, $R^2$ is piperidinyl or piperazinyl, which are optionally substituted with $R^5$.
In one embodiment, $R^2$ is -A-B, wherein A is heteroaryl and B is alkyl, aryl, -alkylene-aryl, heterocycloalkyl or heteroaryl, wherein A and B can be optionally substituted as set forth above for the compounds of formula (I).
In another embodiment, $R^2$ is -A-B, wherein A is heteroaryl and B is aryl, wherein A and B can be optionally substituted as set forth above for the compounds of formula (I).
In another embodiment, $R^2$ is -A-B, wherein A is 6-membered heteroaryl and B is aryl, wherein A and B can be optionally substituted as set forth above for the compounds of formula (I).
In still another embodiment, $R^2$ is -A-B, wherein A is pyridyl and B is aryl, wherein A and B can be optionally substituted as set forth above for the compounds of formula (I).
In another embodiment, $R^2$ is -A-B, wherein A is heteroaryl and B is phenyl, wherein A and B can be optionally substituted as set forth above for the compounds of formula (I).
In yet another embodiment, $R^2$ is -A-B, wherein A is 6-membered heteroaryl and B is phenyl, wherein A and B can be optionally substituted as set forth above for the compounds of formula (I).
In another embodiment, $R^2$ is -A-B, wherein A is pyridyl and B is phenyl, wherein A and B can be optionally substituted as set forth above for the compounds of formula (I).
In a further embodiment, $R^2$ is -A-B, wherein B is heteroaryl and A is alkyl, aryl, -alkylene-aryl, heterocycloalkyl or heteroaryl, wherein A and B can be optionally substituted as set forth above for the compounds of formula (I).

In another embodiment, $R^2$ is -A-B, wherein B is heteroaryl and A is aryl, wherein A and B can be optionally substituted as set forth above for the compounds of formula (I).
In one embodiment, $R^2$ is -A-B, wherein B is 6-membered heteroaryl and A is aryl, wherein A and B can be optionally substituted as set forth above for the compounds of formula (I).
In another embodiment, $R^2$ is -A-B, wherein B is pyridyl and A is aryl, wherein A and B can be optionally substituted as set forth above for the compounds of formula (I).
In another embodiment, $R^2$ is -A-B, wherein B is heteroaryl and A is phenyl, wherein A and B can be optionally substituted as set forth above for the compounds of formula (I).
In still another embodiment, $R^2$ is -A-B, wherein B is 6-membered heteroaryl and A is phenyl, wherein A and B can be optionally substituted as set forth above for the compounds of formula (I).
In another embodiment, $R^2$ is -A-B, wherein B is pyridyl and A is phenyl, wherein A and B can be optionally substituted as set forth above for the compounds of formula (I).
In one embodiment, $R^2$ is:

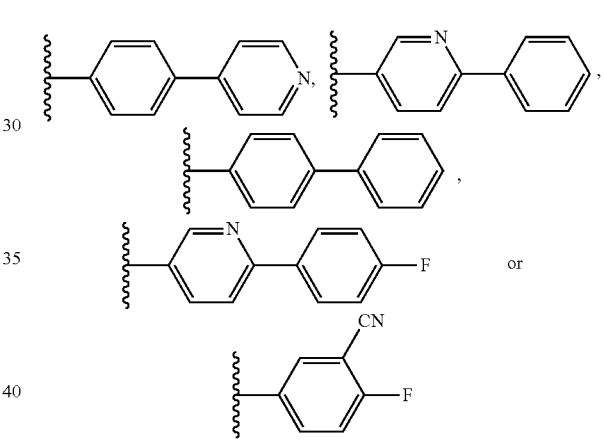

In another embodiment, $R^2$ is:

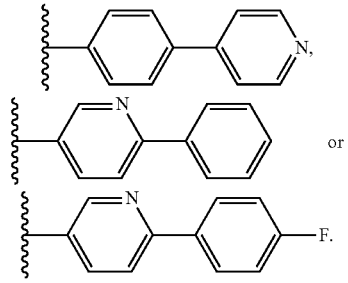

In one embodiment, $R^3$ is -alkylene-aryl, or -alkylene-heterocycloalkyl, wherein an aryl or heterocycloalkyl group can be optionally substituted with $R^7$.
In another embodiment, $R^3$ is -alkylene-aryl, or -alkylene-heterocycloalkyl, wherein an aryl or heterocycloalkyl group can be optionally substituted with $R^7$, wherein $R^7$ represents from 1 to 3 halo groups, which can be the same or different.
In one embodiment, $R^3$ is -alkylene-aryl.
In another embodiment, $R^3$ is -alkylene-cycloalkyl.

In another embodiment, $R^3$ is —$CH_2$-aryl.

In still another embodiment, $R^3$ is —$CH_2$-phenyl, wherein the phenyl group can be optionally substituted with $R^7$.

In another embodiment, $R^3$ is —$CH_2$-phenyl, wherein the phenyl group is substituted with one or two F atoms.

In another embodiment, $R^3$ is —$CH_2$-phenyl, wherein the phenyl group is monosubstituted with one F atom.

In another embodiment, $R^3$ is —$CH_2$-phenyl, wherein the phenyl group is disubstituted with two F atoms.

In one embodiment, $R^3$ is:

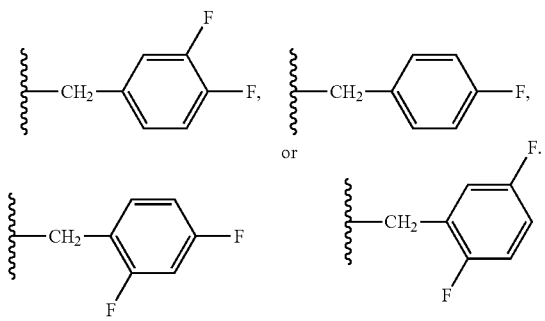

In yet another embodiment, $R^3$ is —$CH_2$-cycloalkyl.

In a further embodiment, $R^3$ is —$CH_2$-cyclobutyl or —$CH_2$-cyclohexyl.

In one embodiment, each occurrence of $R^4$ is independently H or —$C_1$-$C_6$ alkyl.

In another embodiment, each occurrence of $R^4$ is independently H, methyl, isopropyl, sec-butyl or t-butyl.

In another embodiment, one occurrence of $R^4$ is H and the other is —$C_1$-$C_6$ alkyl.

In still another embodiment, one occurrence of $R^4$ is H and the other is methyl, isopropyl, sec-butyl or t-butyl.

In yet another embodiment, one occurrence of $R^4$ is H and the other is isopropyl.

In another embodiment, each occurrence of $R^4$ is —$C_1$-$C_6$ alkyl.

In still another embodiment, each occurrence of $R^4$ is methyl.

In one embodiment, one occurrence of $R^4$ is H and the other is cycloalkyl.

In another embodiment, one occurrence of $R^4$ is H and the other is cyclopropyl.

In one embodiment, both $R^4$ groups, together with the carbon atom to which they are attached, join to form a 3- to 7-membered cycloalkyl group.

In another embodiment, both $R^4$ groups, together with the carbon atom to which they are attached, join to form a 5-membered cycloalkyl group.

In another embodiment, both $R^4$ groups, together with the carbon atom to which they are attached, join to form a 6-membered cycloalkyl group. In still another embodiment, both $R^4$ groups, together with the carbon atom to which they are attached, join to form a 5-membered cycloalkyl group which is fused to a benzene ring.

In yet another embodiment, both $R^4$ groups, together with the carbon atom to which they are attached, join to form a 6-membered cycloalkyl group which is fused to a benzene ring.

In one embodiment, $R^1$ is —$C_1$-$C_6$ alkyl and $R^2$ is phenyl, which can be substituted with $R^5$ In another embodiment, $R^1$ is —$C_1$-$C_6$ alkyl and $R^2$ is benzyl, which can be optionally Substituted with $R^5$.

In another embodiment, $R^1$ is —$C_1$-$C_6$ alkyl and $R^2$ is pyridyl, which can be optionally substituted with $R^5$.

In still another embodiment, $R^1$ is —$C_1$-$C_6$ alkyl and $R^2$ is piperidinyl or piperazinyl, which are optionally substituted with $R^5$.

In one embodiment, $R^1$ is —$C_1$-$C_6$ alkyl; $R^2$ is phenyl, which can be substituted with $R^5$; and $R^3$ is —$CH_2$-phenyl, wherein the phenyl group can be optionally substituted with $R^7$.

In another embodiment, $R^1$ is —$C_1$-$C_6$ alkyl; $R^2$ is benzyl; which can be optionally substituted with $R^5$; and $R^3$ is —$CH_2$-phenyl, wherein the phenyl group can be optionally substituted with $R^7$.

In another embodiment, $R^1$ is —$C_1$-$C_6$ alkyl; $R^2$ is pyridyl; which can be optionally substituted with $R^5$; and $R^3$ is —$CH_2$-phenyl, wherein the phenyl group can be optionally substituted with $R^7$.

In still another embodiment, $R^1$ is —$C_1$-$C_6$ alkyl; $R^2$ is piperidinyl or piperazinyl; which are optionally substituted with $R^5$; and $R^3$ is —$CH_2$-phenyl, wherein the phenyl group is substituted with 1 or 2 F atoms.

In one embodiment, $R^1$ is —$C_1$-$C_6$ alkyl; $R^2$ is phenyl; which can be substituted with $R^5$; and $R^3$ is —$CH_2$-phenyl, wherein the phenyl group is substituted with one or two F atoms.

In another embodiment, $R^1$ is —$C_1$-$C_6$ alkyl; $R^2$ is benzyl; which can be optionally substituted with $R^5$; and $R^3$ is —$CH_2$-phenyl, wherein the phenyl group is substituted with one or two F atoms.

In another embodiment, $R^1$ is —$C_1$-$C_6$ alkyl; $R^2$ is pyridyl; which can be optionally substituted with $R^5$; and $R^3$ is —$CH_2$-phenyl, wherein the phenyl group is substituted with one or two F atoms.

In still another embodiment, $R^1$ is —$C_1$-$C_6$ alkyl; $R^2$ is piperidinyl or piperazinyl; which are optionally substituted with $R^5$; and $R^3$ is —$CH_2$-phenyl, wherein the phenyl group is substituted with one or two F atoms.

In one embodiment, $R^1$ is —$C_1$-$C_6$ alkyl; $R^2$ is phenyl; which can be substituted with $R^5$; and $R^3$ is —$CH_2$-cyclohexyl or —$CH_2$-cyclobutyl.

In another embodiment, $R^1$ is —$C_1$-$C_6$ alkyl; $R^2$ is benzyl; which can be optionally substituted with $R^5$; and $R^3$ is —$CH_2$-cyclohexyl or —$CH_2$-cyclobutyl.

In another embodiment, $R^1$ is —$C_1$-$C_6$ alkyl; $R^2$ is pyridyl; which can be optionally substituted with $R^5$; and $R^3$ is —$CH_2$-cyclohexyl or —$CH_2$-cyclobutyl.

In still another embodiment, $R^1$ is —$C_1$-$C_6$ alkyl; $R^2$ is piperidinyl or piperazinyl; which are optionally substituted with $R^5$; and $R^3$ is —$CH_2$-cyclohexyl or —$CH_2$-cyclobutyl.

In one embodiment, $R^1$ is —$C_1$-$C_6$ alkyl; $R^2$ is phenyl; which can be substituted with $R^5$; $R^3$ is —$CH_2$-phenyl, wherein the phenyl group can be optionally substituted with $R^7$; and each $R^4$ group is independently selected from H and $C_1$-$C_6$ alkyl.

In another embodiment, $R^1$ is —$C_1$-$C_6$ alkyl; $R^2$ is benzyl; which can be optionally substituted with $R^5$; $R^3$ is —$CH_2$-phenyl, wherein the phenyl group can be optionally substituted with $R^7$; and each $R^4$ group is independently selected from H and $C_1$-$C_6$ alkyl.

In another embodiment, $R^1$ is —$C_1$-$C_6$ alkyl; $R^2$ is pyridyl; which can be optionally substituted with $R^5$; $R^3$ is —$CH_2$-phenyl, wherein the phenyl group can be optionally substituted with $R^7$; and each $R^4$ group is independently selected from H and $C_1$-$C_6$ alkyl.

In still another embodiment, $R^1$ is —$C_1$-$C_6$ alkyl; $R^2$ is piperidinyl or piperazinyl; which are optionally substituted with $R^5$; $R^3$ is —$CH_2$-phenyl, wherein the phenyl group is substituted with one or two F atoms; and each R⁴ group is independently selected from H and $C_1$-$C_6$ alkyl.

In one embodiment, R¹ is —$C_1$-$C_6$ alkyl; R² is phenyl; which can be substituted with R⁵; R³ is —$CH_2$-phenyl, wherein the phenyl group is substituted with one or two F atoms; and each R⁴ group is independently selected from H and $C_1$-$C_6$ alkyl.

In another embodiment, R¹ is —$C_1$-$C_6$ alkyl; R² is benzyl; which can be optionally substituted with R⁵; R³ is —$CH_2$-phenyl, wherein the phenyl group is substituted with one or two F atoms; and each R⁴ group is independently selected from H and $C_1$-$C_6$ alkyl.

In another embodiment, R¹ is —$C_1$-$C_6$ alkyl; R² is pyridyl; which can be optionally substituted with R⁵; R³ is —$CH_2$-phenyl, wherein the phenyl group is substituted with one or two F atoms; and each R⁴ group is independently selected from H and $C_1$-$C_6$ In still another embodiment, R¹ is —$C_1$-$C_6$ alkyl; R² is piperidinyl or piperazinyl; which are optionally substituted with R⁵; R³ is —$CH_2$-phenyl, wherein the phenyl group is substituted with one or two F atoms; and each R⁴ group is independently selected from H and $C_1$-$C_6$ alkyl.

In one embodiment, R¹ is —$C_1$-$C_6$ alkyl; R² is phenyl; which can be substituted with R⁵; R³ is —$CH_2$-cyclohexyl or —$CH_2$-cyclobutyl; d each R⁴ group is independently selected from H and $C_1$-$C_6$ alkyl.

In another embodiment, R¹ is —$C_1$-$C_6$ alkyl, R² is benzyl, which can be optionally substituted with R⁵, R³ is —$CH_2$-cyclohexyl or —$CH_2$-cyclobutyl; and each R⁴ group is independently selected from H and $C_1$-$C_6$ alkyl.

In another embodiment, R¹ is —$C_1$-$C_6$ alkyl; R² is pyridyl; which can be optionally substituted with R⁵; R³ is —$CH_2$-cyclohexyl or —$CH_2$-cyclobutyl; and each R⁴ group is independently selected from H and $C_1$-$C_6$ alkyl.

In still another embodiment, R¹ is —$C_1$-$C_6$ alkyl; R² is piperidinyl or piperazinyl; which are optionally substituted with R⁵; R³ is —$CH_2$-cyclohexyl or —$CH_2$-cyclobutyl; and each R⁴ group is independently selected from H and $C_1$-$C_6$ alkyl.

In one embodiment, R¹ is —$C_1$-$C_6$ alkyl; R² is phenyl; which can be substituted with R⁵; R³ is —$CH_2$-phenyl, wherein the phenyl group can be optionally substituted with R⁷; and both R⁴ groups, together with the carbon atom to which they are attached, join to form a 5- or 6-membered cycloalkyl ring, which may be optionally, fused with a benzene ring.

In another embodiment, R¹ is —$C_1$-$C_6$ alkyl; R² is benzyl, which can be optionally substituted with R⁵; R³ is —$CH_2$-phenyl, wherein the phenyl group can be optionally substituted with R⁷; and both R⁴ groups, together with the carbon atom to which they are attached, join to form a 5- or 6-membered cycloalkyl ring, which may be optionally fused with a benzene ring.

In another embodiment, R¹ is —$C_1$-$C_6$ alkyl; R² is pyridyl; which can be optionally substituted with R⁵, R³ is —$CH_2$-phenyl, wherein the phenyl group can be optionally substituted with R⁷; and both R⁴ groups, together with the carbon atom to which they are attached, join to form a 5- or 6-membered cycloalkyl ring, which may be optionally fused with a benzene ring.

In still another embodiment, R¹ is —$C_1$-$C_6$ alkyl; R² is piperidinyl or piperazinyl, which are optionally substituted with R⁵; R³ is —$CH_2$-phenyl, wherein the phenyl group is substituted with one or two F atoms; and both R⁴ groups, together with the carbon atom to which they are attached, join to form a 5- or 6-membered cycloalkyl ring, which may be optionally fused with a benzene ring.

In one embodiment, R¹ is —$C_1$-$C_6$ alkyl; R² is phenyl, which can be substituted with R⁵; R³ is —$CH_2$-phenyl, wherein the phenyl group is substituted with one or two F atoms; and both R⁴ groups, together with the carbon atom to which they are attached, join to form a 5- or 6-membered cycloalkyl ring, which may be optionally fused with a benzene ring.

In another embodiment, R¹ is —$C_1$-$C_6$ alkyl; R² is benzyl, which can be optionally substituted with R⁵; R³ is —$CH_2$-phenyl, wherein the phenyl group is substituted with one or two F atoms; and both R⁴ groups, together with the carbon atom to which they are attached, join to form a 5- or 6-membered cycloalkyl ring, which may be optionally fused with a benzene ring.

In another embodiment, R¹ is —$C_1$-$C_6$ alkyl; R² is pyridyl, which can be optionally substituted with R⁵; R³ is —$CH_2$-phenyl, wherein the phenyl group is substituted with one or two F atoms; and both R⁴ groups, together with the carbon atom to which they are attached, join to form a 5- or 6-membered cycloalkyl ring, which may be optionally fused with a benzene ring.

In still another embodiment, R¹ is —$C_1$-$C_6$ alkyl; R² is piperidinyl or piperazinyl, which are optionally substituted with R⁵; R³ is —$CH_2$-phenyl, wherein the phenyl group is substituted with one or two F atoms; and both R⁴ groups, together with the carbon atom to which they are attached, join to form a 5- or 6-membered cycloalkyl ring, which may be optionally fused with a benzene ring.

In one embodiment, R¹ is —$C_1$-$C_6$ alkyl; R² is phenyl, which can be substituted with R⁵; R³ is —$CH_2$-cyclohexyl or —$CH_2$-cyclobutyl; and both R⁴ groups, together with the carbon atom to which they are attached, join to form a 5- or 6-membered cycloalkyl ring, which may be optionally fused with a benzene ring.

In another embodiment, R¹ is —$C_1$-$C_6$ alkyl; R² is benzyl, which can be optionally substituted with R⁵; R³ is —$CH_2$-cyclohexyl or —$CH_2$-cyclobutyl; and both R⁴ groups, together with the carbon atom to which they are attached, join to form a 5- or 6-membered cycloalkyl ring, which may be optionally fused with a benzene ring.

In another embodiment, R¹ is —$C_1$-$C_6$ alkyl; R² is pyridyl, which can be optionally substituted with R⁵; R³ is —$CH_2$-cyclohexyl or —$CH_2$-cyclobutyl; and both R⁴ groups, together with the carbon atom to which they are attached, join to form a 5- or 6-membered cycloalkyl ring, which may be optionally fused with a benzene ring.

In still another embodiment, R¹ is —$C_1$-$C_6$ alkyl; R² is piperidinyl or piperazinyl, which are optionally substituted with R⁵; R³ is —$CH_2$-cyclohexyl or —$CH_2$-cyclobutyl; and both R⁴ groups, together with the carbon atom to which they are attached, join to form a 5- or 6-membered cycloalkyl ring, which may be optionally fused with a benzene ring.

In one embodiment, R¹ is methyl or ethyl; R² is:

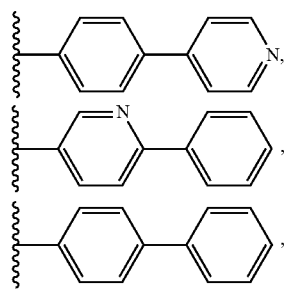

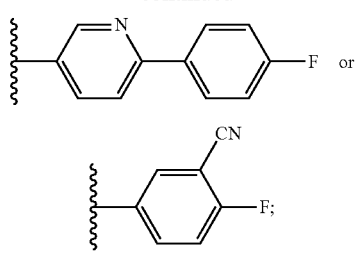

or $R^3$ is:

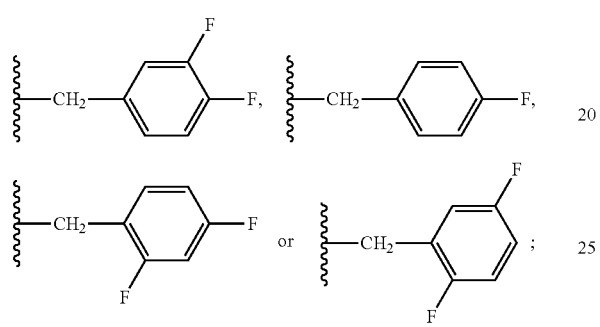

and both $R^4$ groups, together with the carbon atom to which they are attached, join to form a 5- or 6-membered cycloalkyl ring, which may be optionally fused with a benzene ring.

In another embodiment, $R^1$ is methyl or ethyl; $R^2$ is:

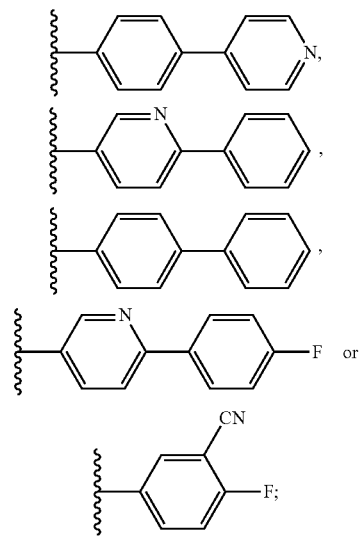

$R^3$ is:

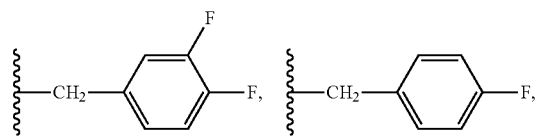

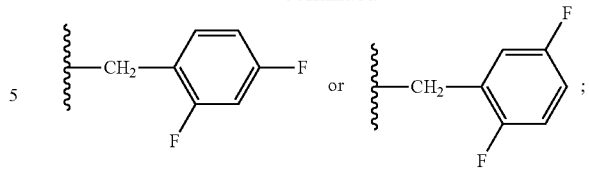

and each $R^4$ groups is independently —$C_1$-$C_6$ alkyl.

In another embodiment, $R^1$ is methyl or ethyl; $R^2$ is:

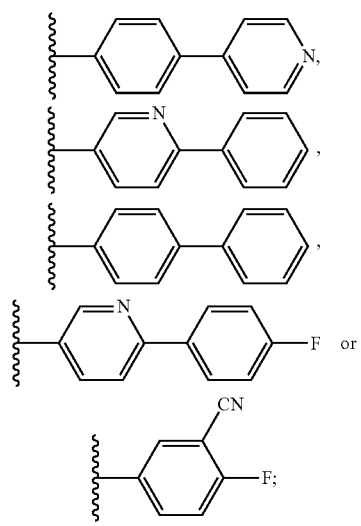

$R^3$ is:

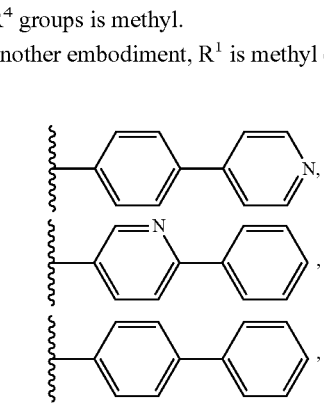

and each $R^4$ groups is methyl.

In still another embodiment, $R^1$ is methyl or ethyl; $R^2$ is:

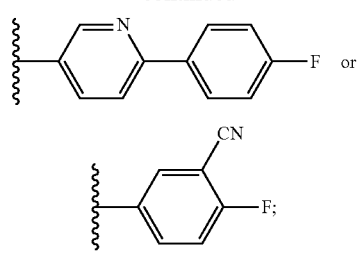

$R^3$ is:

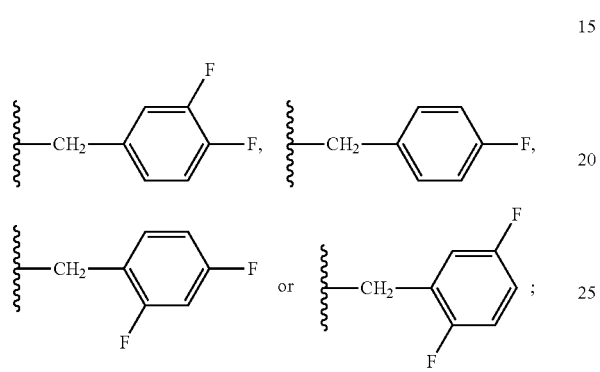

and one $R^4$ group is H and the other $R^4$ group is —$C_1$-$C_6$ alkyl.

In yet another embodiment, $R^1$ is methyl or ethyl; $R^2$ is:

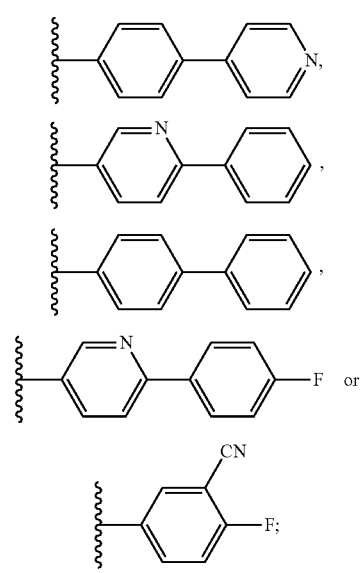

$R^3$ is:

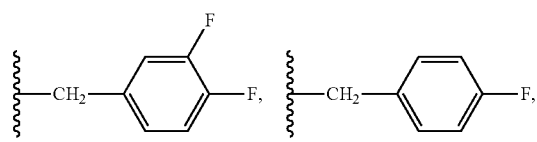

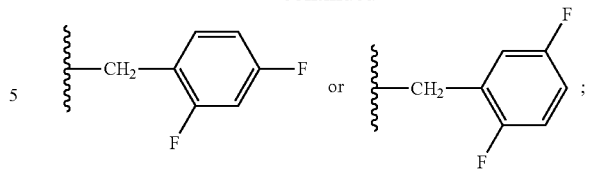

and one $R^4$ group is H and the other $R^4$ group is isopropyl.

In one embodiment, $R^1$ is methyl or ethyl; $R^2$ is:

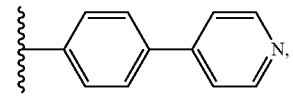

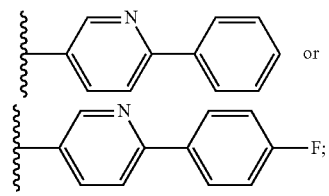

$R^3$ is:

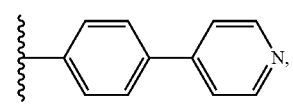

and both $R^4$ groups, together with the carbon atom to which they are attached, join to form a 5- or 6-membered cycloalkyl ring, which may be optionally fused with a benzene ring.

In another embodiment, $R^1$ is methyl or ethyl; $R^2$ is:

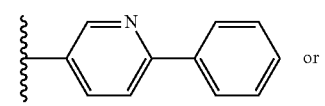

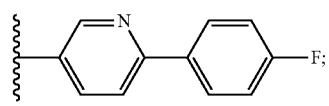

$R^3$ is:

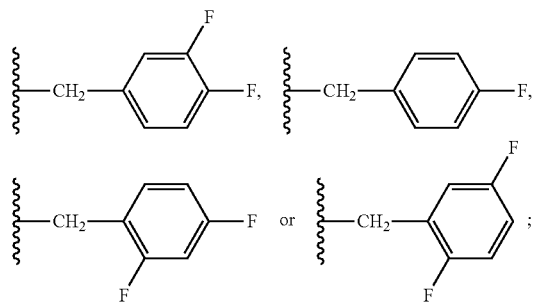

and each $R^4$ groups is independently —$C_1$-$C_6$ alkyl.

In another embodiment, $R^1$ is methyl or ethyl; $R^2$ is:

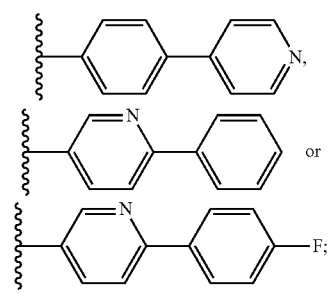

$R^3$ is:

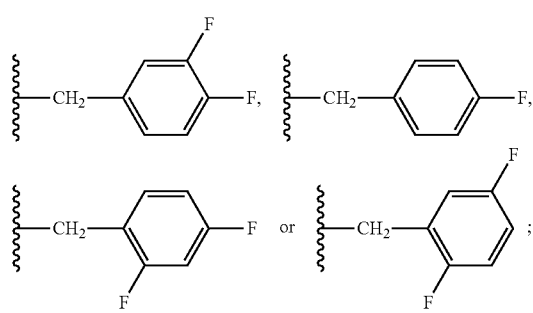

and each $R^4$ groups is methyl.

In still another embodiment, $R^1$ is methyl or ethyl; $R^2$ is:

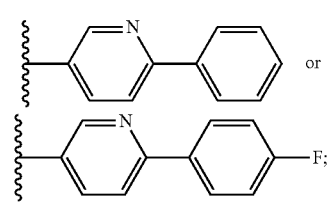

$R^3$ is:

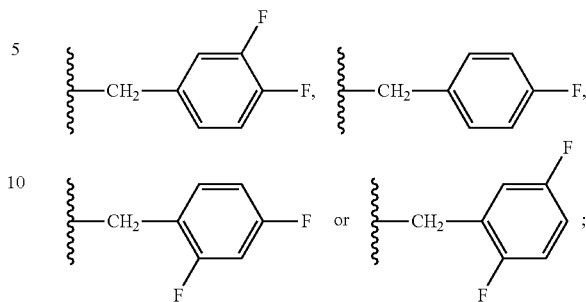

and one $R^4$ group is H and the other $R^4$ group is —$C_1$-$C_6$ alkyl.

In yet another embodiment, $R^1$ is methyl or ethyl; $R^2$ is:

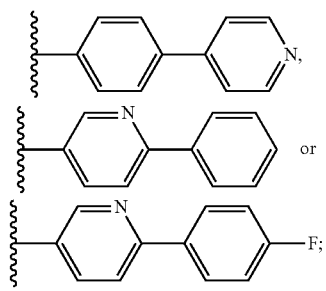

$R^3$ is:

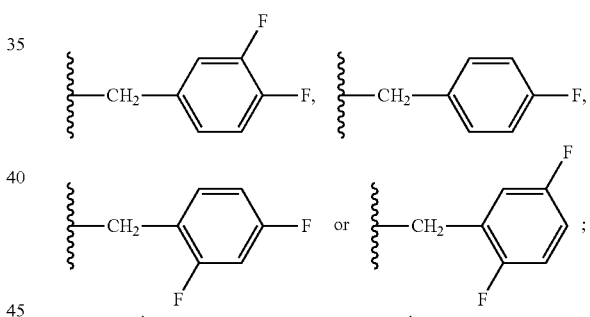

and one $R^4$ group is H and the other $R^4$ group is isopropyl.

In one embodiment, for the Compounds of Formula (I), variables $R^1$, $R^2$, $R^3$ and $R^4$ are selected independently of each other.

In another embodiment, a compound of formula (I) is in purified form.

In another embodiment, a compound of formula (I) can be an antagonist of $P2X_7$.

In one embodiment, the compounds of formula (I) have the formula (Ia):

(Ia)

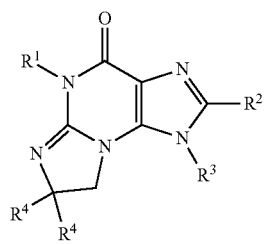

and pharmaceutically acceptable salts, solvates, esters and prodrugs thereof,
wherein:

$R^1$ is —$C_1$-$C_6$ alkyl;

$R^2$ is -A-B,

A is alkyl, aryl, -alkylene-aryl, heterocycloalkyl or heteroaryl, any of which may be optionally substituted with $R^5$;

B is alkyl, aryl, -alkylene-aryl, heterocycloalkyl or heteroaryl, any of which may be optionally substituted with $R^5$ such that at least one of A and B is heteroaryl;

$R^3$ is -alkylene-aryl, wherein the aryl moiety can be optionally substituted with $R^7$;

each occurrence of $R^4$ is independently H or —$C_1$-$C_6$ alkyl, or both $R^4$ groups together with the carbon atom to which they are attached, join to form a 3- to 7-membered cycloalkyl group, which can be optionally fused with a benzene ring;

$R^5$ represents from 1 to 3 groups, each independently selected from aryl, heterocycloalkyl, heteroaryl, halo, —CN, —C(O)O$R^6$, —C(O)$R^6$, —C(O)N($R^6$)$_2$, —S(O)$_2$NH$R^6$, —OH, —O-alkyl, haloalkyl, —O-haloalkyl and —NHC(O)N($R^6$)$_2$, where an aryl, heterocycloalkyl or heteroaryl group may be optionally substituted with up to 3 groups, each independently selected from —$C_1$-$C_6$ alkyl, halo, —C(O)O$R^6$ and —C(O)N($R^6$)$_2$;

each occurrence of $R^6$ is independently H, —$C_1$-$C_6$ alkyl, aryl or heterocycloalkyl;

$R^7$ represents from 1 to 3 groups, each independently selected from —$C_1$-$C_6$ alkyl, halo, aryl, —N($R^8$)$_2$, —C(O)O$R^8$, —C(O)N($R^8$)$_2$ and haloalkyl; and each occurrence of $R^8$ is independently H, —$C_1$-$C_6$ alkyl or aryl.

In one embodiment, $R^1$ is —$C_1$-$C_6$ alkyl.

In another embodiment, $R^1$ is methyl or ethyl.

In another embodiment, $R^1$ is ethyl.

In one embodiment, $R^2$ is aryl.

In another embodiment, $R^2$ is -alkylene-aryl.

In another embodiment, $R^2$ is heteroaryl.

In another embodiment, $R^2$ is heterocycloalkyl.

In one embodiment, $R^2$ is phenyl, which can be substituted with $R^5$.

In another embodiment, $R^2$ is benzyl, which can be optionally substituted with $R^5$.

In another embodiment, $R^2$ is pyridyl, which can be optionally substituted with $R^5$.

In another embodiment, $R^2$ is piperidinyl or piperazinyl, which are optionally substituted with $R^5$.

In one embodiment, $R^2$ is -A-B, wherein A is heteroaryl and B is alkyl, aryl, -alkylene-aryl, heterocycloalkyl or heteroaryl, wherein A and B can be optionally substituted as set forth above for the compounds of formula (I).

In another embodiment, $R^2$ is -A-B, wherein A is heteroaryl and B is aryl, wherein A and B can be optionally substituted as set forth above for the compounds of formula (I).

In another embodiment, $R^2$ is -A-B, wherein A is 6-membered heteroaryl and B is aryl, wherein A and B can be optionally substituted as set forth above for the compounds of formula (I).

In still another embodiment, $R^2$ is -A-B, wherein A is pyridyl and B is aryl, wherein A and B can be optionally substituted as set forth above for the compounds of formula (I).

In another embodiment, $R^2$ is -A-B, wherein A is heteroaryl and B is phenyl, wherein A and B can be optionally substituted as set forth above for the compounds of formula (I).

In yet another embodiment, $R^2$ is -A-B, wherein A is 6-membered heteroaryl and B is phenyl, wherein A and B can be optionally substituted as set forth above for the compounds of formula (I).

In another embodiment, $R^2$ is -A-B, wherein A is pyridyl and B is phenyl, wherein A and B can be optionally substituted as set forth above for the compounds of formula (I).

In a further embodiment, $R^2$ is -A-B, wherein B is heteroaryl and A is alkyl, aryl, -alkylene-aryl, heterocycloalkyl or heteroaryl, wherein A and B can be optionally substituted as set forth above for the compounds of formula (I).

In another embodiment, $R^2$ is -A-B, wherein B is heteroaryl and A is aryl, wherein A and B can be optionally substituted as set forth above for the compounds of formula (I).

In one embodiment, $R^2$ is -A-B, wherein B is 6-membered heteroaryl and A is aryl, wherein A and B can be optionally substituted as set forth above for the compounds of formula (I).

In another embodiment, $R^2$ is -A-B, wherein B is pyridyl and A is aryl, wherein A and B can be optionally substituted as set forth above for the compounds of formula (I).

In another embodiment, $R^2$ is -A-B, wherein B is heteroaryl and A is phenyl, wherein A and B can be optionally substituted as set forth above for the compounds of formula (I).

In still another embodiment, $R^2$ is -A-B, wherein B is 6-membered heteroaryl and A is phenyl, wherein A and B can be optionally substituted as set forth above for the compounds of formula (I).

In another embodiment, $R^2$ is -A-B, wherein B is pyridyl and A is phenyl, wherein A and B can be optionally substituted as set forth above for the compounds of formula (I).

In one embodiment, $R^2$ is:

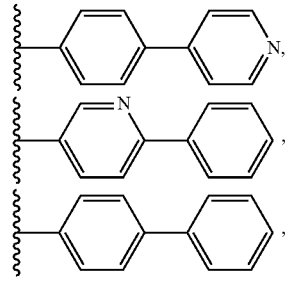

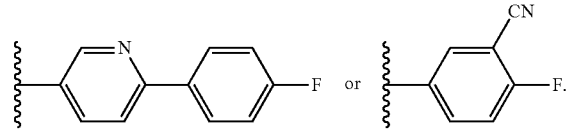

In another embodiment, $R^2$ is:

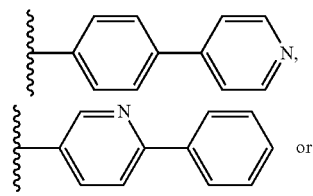

-continued

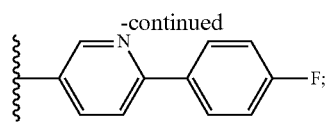

In another embodiment, R³ is —CH₂-aryl.

In still another embodiment, R³ is —CH₂-phenyl, wherein the phenyl group can be optionally substituted with R⁷.

In another embodiment, R³ is —CH₂-phenyl, wherein the phenyl group is substituted with one or two F atoms.

In yet another embodiment, R³ is —CH₂-phenyl, wherein the phenyl group is monosubstituted with one F atom.

In another embodiment, R³ is —CH₂-phenyl, wherein the phenyl group is disubstituted with two F atoms.

In another embodiment, R³ is:

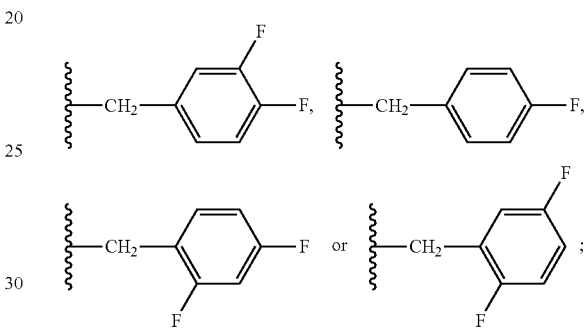

In one embodiment, R¹ is methyl or ethyl; A is heteroaryl and B is aryl, wherein A and B can be optionally substituted as set forth above for the compounds of formula (I); R³ is —CH₂-phenyl, wherein the phenyl group is substituted with one or two F atoms; and each occurrence of R⁴ is independently H or $C_1$-$C_6$ alkyl.

In another embodiment, R¹ is methyl or ethyl; A is aryl and B is heteroaryl, wherein A and B can be optionally substituted as set forth above for the compounds of formula (I); R³ is —CH₂-phenyl, wherein the phenyl group is substituted with one or two F atoms; and each occurrence of R⁴ is independently H or $C_1$-$C_6$ alkyl.

In another embodiment, R¹ is methyl or ethyl; A is heteroaryl and B is aryl, wherein A and B can be optionally substituted as set forth above for the compounds of formula (I); R³ is —CH₂-phenyl, wherein the phenyl group is substituted with one or two F atoms; and each occurrence of R⁴ is independently H, methyl or isopropyl.

In still another embodiment, R¹ is methyl or ethyl; A is aryl and B is heteroaryl, wherein A and B can be optionally substituted as set forth above for the compounds of formula (I); R³ is —CH₂-phenyl, wherein the phenyl group is substituted with one or two F atoms; and each occurrence of R⁴ is independently H, methyl or isopropyl.

In another embodiment, R¹ is methyl or ethyl; A is pyridyl and B is phenyl, wherein A and B can be optionally substituted as set forth above for the compounds of formula (I); R³ is —CH₂-phenyl, wherein the phenyl group is substituted with one or two F atoms; and each occurrence of R⁴ is independently H, methyl or isopropyl.

In another embodiment, R¹ is methyl or ethyl; A is phenyl and B is pyridyl, wherein A and B can be optionally substituted as set forth above for the compounds of formula (I); R³ is —CH₂-phenyl, wherein the phenyl group is substituted with one or two F atoms; and each occurrence of R⁴ is independently H, methyl or isopropyl.

In yet another embodiment, R¹ is methyl or ethyl; A and B are each pyridyl, wherein A and B can be optionally substituted as set forth above for the compounds of formula (I); R³ is —CH₂-phenyl, wherein the phenyl group is substituted with one or two F atoms; and each occurrence of R⁴ is independently H, methyl or isopropyl.

In a further embodiment, R¹ is methyl or ethyl; A and B are each phenyl, wherein A and B can be optionally substituted as set forth above for the compounds of formula (I); R³ is —CH₂-phenyl, wherein the phenyl group is substituted with one or two F atoms; and each occurrence of R⁴ is independently H, methyl or isopropyl.

In one embodiment, R¹ is methyl or ethyl; one of A and B is pyridyl and the other is phenyl or pyridyl, wherein A and B can be optionally substituted as set forth above for the compounds of formula (I); R³ is:

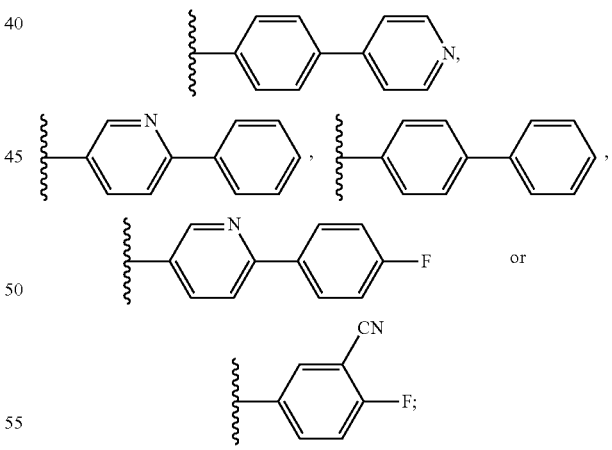

and each occurrence of R⁴ is independently H, methyl or isopropyl.

In another embodiment, R¹ is methyl or ethyl; R² is:

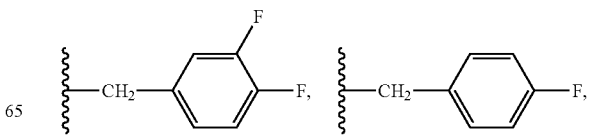

R³ is:

-continued

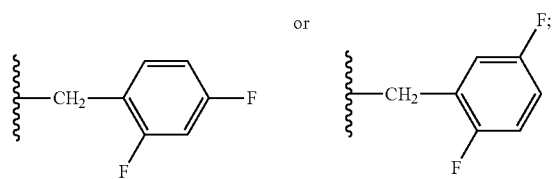

and each occurrence of R⁴ is independently H, methyl or isopropyl.

In another embodiment, $R^1$ is methyl or ethyl; $R^2$ is:

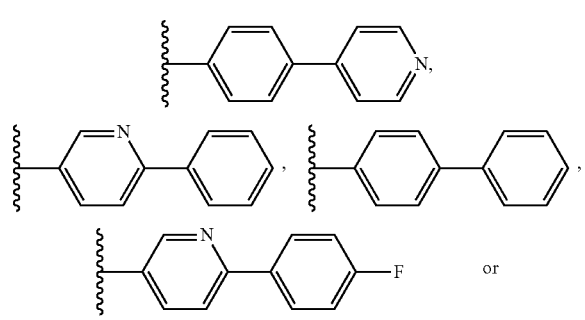

$R^3$ is:

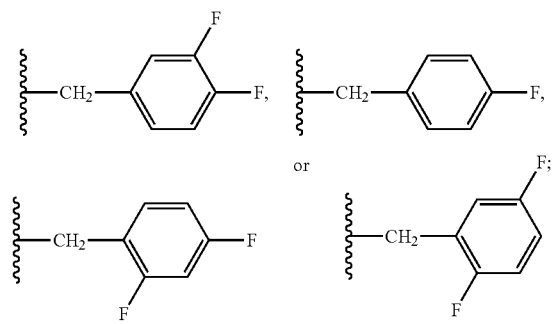

and each occurrence of $R^4$ is methyl.

In another embodiment, $R^1$ is methyl or ethyl; $R^2$ is:

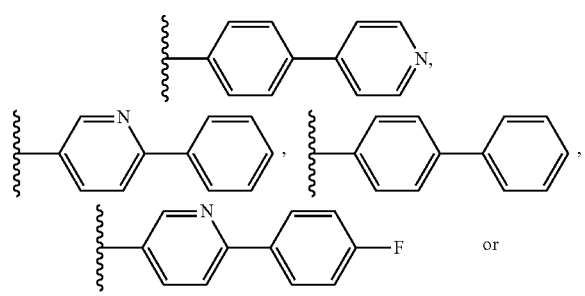

-continued

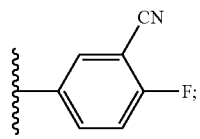

$R^3$ is:

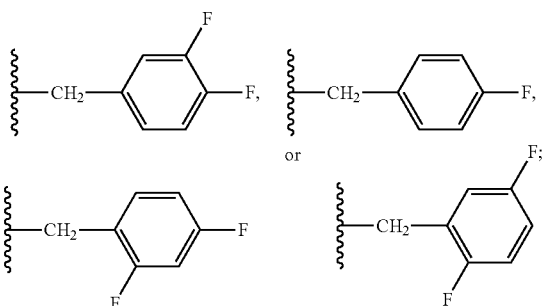

and one occurrence of $R^4$ is H, and the other occurrence of $R^4$ is isopropyl.

In another embodiment, $R^1$ is ethyl; $R^2$ is:

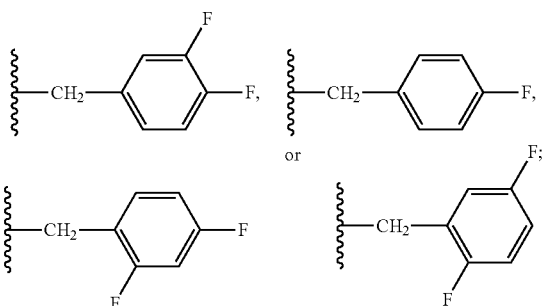

$R^3$ is:

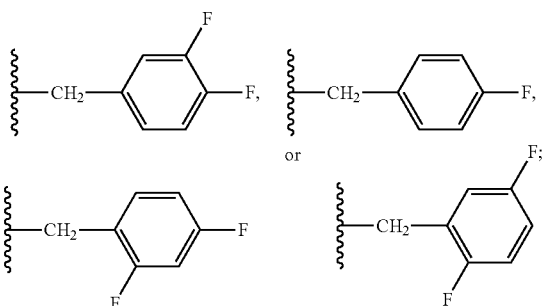

and each occurrence of $R^4$ is independently H, methyl or isopropyl.

In another embodiment, $R^1$ is ethyl; $R^2$ is:

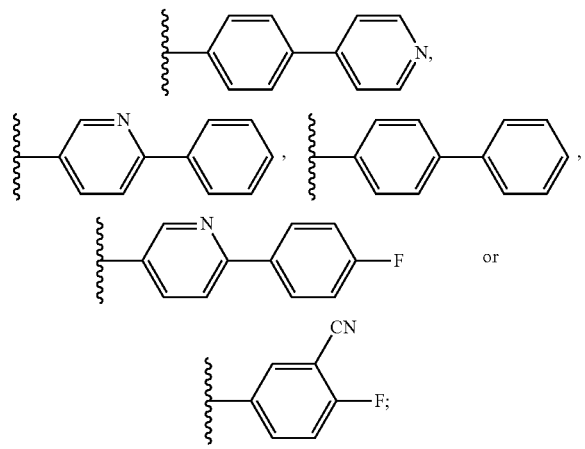

$R^3$ is:

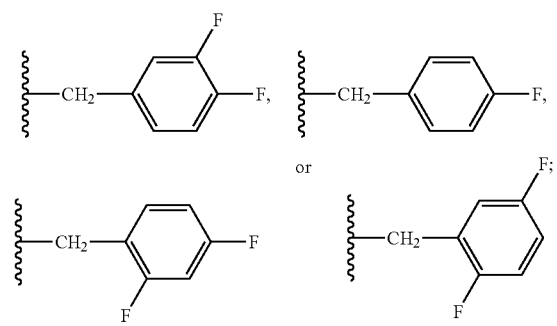

and one occurrence of $R^4$ is H, and the other occurrence of $R^4$ is isopropyl.

In another embodiment, $R^1$ is methyl or ethyl; $R^2$ is:

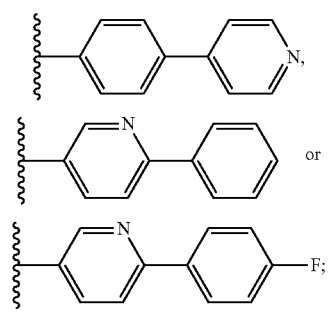

$R^3$ is:

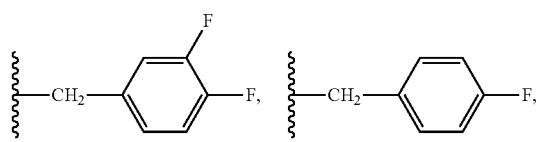

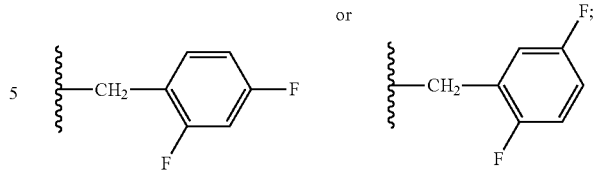

and each occurrence of $R^4$ is independently H, methyl or isopropyl.

In another embodiment, $R^1$ is methyl or ethyl; $R^2$ is:

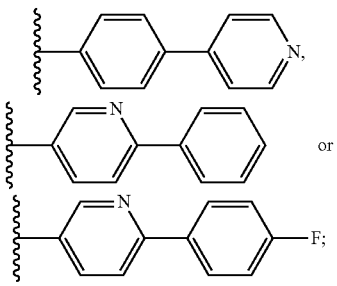

$R^3$ is:

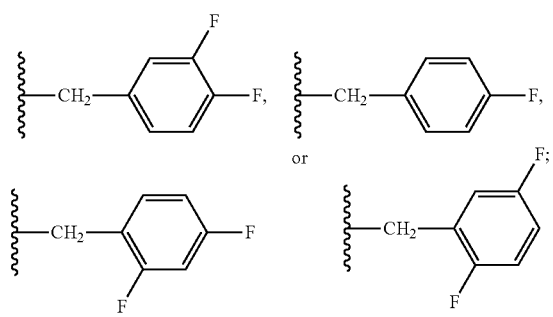

and each occurrence of $R^4$ is methyl.

In another embodiment, $R^1$ is methyl or ethyl; $R^2$ is:

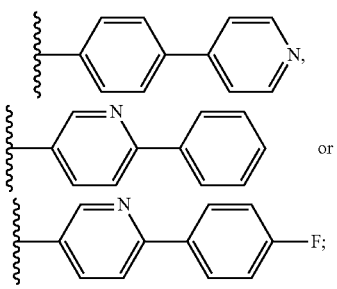

$R^3$ is:

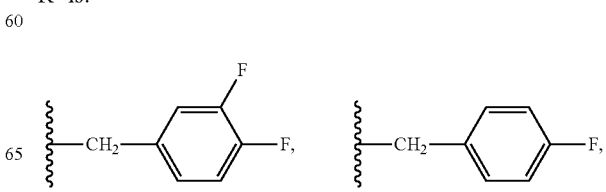

-continued

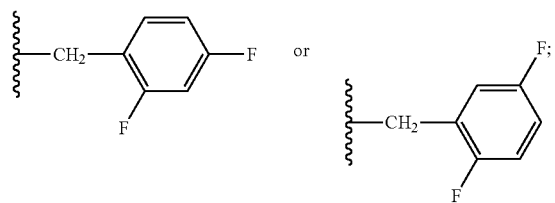 or and one occurrence of R⁴ is H, and the other occurrence of R⁴ is isopropyl.

In another embodiment, R¹ is ethyl; R² is:

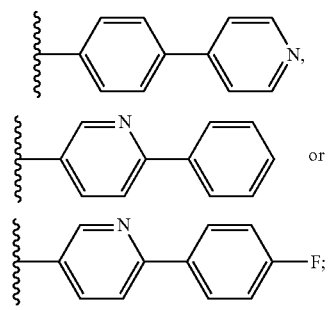

R³ is:

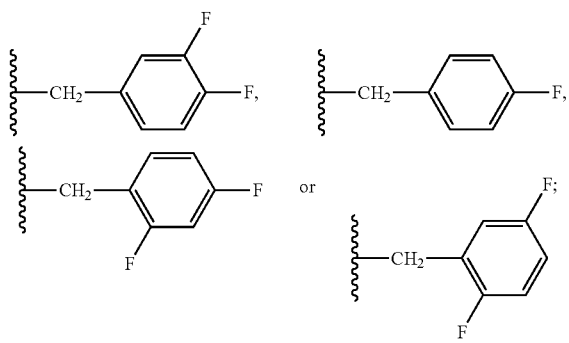

and each occurrence of R⁴ is independently H, methyl or isopropyl.

In another embodiment, R¹ is ethyl; R² is:

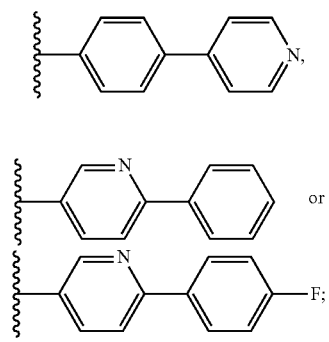

R³ is:

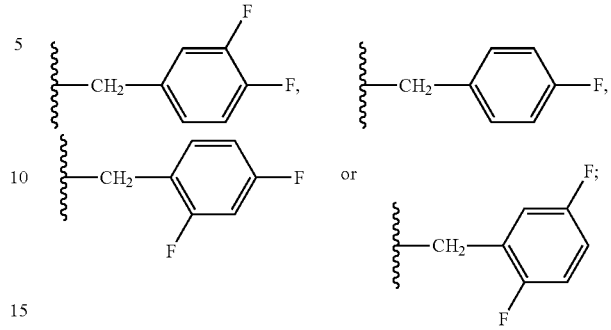

and one occurrence of R⁴ is H, and the other occurrence of R⁴ is isopropyl.

In one embodiment, for the Compounds of Formula (Ia), variables R¹, R², R³ and R⁴ are selected independently of each other.

In another embodiment, a compound of formula (Ia) is in purified form.

In another embodiment, a compound of formula (Ia) can be an antagonist of $P2X_7$.

The Polycyclic Guanine Derivatives of Formula (II)

In another embodiment, the present invention provides Polycyclic Guanine Derivatives of Formula (II):

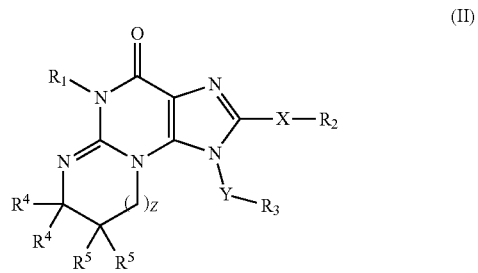

(II)

and pharmaceutically acceptable salts, solvates, esters and prodrugs thereof, wherein X, Y, R¹, R², R³, R⁴, R⁵ and z are defined above for the Compounds of Formula (II).

In one embodiment z is 0. In another embodiment, z is 1.

In one embodiment, X is absent

In another embodiment, X is arylene.

In another embodiment, X is alkylene.

In still another embodiment, X is alkenylene.

In another embodiment, X is alkynylene.

In another embodiment, X is cycloalkylene.

In another embodiment, X is heterocycloalkylene.

In still another embodiment, X is heteroarylene.

In yet another embodiment, X is —S—.

In one embodiment, X is —NH—.

In another embodiment, X is —O—.

In another embodiment, X is —CH₂—.

In another embodiment, X is —CH₂CH₂—.

In another embodiment, X is —C≡C—.
In still another embodiment, X is:

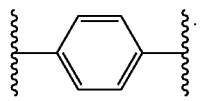 [SMILES: *c1ccc(*)cc1]

In yet another embodiment, X is:

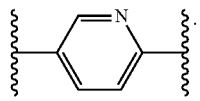 [SMILES: *c1ccc(*)nc1]

In a further embodiment, X is:

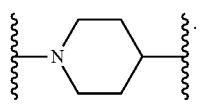 [SMILES: *C1CCN(*)CC1]

In another embodiment, X is:

In one embodiment, Y is absent
In another embodiment, Y is arylene.
In another embodiment, Y is alkylene.
In still another embodiment, Y is alkenylene.
In another embodiment, Y is alkynylene.
In another embodiment, Y is cycloalkylene.
In another embodiment, Y is heterocycloalkylene.
In still another embodiment, Y is heteroarylene.
In yet another embodiment, Y is —S—.
In one embodiment, Y is —NH—.
In another embodiment, Y is —O—.
In another embodiment, Y is —CH$_2$—.
In still another embodiment, Y is:

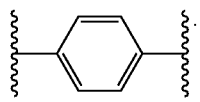 [SMILES: *c1ccc(*)cc1]

In one embodiment, R$^1$ is alkyl.
In another embodiment, R$^1$ is -alkylene-N(R$^7$)$_2$.
In still another embodiment, R$^1$ is aryl.
In yet another embodiment, R$^1$ is cycloalkyl.
In one embodiment, R$^1$ is heteroaryl.
In another embodiment, R$^1$ is heterocycloalkyl.
In another embodiment, R$^1$ is hydroxyalkyl.
In still another embodiment, R$^1$ is haloalkyl.
In a further embodiment, R$^1$ is -alkyene-alkoxy.
In one embodiment, R$^1$ is —C$_1$-C$_6$ alkyl.
In another embodiment, R$^1$ is methyl.
In still another embodiment, R$^1$ is ethyl.
In still another embodiment, R$^1$ is -alkylene-aryl.
In yet another embodiment, R$^1$ is -alkylene-cycloalkyl.

In one embodiment, R$^1$ is -alkylene-heteroaryl.
In another embodiment, R$^1$ is -alkylene-heterocycloalkyl.
In one embodiment, R$^2$ is H
In another embodiment, R$^2$ is alkyl
In another embodiment, R$^2$ is heteroaryl.
In yet another embodiment, R$^2$ is cycloalkyl.
In another embodiment, R$^2$ is heterocycloalkyl.
In a further embodiment, R$^2$ is aryl.
In another embodiment, R$^2$ is hydroxyalkyl.
In another embodiment, R$^2$ is haloalkyl.
In another embodiment, R$^2$ is —N(R$^7$)$_2$.
In still another embodiment, R$^2$ is phenyl.
In still another embodiment, R$^2$ is pyridyl.
In another embodiment, R$^2$ is furazanyl.
In another embodiment, R$^2$ is imidazolyl.
In another embodiment, R$^2$ is 4-fluoropyridyl,

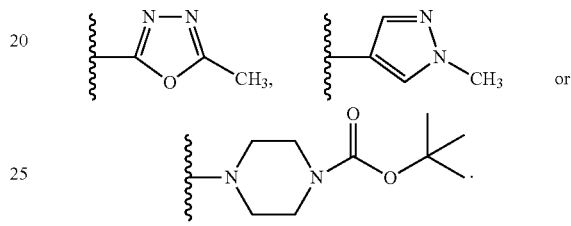

In one embodiment, X is absent and R$^2$ is phenyl, which can be optionally substituted with R$^6$.
In another embodiment, —X—R$^2$ is benzyl, which can be optionally substituted with R$^6$.
In another embodiment, X is absent and R$^2$ is pyridyl, which can be optionally substituted with R$^6$.
In another embodiment, X is absent and R$^2$ is piperidinyl or piperazinyl, which are optionally substituted with R$^6$.
In one embodiment, —X—R$^2$ is:

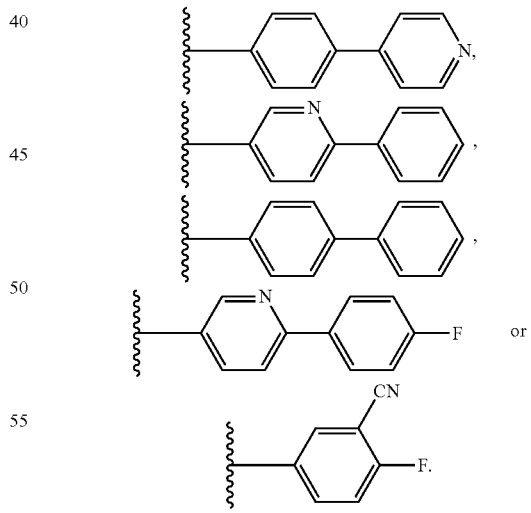

In another embodiment, —X—R$^2$ is:

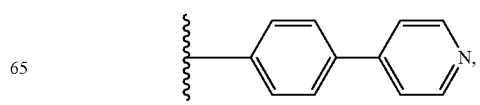

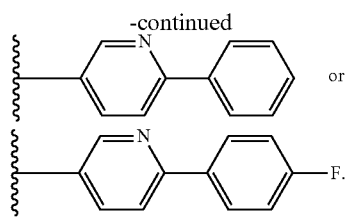

In one embodiment, $R^3$ is H.
In another embodiment, $R^3$ is alkyl.
In another embodiment, $R^3$ is heteroaryl.
In yet another embodiment, $R^3$ is cycloalkyl.
In another embodiment, $R^3$ is heterocycloalkyl.
In a further embodiment, $R^3$ is aryl.
In another embodiment, $R^3$ is hydroxyalkyl.
In another embodiment, $R^3$ is haloalkyl.
In another embodiment, $R^3$ is $-N(R^7)_2$.
In another embodiment, $R^3$ is phenyl.
In another embodiment, $R^3$ is cyclobutyl.
In another embodiment, $R^3$ is cyclopentyl.
In still another embodiment, $R^3$ is cyclohexyl.
In yet another embodiment, $R^3$ is tetrahydrofuranyl.
In one embodiment, $-X-R^3$ is alkylene-aryl.
In another embodiment, $-X-R^3$ is -alkylene-cycloalkyl.
In another embodiment, $-X-R^3$ is $-CH_2$-aryl.
In still another embodiment, $-X-R^3$ is $-CH_2$-phenyl, wherein the phenyl group can be optionally substituted with $R^7$.
In another embodiment, $-X-R^3$ is $-CH_2$-phenyl, wherein the phenyl group is substituted with one or two F atoms.
In another embodiment, $-X-R^3$ is $-CH_2$-phenyl, wherein the phenyl group is monosubstituted with one F atom.
In another embodiment, $-X-R^3$ is $-CH_2$-phenyl, wherein the phenyl group is disubstituted with two F atoms.
In one embodiment, $-X-R^3$ is:

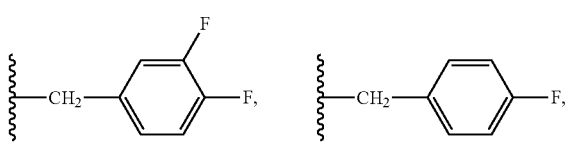

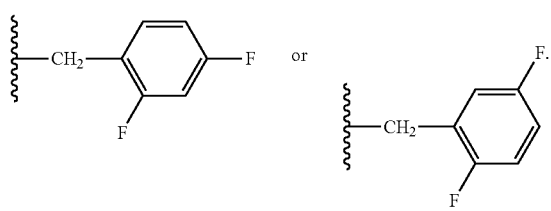

In one embodiment, each occurrence of $R^4$ is independently H or $-C_1-C_6$ alkyl.

In another embodiment, each occurrence of $R^4$ is independently H, methyl, isopropyl, sec-butyl or t-butyl.

In another embodiment, one occurrence of $R^4$ is H and the other is $-C_1-C_6$ alkyl.

In still another embodiment, one occurrence of $R^4$ is H and the other is methyl, isopropyl, sec-butyl or t-butyl.

In yet another embodiment, one occurrence of $R^4$ is H and the other is isopropyl.

In another embodiment, each occurrence of $R^4$ is $-C_1-C_6$ alkyl.

In still another embodiment, each occurrence of $R^4$ is methyl.

In one embodiment, one occurrence of $R^4$ is H and the other is cycloalkyl.

In another embodiment, one occurrence of $R^4$ is H and the other is cyclopropyl.

In one embodiment, both $R^4$ groups, together with the carbon atom to which they are attached, join to form a 3- to 7-membered cycloalkyl group.

In another embodiment, both $R^4$ groups, together with the carbon atom to which they are attached, join to form a 5-membered cycloalkyl group.

In another embodiment, both $R^4$ groups, together with the carbon atom to which they are attached, join to form a 6-membered cycloalkyl group.

In still another embodiment, both $R^4$ groups, together with the carbon atom to which they are attached, join to form a 5-membered cycloalkyl group which is fused to a benzene ring.

In yet another embodiment, both $R^4$ groups, together with the carbon atom to which they are attached, join to form a 6-membered cycloalkyl group which is fused to a benzene ring.

In one embodiment, a compound of formula (II) is a compound of formula (I) and it is to be understood that when a compound of formula (II) is a compound of formula (I), all embodiments listed above for the Compounds of Formula (I) also apply.

In one embodiment, for the Compounds of Formula (II), variables $R^1$, $R^2$, $R^3$, $R^4$ and $R^5$ are selected independently of each other.

In another embodiment, a compound of formula (II) is in purified form.

In another embodiment, a compound of formula (II) can be an antagonist of $P2X_7$.

Non-limiting examples of the Polycyclic Guanine Derivatives of the present invention include the following compounds:

| No. | Structure |
|---|---|
| 1 | 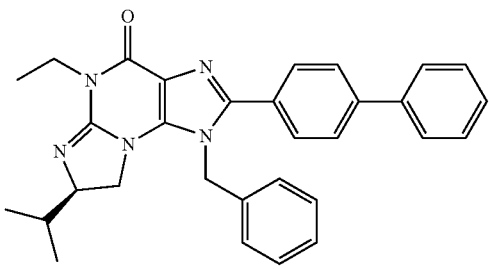 [SMILES: CCN1C(=O)c2nc(-c3ccc(-c4ccccc4)cc3)n(Cc3ccccc3)c2N2C[C@@H](C(C)C)N=C12] |
| 2 | 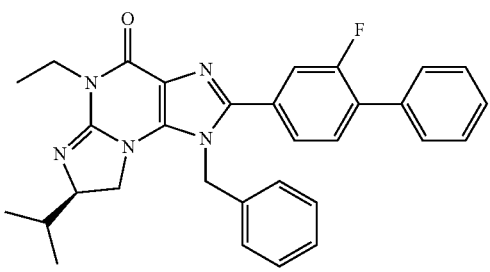 [SMILES: CCN1C(=O)c2nc(-c3ccc(-c4ccccc4)c(F)c3)n(Cc3ccccc3)c2N2C[C@@H](C(C)C)N=C12] |
| 3 | 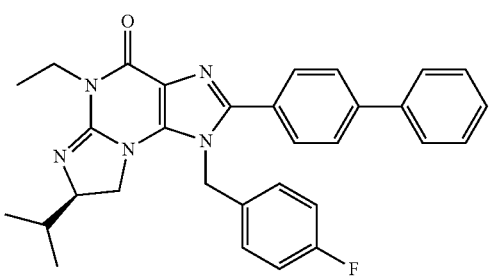 [SMILES: CCN1C(=O)c2nc(-c3ccc(-c4ccccc4)cc3)n(Cc3ccc(F)cc3)c2N2C[C@@H](C(C)C)N=C12] |
| 4 | 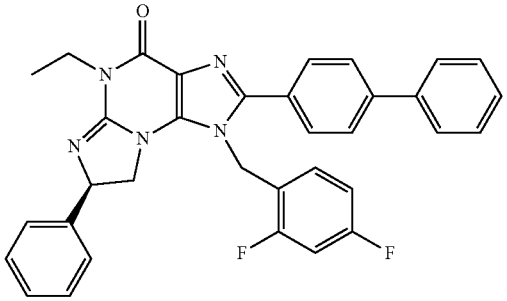 [SMILES: CCN1C(=O)c2nc(-c3ccc(-c4ccccc4)cc3)n(Cc3ccc(F)cc3F)c2N2C[C@@H](c3ccccc3)N=C12] |
| 5 | 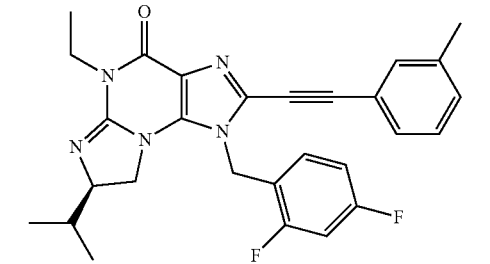 [SMILES: CCN1C(=O)c2nc(C#Cc3cccc(C)c3)n(Cc3ccc(F)cc3F)c2N2C[C@@H](C(C)C)N=C12] |

-continued
| No. | Structure |
|---|---|
| 6 | 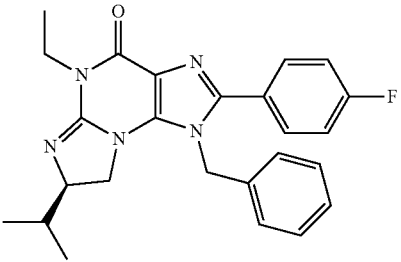 [SMILES: CCN1C(=O)c2nc(-c3ccc(F)cc3)n(Cc3ccccc3)c2N2C[C@@H](C(C)C)N=C12] |
| 7 | 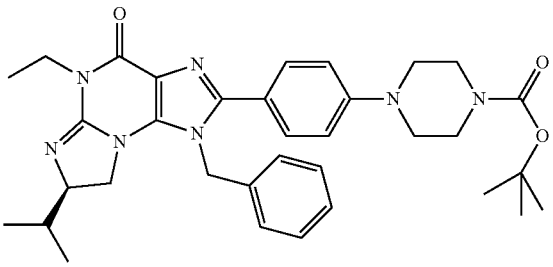 [SMILES: CCN1C(=O)c2nc(-c3ccc(N4CCN(C(=O)OC(C)(C)C)CC4)cc3)n(Cc3ccccc3)c2N2C[C@@H](C(C)C)N=C12] |
| 8 | 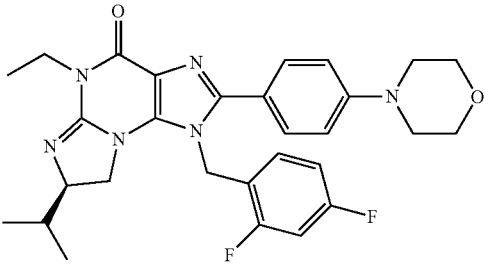 [SMILES: CCN1C(=O)c2nc(-c3ccc(N4CCOCC4)cc3)n(Cc3ccc(F)cc3F)c2N2C[C@@H](C(C)C)N=C12] |
| 9 | 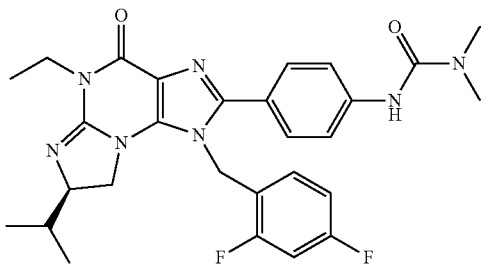 [SMILES: CCN1C(=O)c2nc(-c3ccc(NC(=O)N(C)C)cc3)n(Cc3ccc(F)cc3F)c2N2C[C@@H](C(C)C)N=C12] |
| 10 | 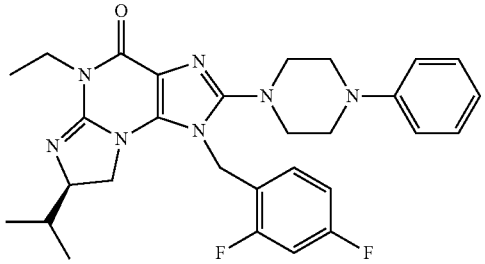 [SMILES: CCN1C(=O)c2nc(N3CCN(c4ccccc4)CC3)n(Cc3ccc(F)cc3F)c2N2C[C@@H](C(C)C)N=C12] |

| No. | Structure |
|---|---|
| 11 | 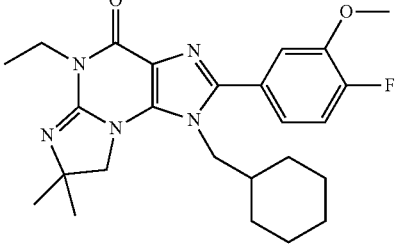 |
| 12 | 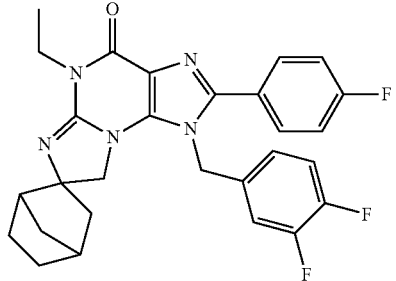 [SMILES: CCN1C(=O)c2nc(-c3ccc(F)cc3)n(Cc3ccc(F)c(F)c3)c2N2CC3(CC4CCC3C4)N=C12] |
| 13 | 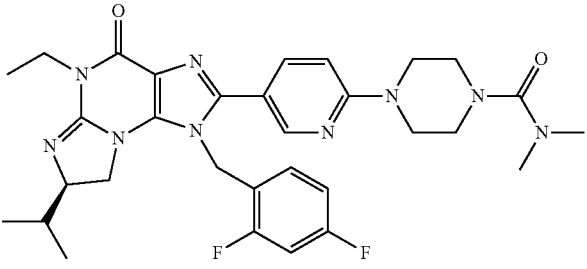 [SMILES: CCN1C(=O)c2nc(-c3ccc(N4CCN(C(=O)N(C)C)CC4)nc3)n(Cc3ccc(F)cc3F)c2N2C[C@@H](C(C)C)N=C12] |
| 14 | 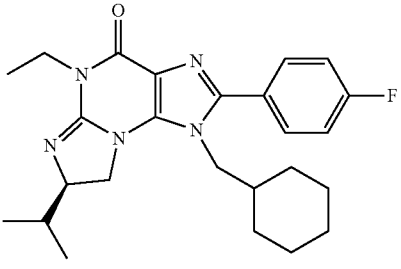 [SMILES: CCN1C(=O)c2nc(-c3ccc(F)cc3)n(CC3CCCCC3)c2N2C[C@@H](C(C)C)N=C12] |
| 15 | 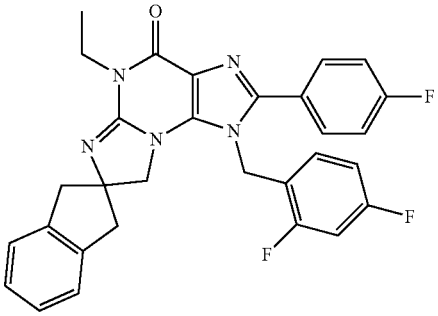 [SMILES: CCN1C(=O)c2nc(-c3ccc(F)cc3)n(Cc3ccc(F)cc3F)c2N2CC3(Cc4ccccc4C3)N=C12] |

-continued
| No. | Structure |
|---|---|
| 16 | 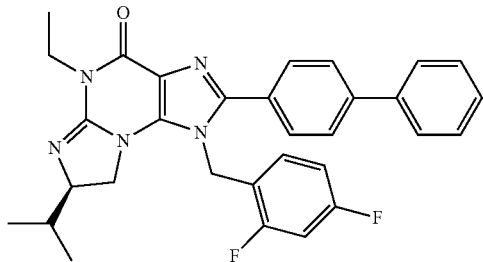 [SMILES: CCN1C(=O)c2nc(-c3ccc(-c4ccccc4)cc3)n(Cc3ccc(F)cc3F)c2N2C[C@@H](C(C)C)N=C12] |
| 17 | 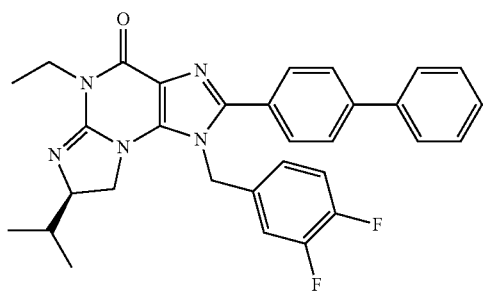 [SMILES: CCN1C(=O)c2nc(-c3ccc(-c4ccccc4)cc3)n(Cc3ccc(F)c(F)c3)c2N2C[C@@H](C(C)C)N=C12] |
| 18 | 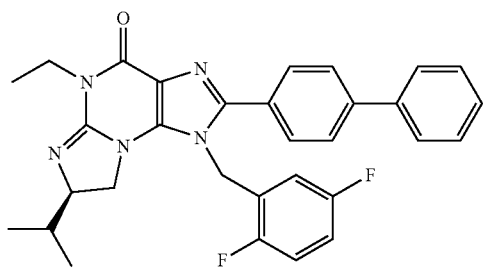 [SMILES: CCN1C(=O)c2nc(-c3ccc(-c4ccccc4)cc3)n(Cc3cc(F)ccc3F)c2N2C[C@@H](C(C)C)N=C12] |
| 19 | 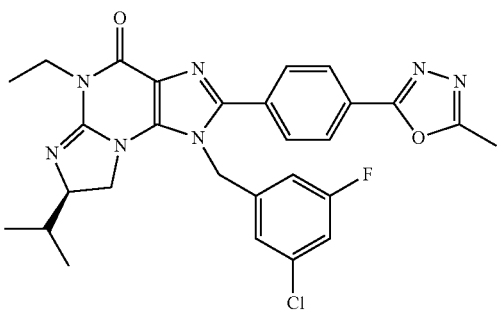 [SMILES: CCN1C(=O)c2nc(-c3ccc(-c4nnc(C)o4)cc3)n(Cc3cc(F)cc(Cl)c3)c2N2C[C@@H](C(C)C)N=C12] |
| 20 | 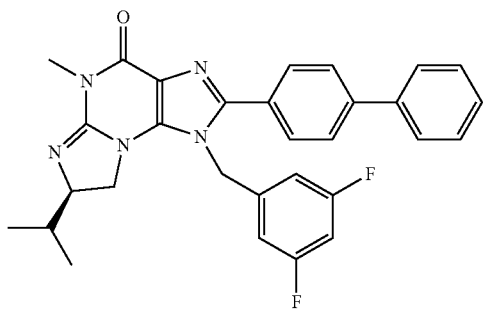 [SMILES: CC(C)[C@@H]1CN2C(=N1)N(C)C(=O)c1nc(-c3ccc(-c4ccccc4)cc3)n(Cc3cc(F)cc(F)c3)c12] |

-continued
| No. | Structure |
|---|---|
| 21 | 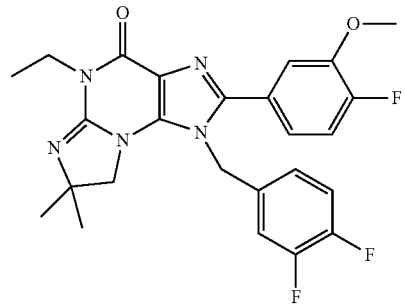 [SMILES: CCN1C(=O)c2nc(-c3ccc(F)c(OC)c3)n(Cc3ccc(F)c(F)c3)c2N2CC(C)(C)N=C12] |
| 22 | 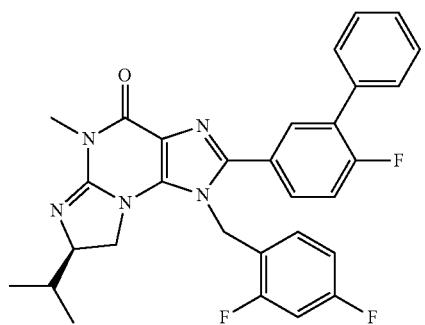 [SMILES: CC(C)[C@@H]1CN2C(=N1)N(C)C(=O)c1nc(-c3ccc(F)c(-c4ccccc4)c3)n(Cc3ccc(F)cc3F)c12] |
| 23 | 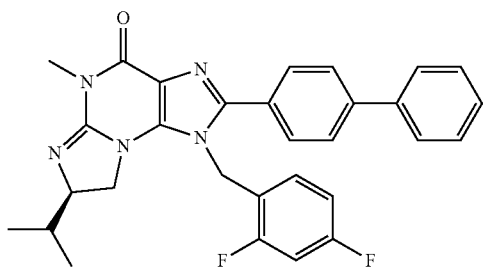 [SMILES: CC(C)[C@@H]1CN2C(=N1)N(C)C(=O)c1nc(-c3ccc(-c4ccccc4)cc3)n(Cc3ccc(F)cc3F)c12] |
| 24 | 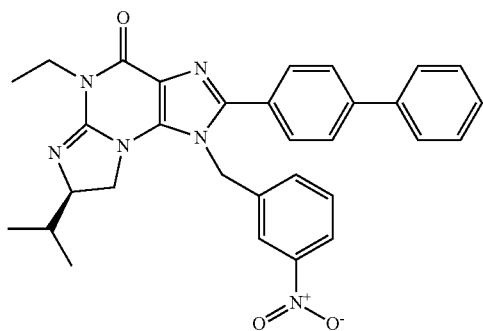 [SMILES: CCN1C(=O)c2nc(-c3ccc(-c4ccccc4)cc3)n(Cc3cccc([N+](=O)[O-])c3)c2N2C[C@@H](C(C)C)N=C12] |
| 25 | 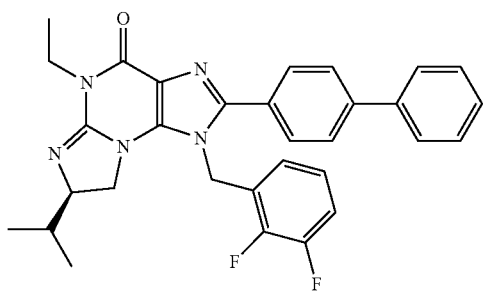 [SMILES: CCN1C(=O)c2nc(-c3ccc(-c4ccccc4)cc3)n(Cc3cccc(F)c3F)c2N2C[C@@H](C(C)C)N=C12] |

-continued
| No. | Structure |
|---|---|
| 26 | 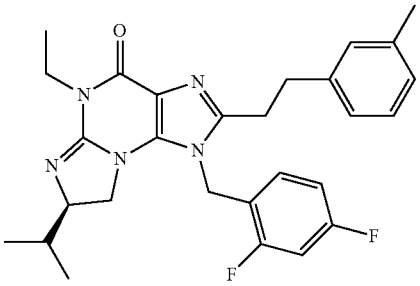 [SMILES: CCN1C(=O)c2nc(CCc3cccc(C)c3)n(Cc3ccc(F)cc3F)c2N2C[C@@H](C(C)C)N=C12] |
| 27 | 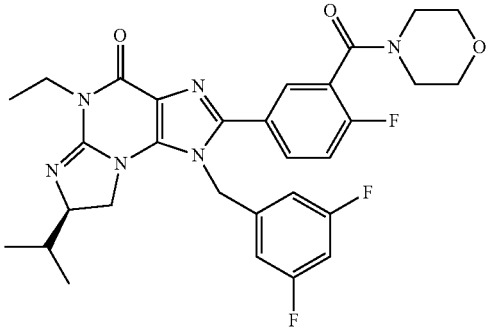 [SMILES: CCN1C(=O)c2nc(-c3ccc(F)c(C(=O)N4CCOCC4)c3)n(Cc3cc(F)cc(F)c3)c2N2C[C@@H](C(C)C)N=C12] |
| 28 | 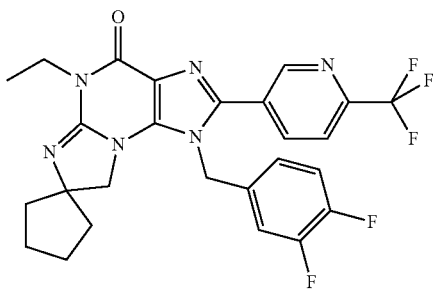 [SMILES: CCN1C(=O)c2nc(-c3ccc(C(F)(F)F)nc3)n(Cc3ccc(F)c(F)c3)c2N2CC3(CCCC3)N=C12] |
| 29 | 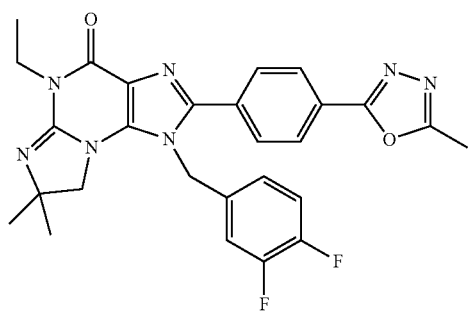 |
| 30 | 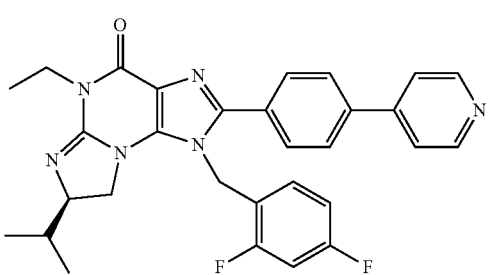 [SMILES: CCN1C(=O)c2nc(-c3ccc(-c4ccncc4)cc3)n(Cc3ccc(F)cc3F)c2N2C[C@@H](C(C)C)N=C12] |

-continued
| No. | Structure |
|---|---|
| 31 | 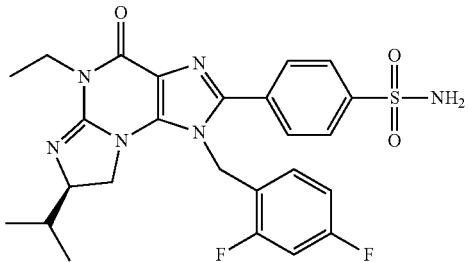 [SMILES: CCN1C(=O)c2nc(-c3ccc(S(N)(=O)=O)cc3)n(Cc3ccc(F)cc3F)c2N2C[C@@H](C(C)C)N=C12] |
| 32 | 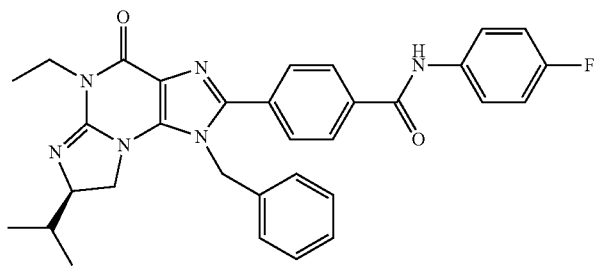 [SMILES: CCN1C(=O)c2nc(-c3ccc(C(=O)Nc4ccc(F)cc4)cc3)n(Cc3ccccc3)c2N2C[C@@H](C(C)C)N=C12] |
| 33 | 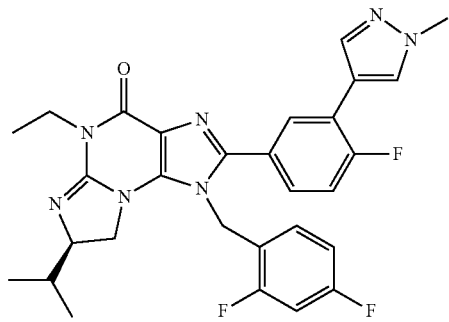 [SMILES: CCN1C(=O)c2nc(-c3ccc(F)c(-c4cnn(C)c4)c3)n(Cc3ccc(F)cc3F)c2N2C[C@@H](C(C)C)N=C12] |
| 34 | 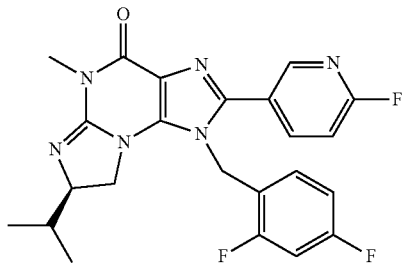 [SMILES: CC(C)[C@@H]1CN2C(=N1)N(C)C(=O)c1nc(-c3ccc(F)nc3)n(Cc3ccc(F)cc3F)c12] |
| 35 | 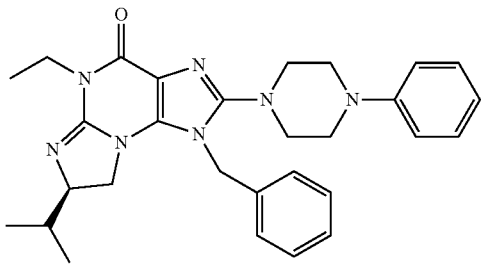 [SMILES: CCN1C(=O)c2nc(N3CCN(c4ccccc4)CC3)n(Cc3ccccc3)c2N2C[C@@H](C(C)C)N=C12] |

-continued
| No. | Structure |
|---|---|
| 36 | 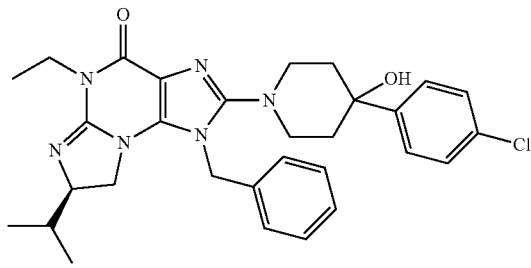 [SMILES: CCN1C(=O)c2nc(N3CCC(O)(c4ccc(Cl)cc4)CC3)n(Cc3ccccc3)c2N2C[C@@H](C(C)C)N=C12] |
| 37 | 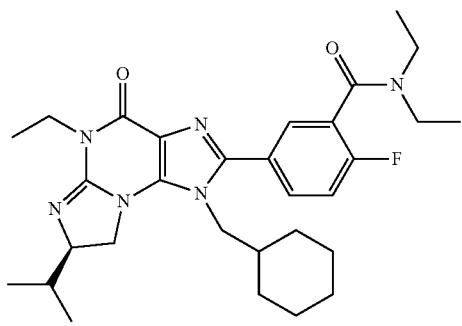 [SMILES: CCN(CC)C(=O)c1cc(-c2nc3c(n2CC2CCCCC2)N2C[C@@H](C(C)C)N=C2N(CC)C3=O)ccc1F] |
| 38 | 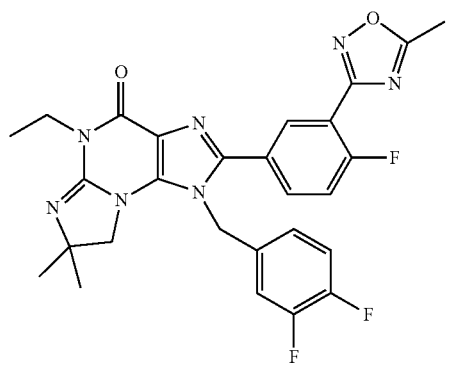 [SMILES: CCN1C(=O)c2nc(-c3ccc(F)c(-c4noc(C)n4)c3)n(Cc3ccc(F)c(F)c3)c2N2CC(C)(C)N=C12] |
| 39 | 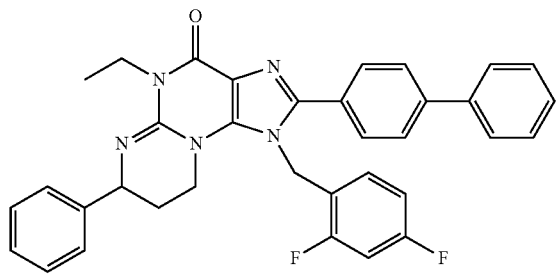 [SMILES: CCN1C(=O)c2nc(-c3ccc(-c4ccccc4)cc3)n(Cc3ccc(F)cc3F)c2N2CCC(c3ccccc3)N=C12] |
| 40 | 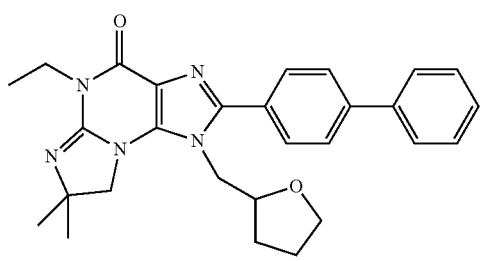 [SMILES: CCN1C(=O)c2nc(-c3ccc(-c4ccccc4)cc3)n(CC3CCCO3)c2N2CC(C)(C)N=C12] |

-continued
| No. | Structure |
|---|---|
| 41 | 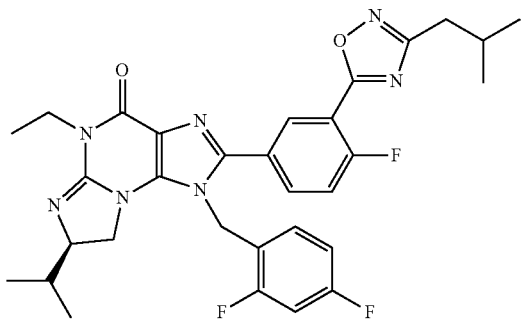 [SMILES: CCN1C(=O)c2nc(-c3ccc(F)c(-c4nc(CC(C)C)no4)c3)n(Cc3ccc(F)cc3F)c2N2C[C@@H](C(C)C)N=C12] |
| 42 | 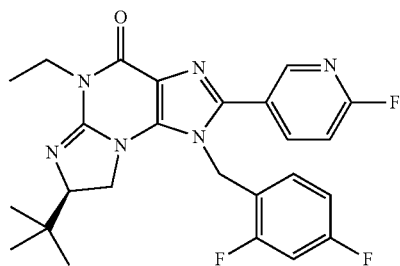 [SMILES: CCN1C(=O)c2nc(-c3ccc(F)nc3)n(Cc3ccc(F)cc3F)c2N2C[C@@H](C(C)(C)C)N=C12] |
| 43 | 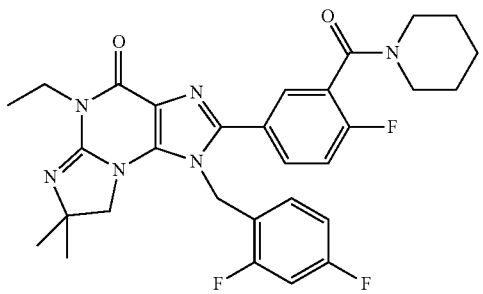 [SMILES: CCN1C(=O)c2nc(-c3ccc(F)c(C(=O)N4CCCCC4)c3)n(Cc3ccc(F)cc3F)c2N2CC(C)(C)N=C12] |
| 44 | 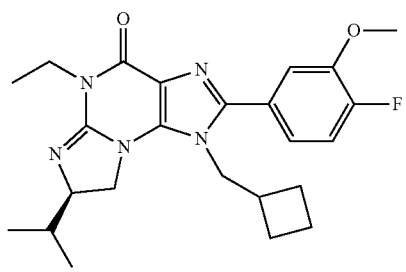 [SMILES: CCN1C(=O)c2nc(-c3ccc(F)c(OC)c3)n(CC3CCC3)c2N2C[C@@H](C(C)C)N=C12] |

45
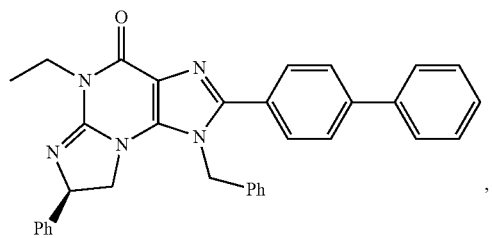
46
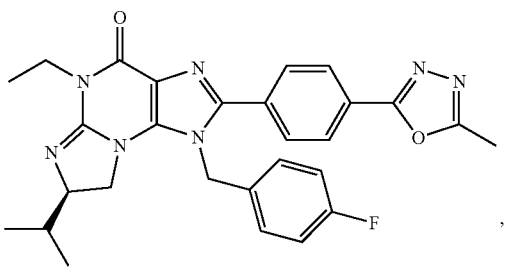
47
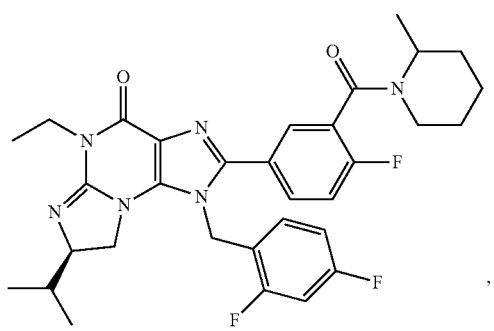
48
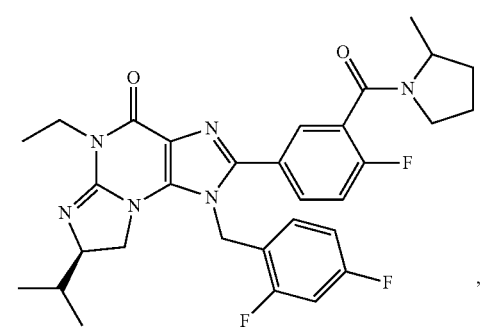
49
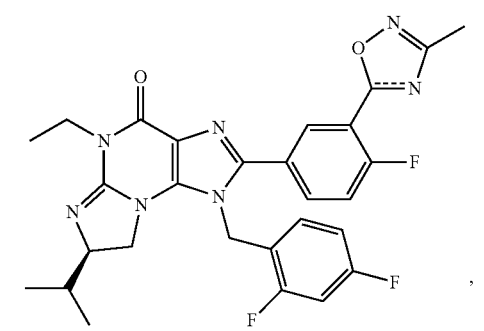
50
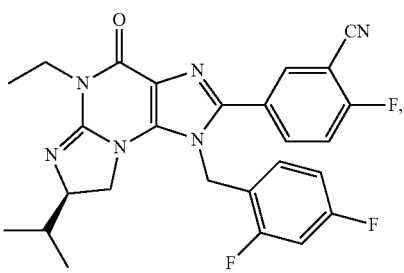
51
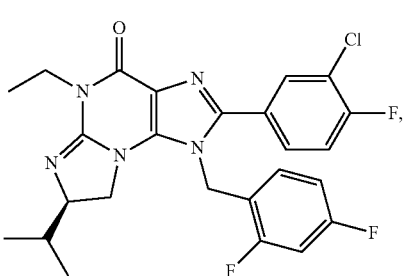
52
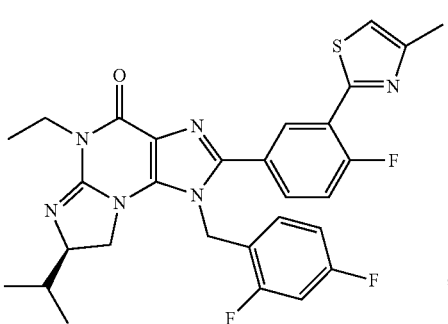
53
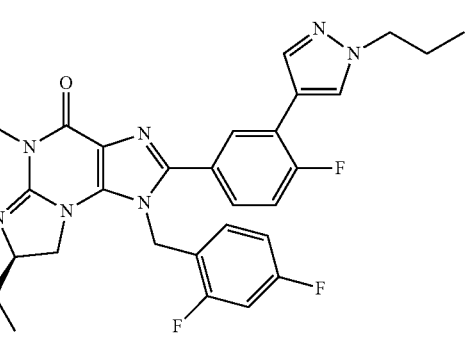
54
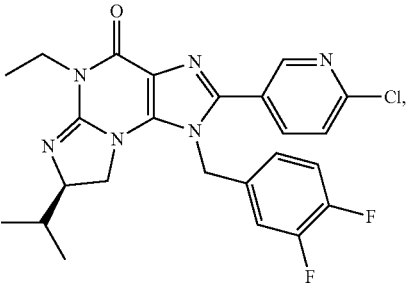

61
-continued
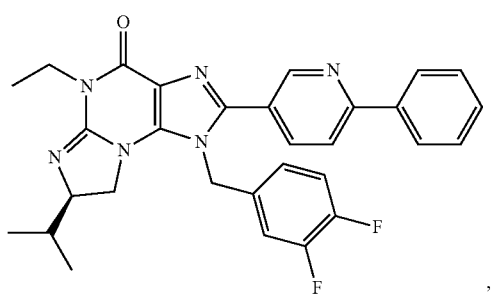
62
-continued
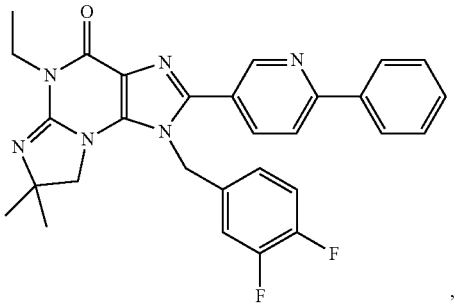
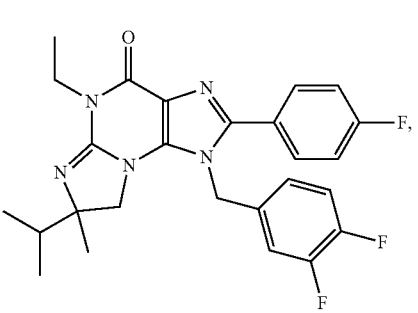
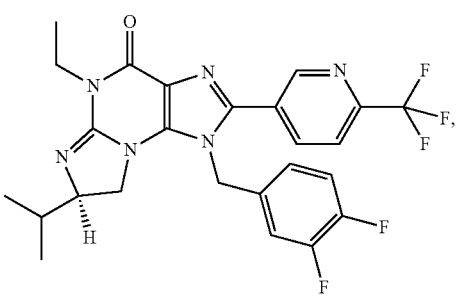
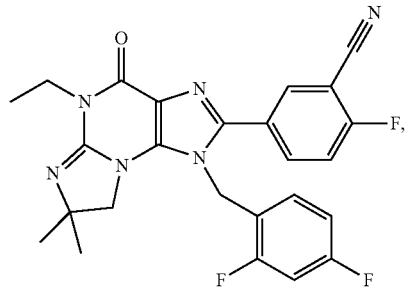
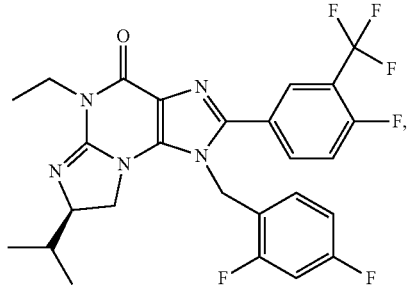

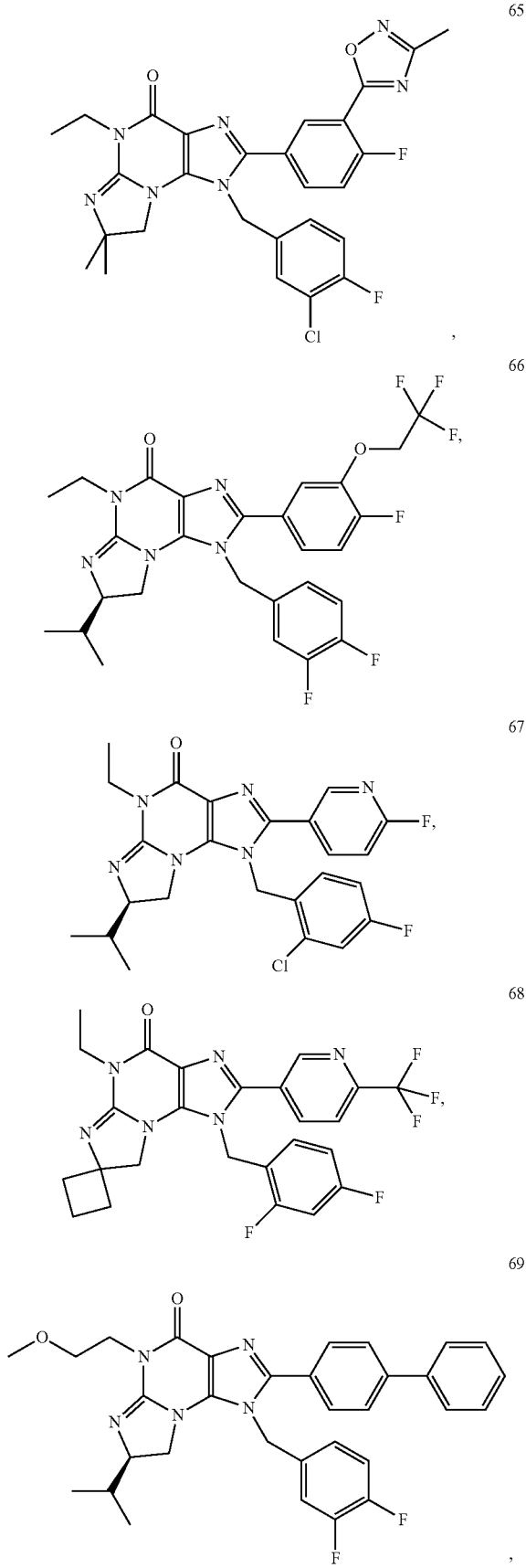
and pharmaceutically acceptable salts, solvates, esters and prodrugs thereof.
Additional illustrative examples of the Polycyclic Guanine Derivatives of the present invention include, but are not limited to, the following compounds:

| No. | Structure |
|---|---|
| 74 | 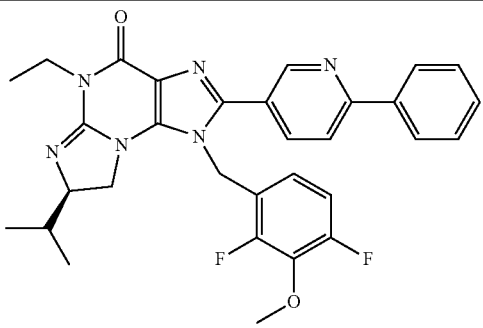 |
| 75 | 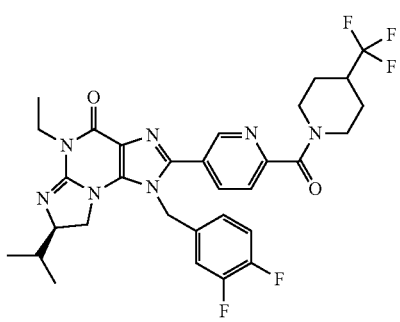 [SMILES: CCN1C(=O)c2nc(-c3ccc(C(=O)N4CCC(C(F)(F)F)CC4)nc3)n(Cc3ccc(F)c(F)c3)c2N2C[C@@H](C(C)C)N=C12] |
| 76 | 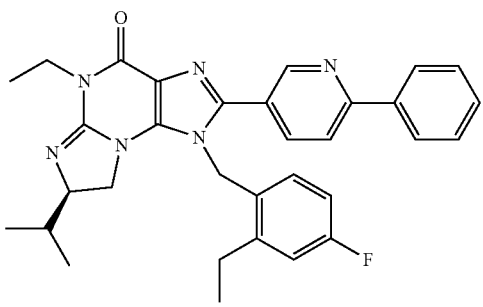 [SMILES: CCc1cc(F)ccc1Cn1c(-c2ccc(-c3ccccc3)nc2)nc2c1N1C[C@@H](C(C)C)N=C1N(CC)C2=O] |
| 77 | 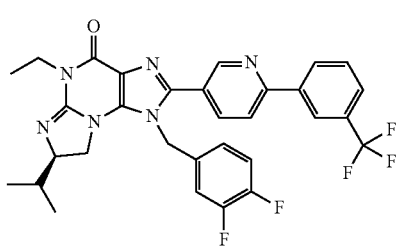 [SMILES: CCN1C(=O)c2nc(-c3ccc(-c4cccc(C(F)(F)F)c4)nc3)n(Cc3ccc(F)c(F)c3)c2N2C[C@@H](C(C)C)N=C12] |
-continued
| No. | Structure |
|---|---|
| 78 | 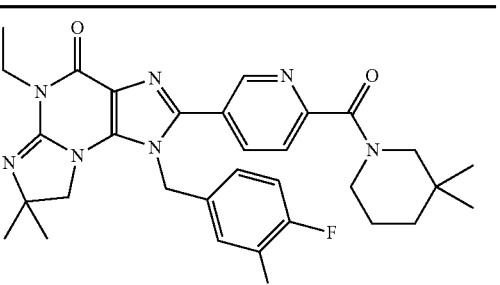 |
| 79 | 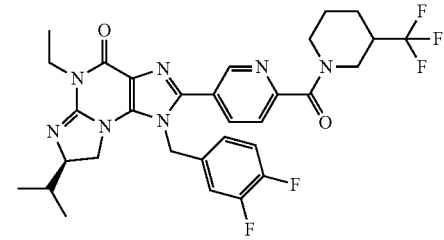 [SMILES: CCN1C(=O)c2nc(-c3ccc(C(=O)N4CCCC(C(F)(F)F)C4)nc3)n(Cc3ccc(F)c(F)c3)c2N2C[C@@H](C(C)C)N=C12] |
| 80 | 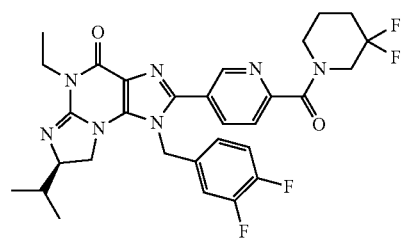 [SMILES: CCN1C(=O)c2nc(-c3ccc(C(=O)N4CCCC(F)(F)C4)nc3)n(Cc3ccc(F)c(F)c3)c2N2C[C@@H](C(C)C)N=C12] |
| 81 | 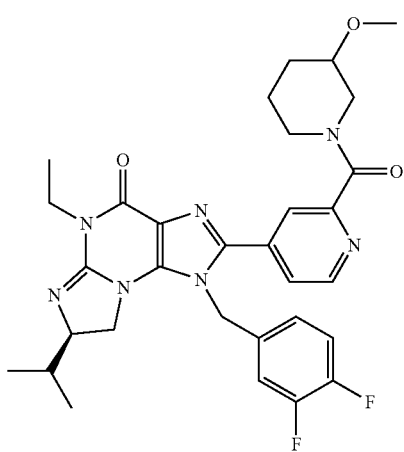 [SMILES: CCN1C(=O)c2nc(-c3ccnc(C(=O)N4CCCC(OC)C4)c3)n(Cc3ccc(F)c(F)c3)c2N2C[C@@H](C(C)C)N=C12] |

| No. | Structure |
|---|---|
| 82 | 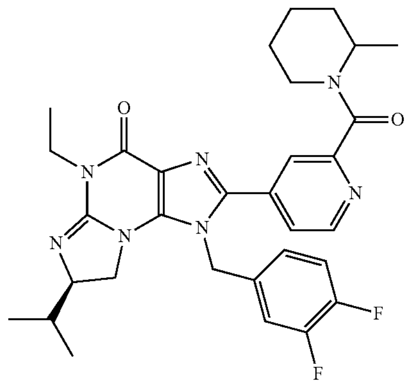 [SMILES: CCN1C(=O)c2nc(-c3ccnc(C(=O)N4CCCCC4C)c3)n(Cc3ccc(F)c(F)c3)c2N2C[C@@H](C(C)C)N=C12] |
| 83 | 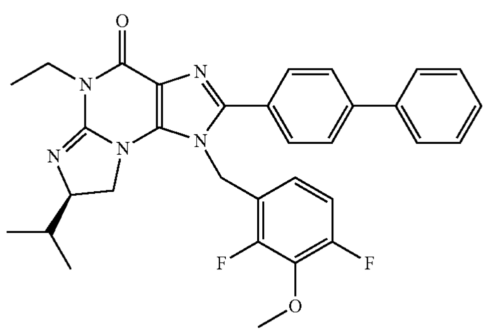 [SMILES: CCN1C(=O)c2nc(-c3ccc(-c4ccccc4)cc3)n(Cc3ccc(F)c(OC)c3F)c2N2C[C@@H](C(C)C)N=C12] |
| 84 | 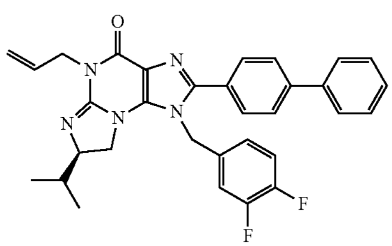 [SMILES: C=CCN1C(=O)c2nc(-c3ccc(-c4ccccc4)cc3)n(Cc3ccc(F)c(F)c3)c2N2C[C@@H](C(C)C)N=C12] |
| 85 | 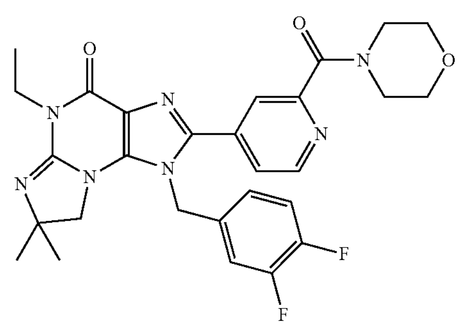 [SMILES: CCN1C(=O)c2nc(-c3ccnc(C(=O)N4CCOCC4)c3)n(Cc3ccc(F)c(F)c3)c2N2CC(C)(C)N=C12] |
| 86 | 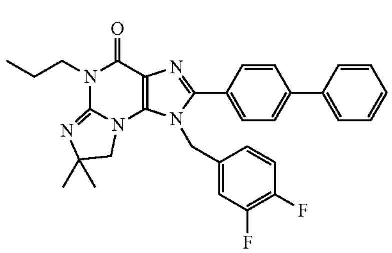 [SMILES: CCCN1C(=O)c2nc(-c3ccc(-c4ccccc4)cc3)n(Cc3ccc(F)c(F)c3)c2N2CC(C)(C)N=C12] |

| No. | Structure |
|---|---|
| 87 | |
| 88 | |
| 89 | |
| 90 | |
| 91 | |

-continued
| No. | Structure |
|---|---|
| 92 | 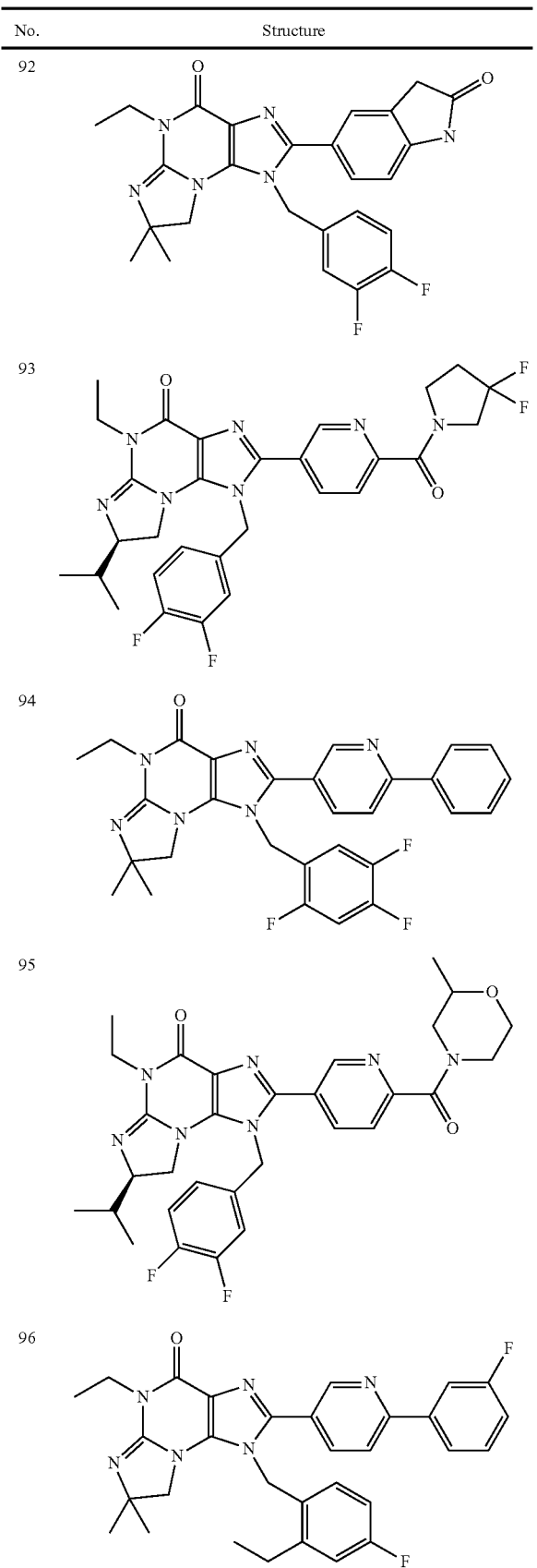 |
| 93 | 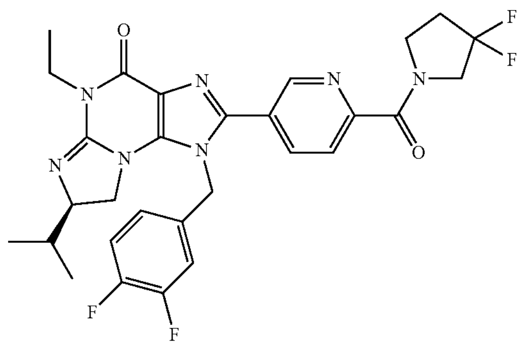 [SMILES: CCN1C(=O)c2nc(-c3ccc(C(=O)N4CCC(F)(F)C4)nc3)n(Cc3ccc(F)c(F)c3)c2N2C[C@@H](C(C)C)N=C12] |
| 94 | 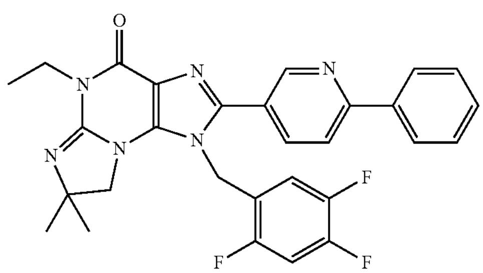 [SMILES: CCN1C(=O)c2nc(-c3ccc(-c4ccccc4)nc3)n(Cc3cc(F)c(F)cc3F)c2N2CC(C)(C)N=C12] |
| 95 | 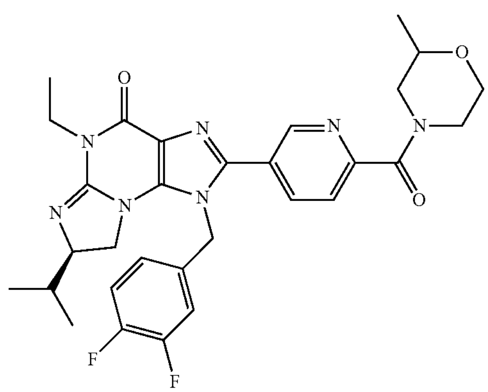 [SMILES: CCN1C(=O)c2nc(-c3ccc(C(=O)N4CCOC(C)C4)nc3)n(Cc3ccc(F)c(F)c3)c2N2C[C@@H](C(C)C)N=C12] |
| 96 | 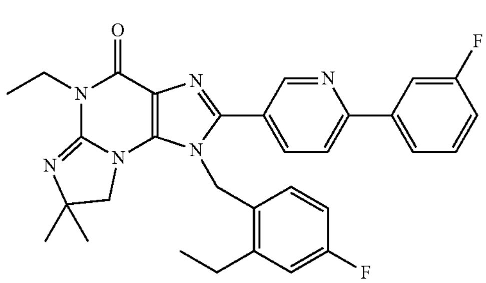 [SMILES: CCc1cc(F)ccc1Cn1c(-c2ccc(-c3cccc(F)c3)nc2)nc2c1N1CC(C)(C)N=C1N(CC)C2=O] |
-continued
| No. | Structure |
|---|---|
| 97 | 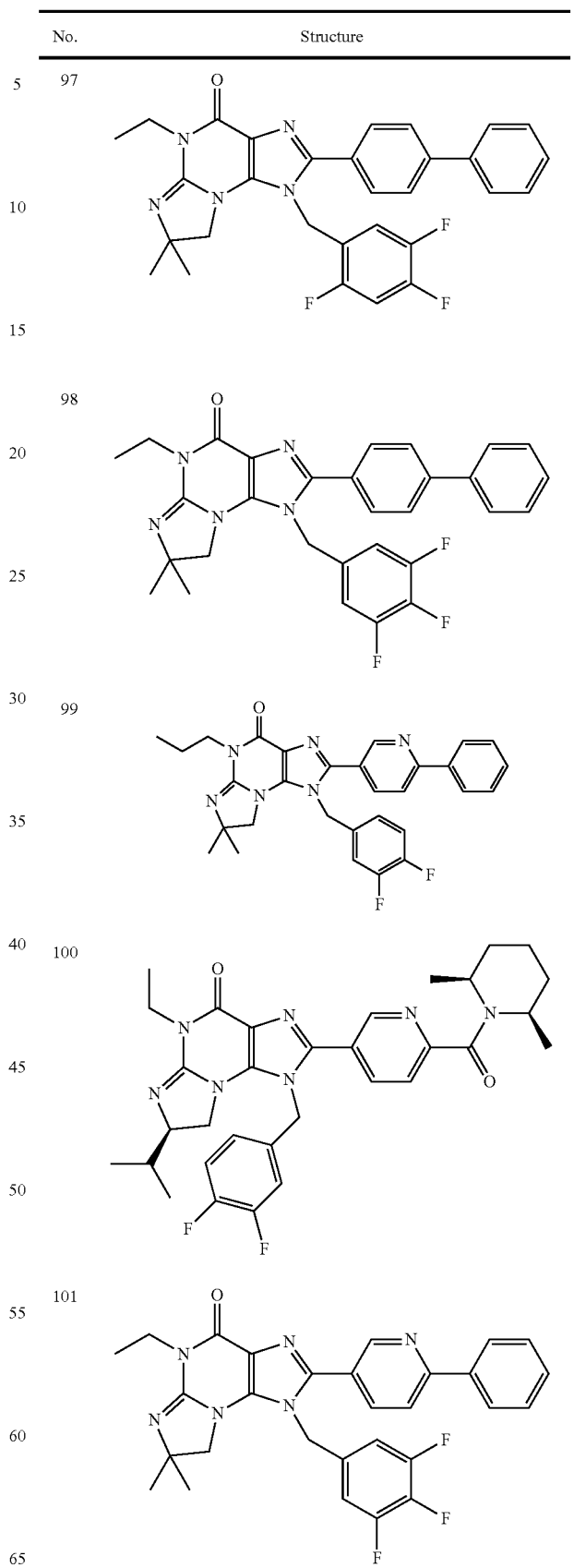 |
| 98 | 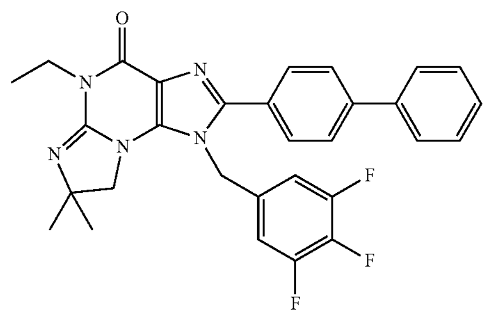 [SMILES: CCN1C(=O)c2nc(-c3ccc(-c4ccccc4)cc3)n(Cc3cc(F)c(F)c(F)c3)c2N2CC(C)(C)N=C12] |
| 99 | 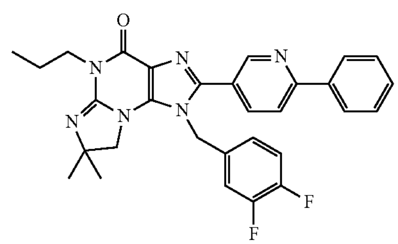 [SMILES: CCCN1C(=O)c2nc(-c3ccc(-c4ccccc4)nc3)n(Cc3ccc(F)c(F)c3)c2N2CC(C)(C)N=C12] |
| 100 | 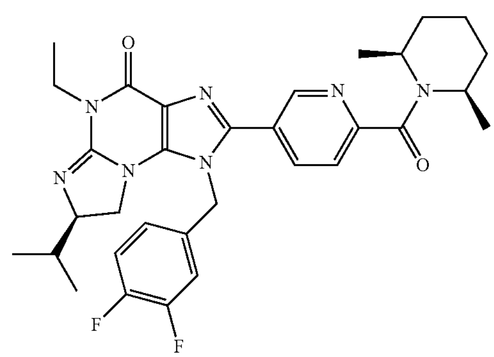 [SMILES: CCN1C(=O)c2nc(-c3ccc(C(=O)N4[C@H](C)CCC[C@@H]4C)nc3)n(Cc3ccc(F)c(F)c3)c2N2C[C@@H](C(C)C)N=C12] |
| 101 | 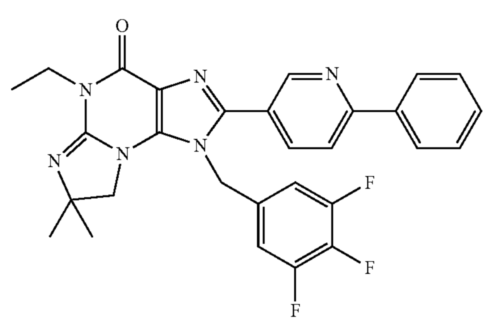 |

| No. | Structure |
|---|---|
| 102 | 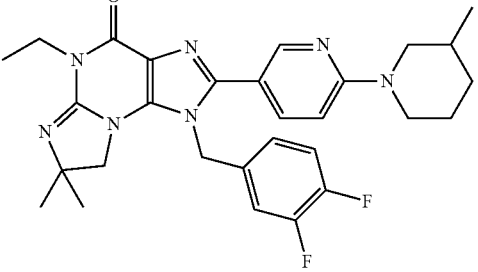 |
| 103 | 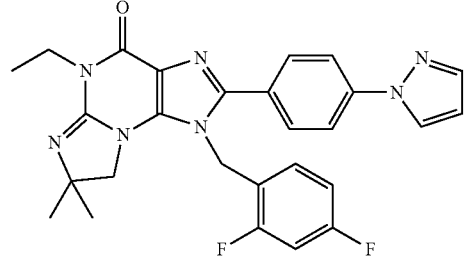 [SMILES: CCN1C(=O)c2nc(-c3ccc(-n4cccn4)cc3)n(Cc3ccc(F)cc3F)c2N2CC(C)(C)N=C12] |
| 104 | 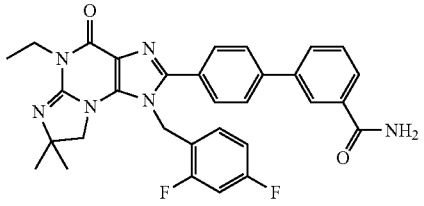 [SMILES: CCN1C(=O)c2nc(-c3ccc(-c4cccc(C(N)=O)c4)cc3)n(Cc3ccc(F)cc3F)c2N2CC(C)(C)N=C12] |
| 105 | 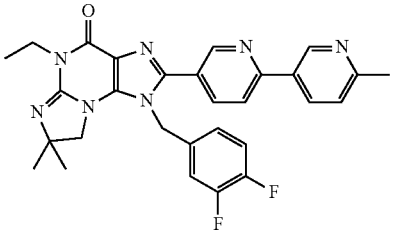 [SMILES: CCN1C(=O)c2nc(-c3ccc(-c4ccc(C)nc4)nc3)n(Cc3ccc(F)c(F)c3)c2N2CC(C)(C)N=C12] |
| 106 | 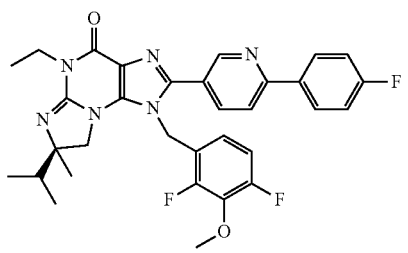 [SMILES: CCN1C(=O)c2nc(-c3ccc(-c4ccc(F)cc4)nc3)n(Cc3ccc(F)c(OC)c3F)c2N2C[C@@](C)(C(C)C)N=C12] |
| 107 | 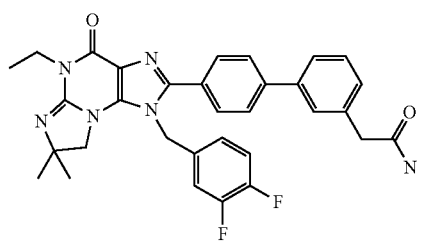 [SMILES: CCN1C(=O)c2nc(-c3ccc(-c4cccc(CC(N)=O)c4)cc3)n(Cc3ccc(F)c(F)c3)c2N2CC(C)(C)N=C12] |
| No. | Structure |
|---|---|
| 108 | 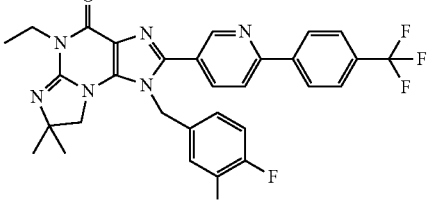 |
| 109 | 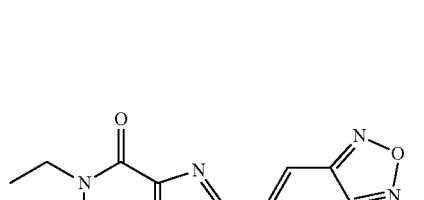 |
| 110 | 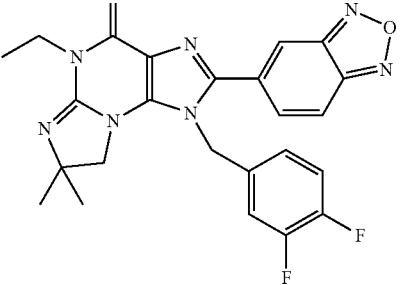 |
| 111 | 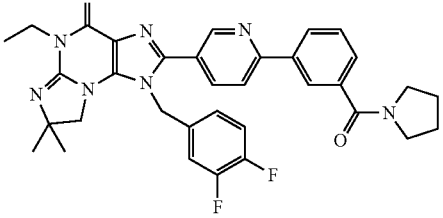 |
| 112 | 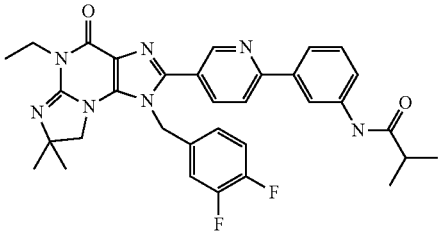 [SMILES: CCN1C(=O)c2nc(-c3ccc(-c4cccc(NC(=O)C(C)C)c4)nc3)n(Cc3ccc(F)c(F)c3)c2N2CC(C)(C)N=C12] |

| No. | Structure |
|---|---|
| 113 | 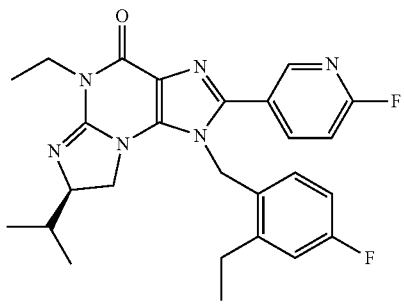 [SMILES: CCc1cc(F)ccc1Cn1c(-c2ccc(F)nc2)nc2c1N1C[C@@H](C(C)C)N=C1N(CC)C2=O] |
| 114 | 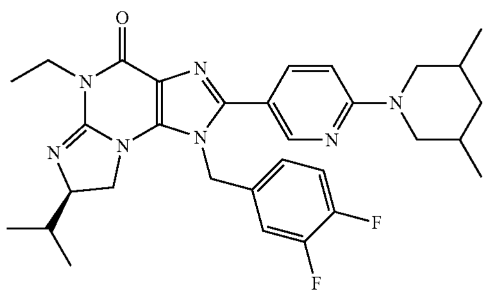 [SMILES: CCN1C(=O)c2nc(-c3ccc(N4CC(C)CC(C)C4)nc3)n(Cc3ccc(F)c(F)c3)c2N2C[C@@H](C(C)C)N=C12] |
| 115 | 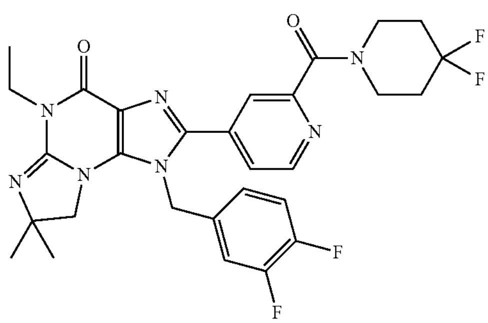 [SMILES: CCN1C(=O)c2nc(-c3ccnc(C(=O)N4CCC(F)(F)CC4)c3)n(Cc3ccc(F)c(F)c3)c2N2CC(C)(C)N=C12] |
| 116 | 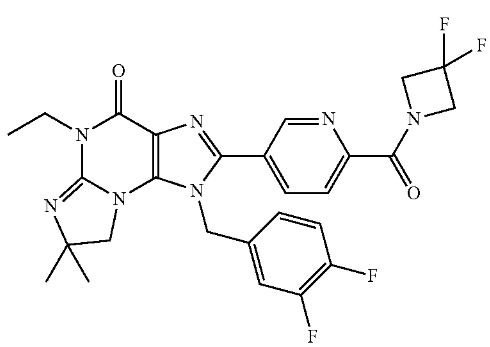 [SMILES: CCN1C(=O)c2nc(-c3ccc(C(=O)N4CC(F)(F)C4)nc3)n(Cc3ccc(F)c(F)c3)c2N2CC(C)(C)N=C12] |
| 117 | 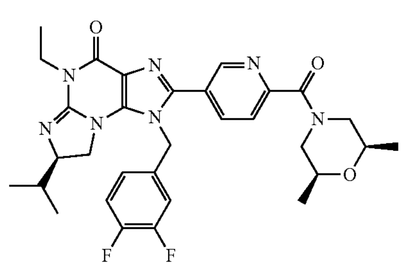 [SMILES: CCN1C(=O)c2nc(-c3ccc(C(=O)N4C[C@@H](C)O[C@@H](C)C4)nc3)n(Cc3ccc(F)c(F)c3)c2N2C[C@@H](C(C)C)N=C12] |

| No. | Structure |
|---|---|
| 118 | 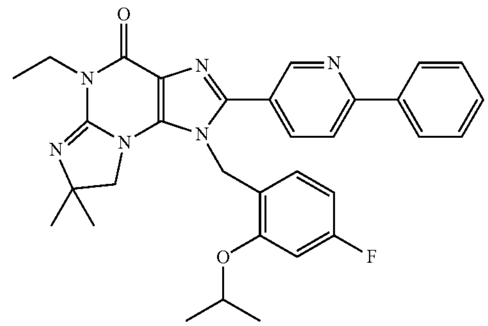 [SMILES: CCN1C(=O)c2nc(-c3ccc(-c4ccccc4)nc3)n(Cc3ccc(F)cc3OC(C)C)c2N2CC(C)(C)N=C12] |
| 119 | 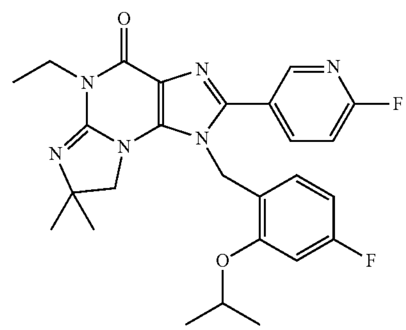 [SMILES: CCN1C(=O)c2nc(-c3ccc(F)nc3)n(Cc3ccc(F)cc3OC(C)C)c2N2CC(C)(C)N=C12] |
| 120 | 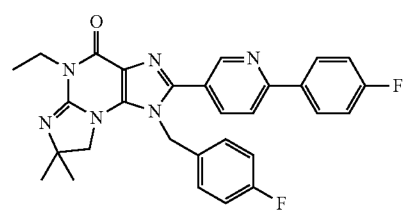 [SMILES: CCN1C(=O)c2nc(-c3ccc(-c4ccc(F)cc4)nc3)n(Cc3ccc(F)cc3)c2N2CC(C)(C)N=C12] |
| 121 | 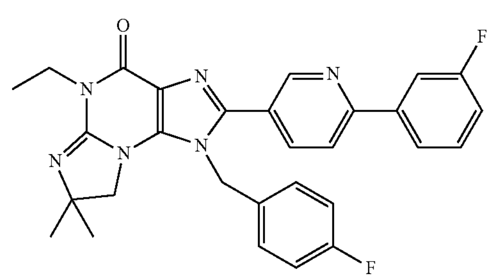 [SMILES: CCN1C(=O)c2nc(-c3ccc(-c4cccc(F)c4)nc3)n(Cc3ccc(F)cc3)c2N2CC(C)(C)N=C12] |
| 122 | 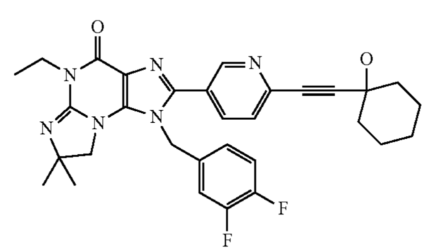 [SMILES: CCN1C(=O)c2nc(-c3ccc(C#CC4(O)CCCCC4)nc3)n(Cc3ccc(F)c(F)c3)c2N2CC(C)(C)N=C12] |

| No. | Structure |
|---|---|
| 123 | 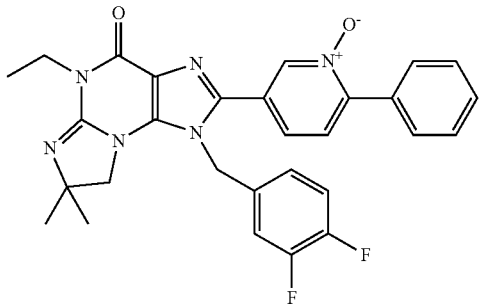 [SMILES: CCN1C(=O)c2nc(-c3ccc(-c4ccccc4)[n+]([O-])c3)n(Cc3ccc(F)c(F)c3)c2N2CC(C)(C)N=C12] |
| 124 | 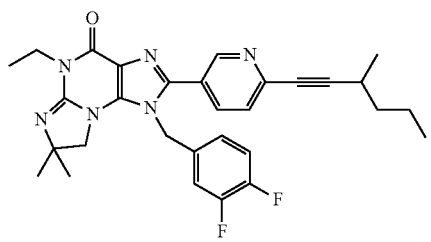 [SMILES: CCCC(C)C#Cc1ccc(-c2nc3c(n2Cc2ccc(F)c(F)c2)N2CC(C)(C)N=C2N(CC)C3=O)cn1] |
| 125 | 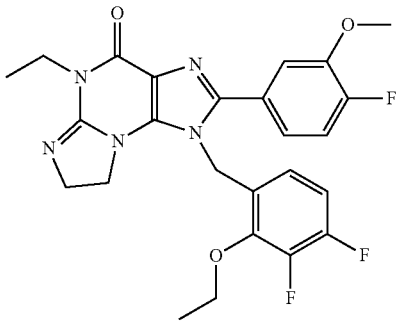 [SMILES: CCOc1c(Cn2c(-c3ccc(F)c(OC)c3)nc3c2N2CCN=C2N(CC)C3=O)ccc(F)c1F] |
| 126 | 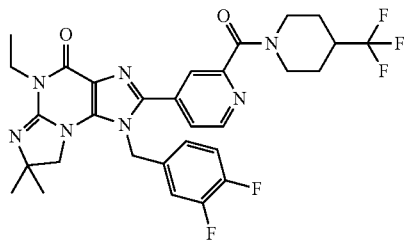 [SMILES: CCN1C(=O)c2nc(-c3ccnc(C(=O)N4CCC(C(F)(F)F)CC4)c3)n(Cc3ccc(F)c(F)c3)c2N2CC(C)(C)N=C12] |
| 127 | 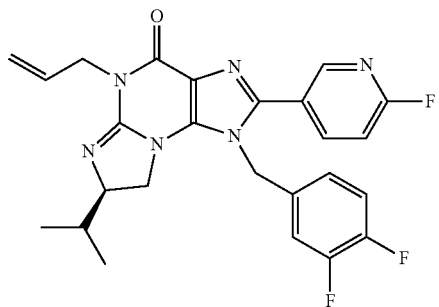 [SMILES: C=CCN1C(=O)c2nc(-c3ccc(F)nc3)n(Cc3ccc(F)c(F)c3)c2N2C[C@@H](C(C)C)N=C12] |
| No. | Structure |
|---|---|
| 128 | 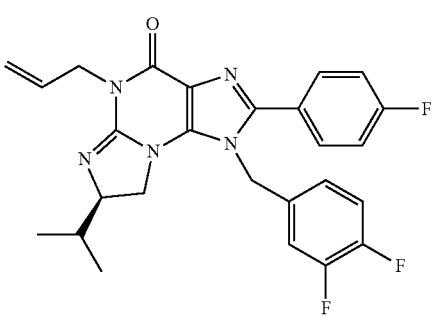 [SMILES: C=CCN1C(=O)c2nc(-c3ccc(F)cc3)n(Cc3ccc(F)c(F)c3)c2N2C[C@@H](C(C)C)N=C12] |
| 129 | 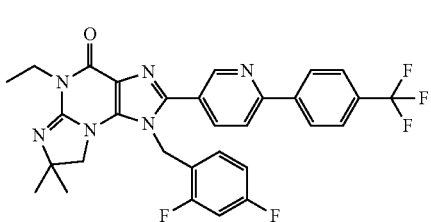 [SMILES: CCN1C(=O)c2nc(-c3ccc(-c4ccc(C(F)(F)F)cc4)nc3)n(Cc3ccc(F)cc3F)c2N2CC(C)(C)N=C12] |
| 130 | 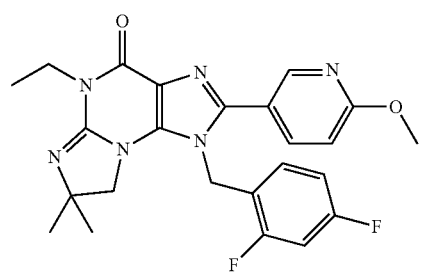 [SMILES: CCN1C(=O)c2nc(-c3ccc(OC)nc3)n(Cc3ccc(F)cc3F)c2N2CC(C)(C)N=C12] |
| 131 | 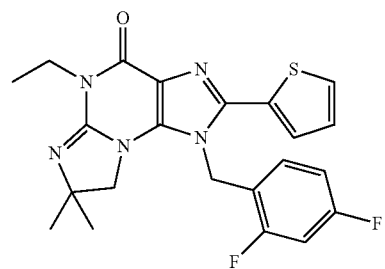 [SMILES: CCN1C(=O)c2nc(-c3cccs3)n(Cc3ccc(F)cc3F)c2N2CC(C)(C)N=C12] |
| 132 | 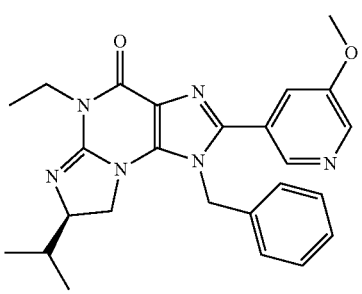 [SMILES: CCN1C(=O)c2nc(-c3cncc(OC)c3)n(Cc3ccccc3)c2N2C[C@@H](C(C)C)N=C12] |

| No. | Structure |
|---|---|
| 133 | 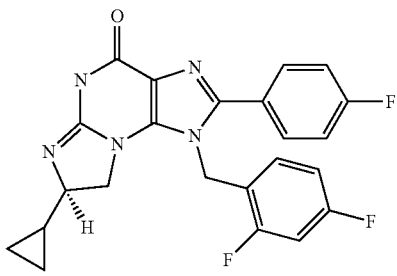 [SMILES: O=C1NC2=N[C@H](C3CC3)CN2c2c1nc(-c1ccc(F)cc1)n2Cc1ccc(F)cc1F] |
| 134 | 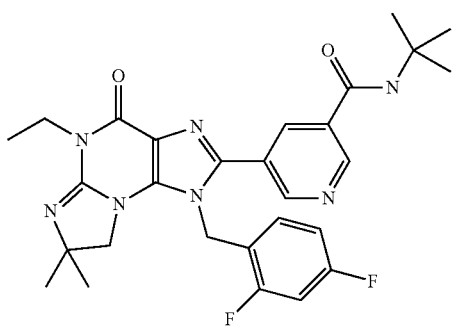 [SMILES: CCN1C(=O)c2nc(-c3cncc(C(=O)NC(C)(C)C)c3)n(Cc3ccc(F)cc3F)c2N2CC(C)(C)N=C12] |
| 135 | 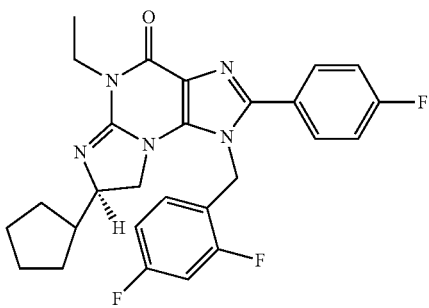 [SMILES: CCN1C(=O)c2nc(-c3ccc(F)cc3)n(Cc3ccc(F)cc3F)c2N2C[C@@H](C3CCCC3)N=C12] |
| 136 | 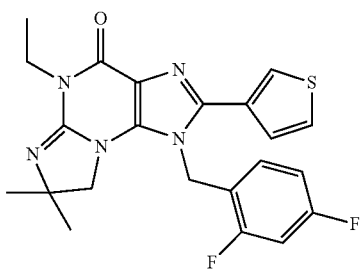 [SMILES: CCN1C(=O)c2nc(-c3ccsc3)n(Cc3ccc(F)cc3F)c2N2CC(C)(C)N=C12] |
| 137 | 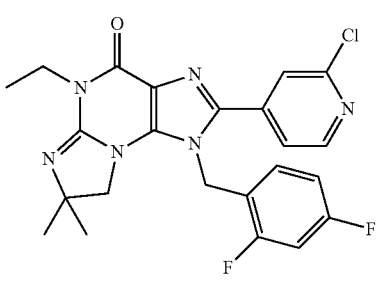 [SMILES: CCN1C(=O)c2nc(-c3ccnc(Cl)c3)n(Cc3ccc(F)cc3F)c2N2CC(C)(C)N=C12] |
| No. | Structure |
|---|---|
| 138 | 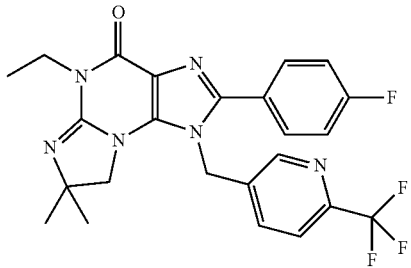 [SMILES: CCN1C(=O)c2nc(-c3ccc(F)cc3)n(Cc3ccc(C(F)(F)F)nc3)c2N2CC(C)(C)N=C12] |
| 139 | 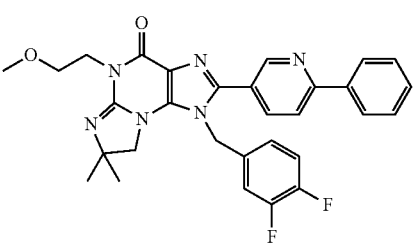 [SMILES: COCCN1C(=O)c2nc(-c3ccc(-c4ccccc4)nc3)n(Cc3ccc(F)c(F)c3)c2N2CC(C)(C)N=C12] |
| 140 | 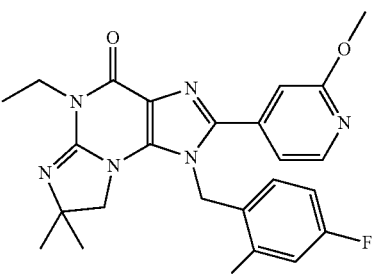 |
| 141 | 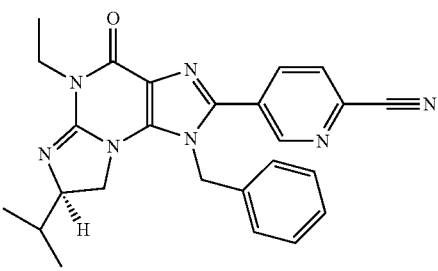 [SMILES: CCN1C(=O)c2nc(-c3ccc(C#N)nc3)n(Cc3ccccc3)c2N2C[C@@H](C(C)C)N=C12] |
| 142 | 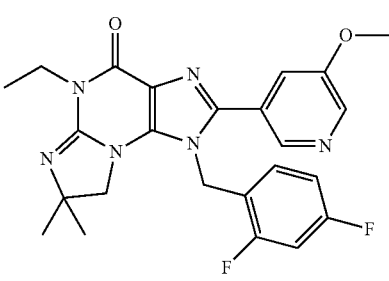 [SMILES: CCN1C(=O)c2nc(-c3cncc(OC)c3)n(Cc3ccc(F)cc3F)c2N2CC(C)(C)N=C12] |

-continued

| No. | Structure |
|---|---|
| 143 | 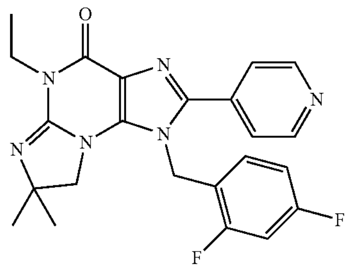 [SMILES: CCN1C(=O)c2nc(-c3ccncc3)n(Cc3ccc(F)cc3F)c2N2CC(C)(C)N=C12] |
| 144 | 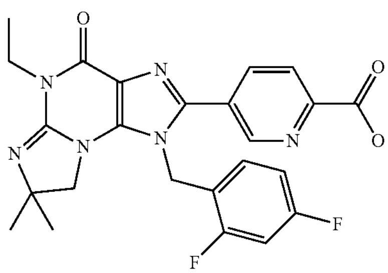 [SMILES: CCN1C(=O)c2nc(-c3ccc(C(=O)O)nc3)n(Cc3ccc(F)cc3F)c2N2CC(C)(C)N=C12] |
| 145 | 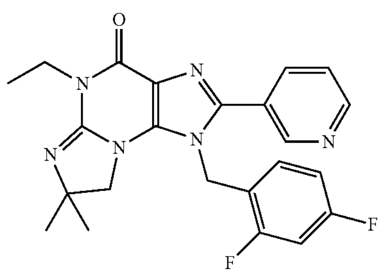 [SMILES: CCN1C(=O)c2nc(-c3cccnc3)n(Cc3ccc(F)cc3F)c2N2CC(C)(C)N=C12] |
| 146 | 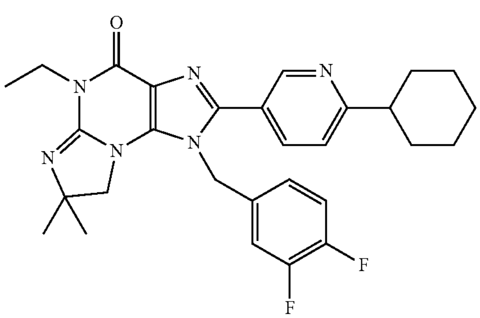 [SMILES: CCN1C(=O)c2nc(-c3ccc(C4CCCCC4)nc3)n(Cc3ccc(F)c(F)c3)c2N2CC(C)(C)N=C12] |
| 147 | 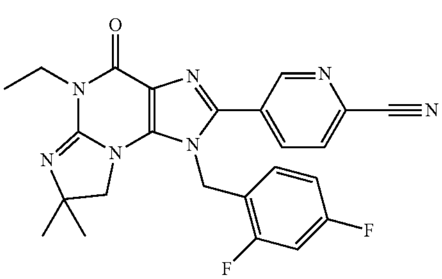 [SMILES: CCN1C(=O)c2nc(-c3ccc(C#N)nc3)n(Cc3ccc(F)cc3F)c2N2CC(C)(C)N=C12] |

-continued

| No. | Structure |
|---|---|
| 148 | |
| 149 | |
| 150 | |
| 151 | |
| 152 | |
| 153 | | and pharmaceutically acceptable salts, solvates, esters and prodrugs thereof.

Methods for Making the Polycyclic Guanine Derivatives

Methods useful for making the Polycyclic Guanine Derivatives of the present invention are set forth in the Examples below and generalized in Schemes 1-5. Alternative synthetic pathways and analogous structures will be apparent to those skilled in the art of organic synthesis. Alternatively, the Polycyclic Guanine Derivatives may also be made using the methods set forth in U.S. Pat. No. 5,393,755.

Scheme 1 illustrates a method useful for making compounds of formula iv, which are useful intermediates for making the Polycyclic Guanine Derivatives, wherein $R^3$ is —CH$_2$-aryl or —CH$_2$-heteroaryl.

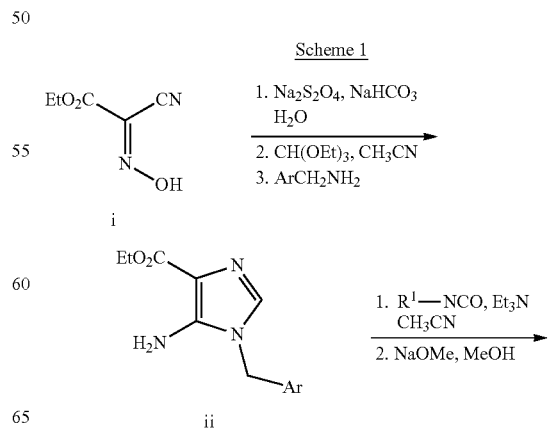

Scheme 1

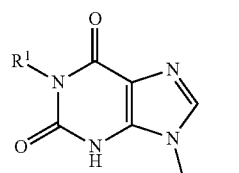

iii

↓ POCl₃ reflux

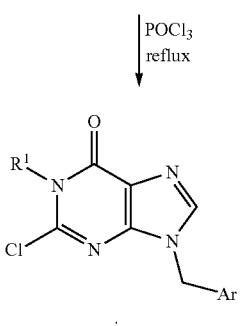

iv wherein Ar is aryl or heteroaryl.

Ethyl cyanoglyoxylate-2-oxime (i) can be reacted with sodium dithionate in the presence of a base such as NaHCO₃ and the resulting product refluxed with an appropriate substituted benzimidic acid ethyl ester hydrochloride, followed by treatment with an appropriate benzylamine to provides the imidazole compounds of formula II. A compound of formula II can then be reacted with an isocynate of formula R¹—NCO in the presence of triethylamine, followed by treatment with methanol to provide the compounds of formula iii. A compound of formula iii is then reacted with phosphorus oxychloride to provide the compounds of formula iv.

Scheme 2 illustrates a method useful for making compounds of formula vi, which are useful intermediates for making the Polycyclic Guanine Derivatives, wherein R³ is —CH₂-aryl or —CH₂-heteroaryl.

Scheme 2

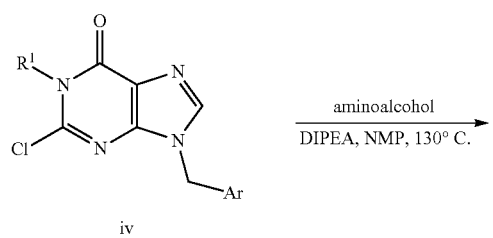

iv

↓ aminoalcohol
DIPEA, NMP, 130° C.

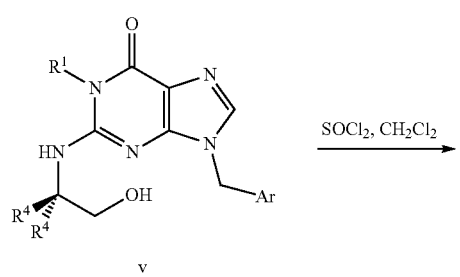

v

↓ SOCl₂, CH₂Cl₂

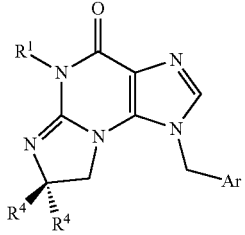

vi wherein R¹ and R⁴ are defined above for the Polycyclic Guanine Derivatives and Ar is aryl or heteroaryl.

A compound of formula iv can be coupled with an aminoalcohol in the presence of a non-nucleophilic base, such as DIPEA, to provide the hydroxy compounds of formula v. A compound of formula v can then be cyclized upon treatment with thionyl chloride to provide the compounds of formula vi.

Scheme 3 illustrates a method useful for making the compounds of formula ix, which correspond to the PDG's wherein R² is aryl and R³ is —CH₂-aryl or —CH₂-heteroaryl.

Scheme 3

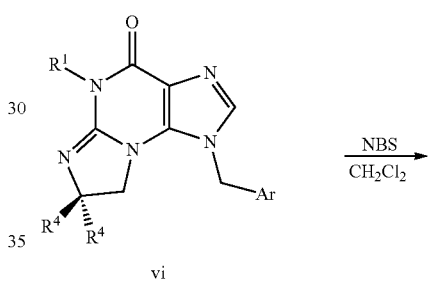

vi

↓ NBS
CH₂Cl₂

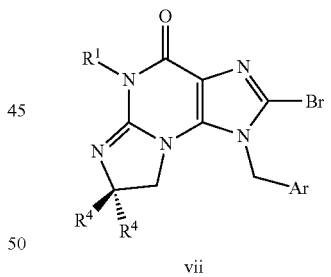 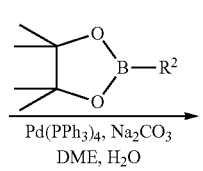

Pd(PPh₃)₄, Na₂CO₃
DME, H₂O vii

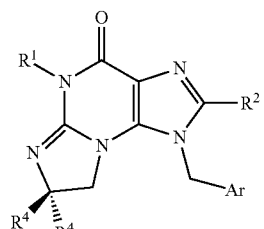

ix wherein $R^1$ and $R^4$ are defined above for the Polycyclic Guanine Derivatives, $R^2$ is aryl, and Ar is aryl or heteroaryl.

A compound of formula vi can be brominated using N-bromosuccinimide to provide the bromo compounds of formula vii, which can subsequently be coupled with a boronic ester of formula viii via a Suzuki coupling reaction to provide the compounds of formula ix. The boronic acid esters of formula viii can be made using the methods set forth in the examples section herein or via methods well-known to those of ordinary skill in the art of organic synthesis.

Scheme 4 shows an alternative method for making the Polycyclic Guanine Derivatives.

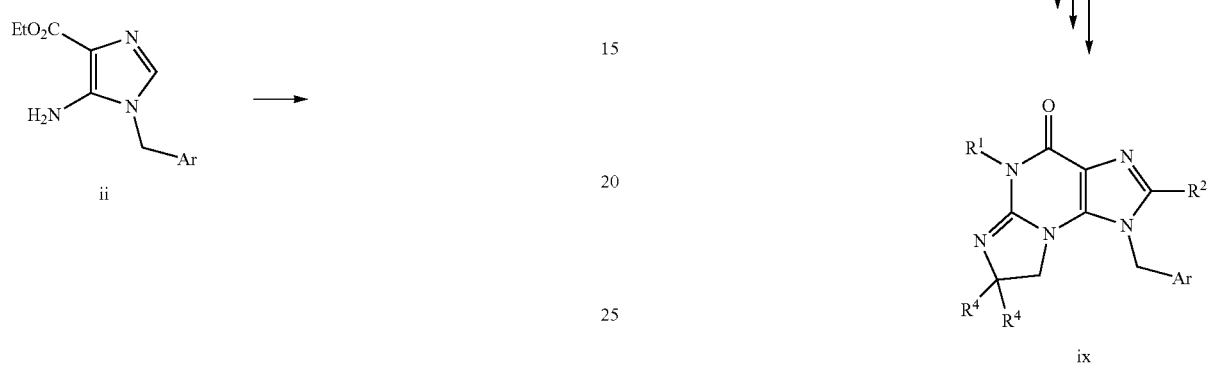

wherein $R^1$ and $R^4$ are defined above for the Polycyclic Guanine Derivatives, $R^2$ is aryl, and Ar is aryl or heteroaryl.

An imidazole compound of formula II can be brominated then coupled with a boronic acid ester to provide a compound of formula x using methodology set forth in Scheme 3 above. A compound of formula x can then be cyclized to provide the bicyclic compounds of formula xi using methodology set forth in Scheme 1 above. A compound of formula xi is then cyclized using the method set forth in Scheme 2 above to provide the bicyclic compounds of formula ix.

Scheme 5 illustrates an alternative method for making the Polycyclic Guanine Derivatives.

wherein $R^1$ and $R^4$ are defined above for the Polycyclic Guanine Derivatives, $R^2$ is aryl, Ar is aryl or heteroaryl, and X is a good leaving group, such as —Br, —Cl, —I, —O-mesyl, —O-tosyl or —O-triflyl.

The commercially available compound of formula xii can be reacted with an arylalkyl bromide in the presence of a base, such as potassium carbonate, to provide the N-derivatized compounds of formula xiii. A compound of formula xiii can then be converted to the compounds of formula xiv upon exposure to a hydroxide base, such as sodium hydroxide. A compound of formula xiv can then be reacted with a compound of formula $R^1X$ in the presence of a carbonate base, such as potassium carbonate to provide the compounds of formula xv. The compounds of formula xv can finally be converted to the compounds of formula xi as described above in Scheme 4.

The starting materials and reagents depicted in Schemes 1-5 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art of organic synthesis will recognize that the preparation of the Polycyclic Guanine Derivatives may require the need for the protection of certain functional groups (i.e., derivatization for the purpose of chemical compatibility with a particular reaction condition). Suitable protecting groups for the various functional groups of the Polycyclic Guanine Derivatives and methods for their installation and removal may be found in Greene et al., *Protective Groups in Organic Synthesis*, Wiley-Interscience, New York, (1999).

Uses of the Polycyclic Guanine Derivatives

The Polycyclic Guanine Derivatives are useful in human and veterinary medicine for treating or preventing a Condition in a patient. In accordance with the invention, the Polycyclic Guanine Derivatives can be administered to a patient in need of treatment or prevention of a Condition.

Treatment of Pain

The Polycyclic Guanine Derivatives are useful for treating or preventing pain in a patient.

Accordingly, in one embodiment, the present invention provides a method for treating pain in a patient, comprising administering to the patient an effective amount of one or more Polycyclic Guanine Derivatives.

In another embodiment, the present invention provides a method for treating pain in a patient, comprising administering to the patient an effective amount of one or more of illustrative compounds 1-160.

In another embodiment, the present invention provides a method for treating pain in a patient, comprising administering to the patient an effective amount of one or more Compounds of Formula (II).

Non-limiting examples of pain treatable or preventable using the present methods, include acute pain, back pain, chronic pain, fibromyalgia, post-herpetic neuralgia, neuropathic pain, nociceptive pain, cutaneous pain, somatic pain, visceral pain, phantom limb pain, cancer pain (including breakthrough pain), pain caused by drug therapy (such as cancer chemotherapy), headache (including migraine, tension headache, cluster headache, inflammatory pain, pain caused by diabetes, pain caused by arthritis, pain caused by injury, toothache, or pain caused by a medical procedure (such as surgery, physical therapy or radiation therapy).

In one embodiment, the pain is neuropathic pain.
In another embodiment, the pain is cancer pain.
In another embodiment, the pain is headache.
In still another embodiment, the pain is chronic pain.
In yet another embodiment, the pain is pain cause by arthritis.
In another embodiment, the pain is pain cause by diabetes.
In a further embodiment, the pain is inflammatory pain.

Neuropathic pain as used herein refers to an abnormal state of pain sensation, in which a reduction of pain threshold and the like are continued, due to functional abnormalities accompanying damage or degeneration of a nerve, plexus or perineural soft tissue, which is caused by wound (e.g., lacerations, contusions, nerve avulsion injuries, amputation of a limb), compression (carpal tunnel syndrome, trigeminal neuralgia, tumor activity), infection, cancer, ischemia and the like, or metabolic disorders such as diabetes mellitus and the like. Neuropathic pain includes pain caused by central nerve damage, peripheral nerve damage, diabetic neuropathy, mononeuropathy or polyneuropathy. In one embodiment, the neuropathic pain is induced by diabetes.

Other examples of neuropathic pain treatable or preventable using the Polycyclic Guanine Derivatives include, but are not limited to, pain caused by naturopathic therapy, pain that is resistant to naturopathic therapy, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, central pain, labor pain, myocardial infarction pain, post-stroke pain, pancreatic pain, colic pain, muscle pain, post-operative pain, post-stroke pain, pain associated with Parkinson's disease, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, bursitis, pain associated with AIDS, pain associated with multiple sclerosis, pain due to spinal trauma and/or degeneration, burn pain, referred pain, enhanced memory of pain and neuronal mechanisms involved in coping with pain. Inflammatory pain may arise as a result of soft tissue injury including that involving the musculature (myositis) and viscera (colitis and inflammatory bowel disease, pancreatitis, cystitis, ileitis, Crohn's disease), nerves (neuritis, radiculopathies, radioculogangionitis), arthritic conditions (e.g. rheumatoid disease and related conditions such as ankylosing spondylitis), joint disease (including osteoarthritis). In specific embodiments, the Polycyclic Guanine Derivatives of the present invention are useful for treating or preventing allodynia or hyperalgesia.

Treatment of an Inflammatory Disease

The Polycyclic Guanine Derivatives can be useful for treating or preventing an inflammatory diesase in a patient.

Accordingly, in one embodiment, the present invention provides a method for treating an inflammatory diesase in a patient, comprising administering to the patient an effective amount of one or more Polycyclic Guanine Derivatives.

In another embodiment, the present invention provides a method for treating an inflammatory diesase in a patient, comprising administering to the patient an effective amount of one or more Compounds of Formula (II).

In another embodiment, the present invention provides a method for treating an inflammatory diesase in a patient, comprising administering to the patient an effective amount of one or more of illustrative compounds 1-160.

Non-limiting examples of inflammatory diseases treatable or preventable using the present methods, include diabetic neuropathy; arthritis, such as osteoarthritis, rheumatoid arthritis, septic arthritis, gout, pseudogout, juvenile arthritis or Still's disease; inflammatory bowel diseases, such as ileitis, Crohn's disease and ulcerative colitis; organ transplant rejection; inflammatory bowel disease; inflammatory lung diseases such as asthma, adult respiratory distress syndrome and chronic obstructive pulmonary disease (COPD); inflammatory diseases of the eye, such as, corneal dystrophy, trachoma, uveitis and sympathetic ophthalmitis; chronic inflammatory diseases of the gum, such as gingivitis and periodontitis; inflammatory diseases of the kidney, such as glomerulonephritis and nephrosis; inflammatory diseases of the skin, such as sclerodermatitis, psoriasis and eczema; renal colic; reperfusion injury; pyrexia; ischemic injury; multiple sclerosis; systemic lupus erythematosis; periodic fever syndromes, such as chronic infantile neurological cutaneous and articular syndrome (CINCA), familial cold autoinflammatory syndrome (FCAS), Muckle-Wells Syndrome (MWS), familial Mediterranean fever (FMF) and pyrogenic arthritis, pyroderma gangrenosum and acne syndrome (PAPA); and inflammatory arthropathies, such as ankylosing spondylitis, psoriatric arthritis and Reiter's syndrome.

The term "inflammatory disease" as used herein included both local inflammatory responses and systemic inflammation.

In one embodiment, the inflammatory disease is arthritis.

In another embodiment, the inflammatory disease is rheumatoid arthritis.

In another embodiment, the inflammatory disease is osteoarthritis.

In still another embodiment, the inflammatory disease is asthma.

In yet another embodiment, the inflammatory disease is chronic obstructive pulmonary disease (COPD).

In another embodiment, the inflammatory disease is inflammatory bowel disease.

Combination Therapy

In one embodiment, the present invention provides methods for treating a Condition in a patient, the method comprising administering to the patient one or more Polycyclic Guanine Derivatives, or a pharmaceutically acceptable salt, solvate, ester or prodrug thereof and at least one additional therapeutic agent that is not a Polycyclic Guanine Derivative, wherein the amounts administered are together effective to treat or prevent a Condition.

In one embodiment, the additional therapeutic agent is an analgesic agent.

Additional analgesic agents useful in the present methods for treating pain include, but are not limited to, non-opioid (also known as non-steroidal anti-inflammatory agents) analgesics such as acetylsalicylic acid, choline magnesium trisalicylate, acetaminophen, ibuprofen, fenoprofen, diflusinal, and naproxen; opioid analgesics such as morphine, hydromorphone, methadone, levorphanol, fentanyl, oxycodone, and oxymorphone; steroids such as prednisolone, fluticasone, triamcinolone, beclomethasone, mometasone, budisamide, betamethasone, dexamethasone, prednisone, flunisolide and cortisone; COX-I inhibitors such as aspirin and piroxicam; and COX-II inhibitors such as rofecoxib, celecoxib, valdecoxib and etoricoxib.

Other analgesic agents useful in the present methods for treating pain include, but are not limited to, gabapentin, pregabalin and duloxetine.

In one embodiment, the other analgesic agent is an opioid analgesic. In another embodiment, the other analgesic agent is a non-opioid analgesic. In another embodiment, the other analgesic agent is a COX-I inhibitor. In still another embodiment, the other analgesic agent is a COX-II inhibitor. In yet another embodiment, the other analgesic agent is selected from aspirin, acetaminophen, ibuprofen, fenoprofen, naproxen, morphine, hydromorphone, methadone, levorphanol, fentanyl, oxycodone, and oxymorphone.

In one embodiment, the additional therapeutic agent is an anti-inflammatory agent.

Non-limiting examples of additional anti-inflammatory agents useful in the present methods for treating an inflammatory disease include non-steroidal anti-inflammatory agents (NSAIDs); steroidal anti-inflammatory drugs, such as cortisol, dexamethasone, predinsone, prednisolone, methylprednisone, betamethasone, beclometasone, fludrocortisone acetate, deoxycorticosterone acetate, aldosterone, corticosterone and cortisone; agents useful for treating inflammatory bowel disease such as IL-10, steroids, and azulfidine; agents useful for treating rheumatoid arthritis such as methotrexate, azathioprine, cyclophosphamide, steroids and mycophenolate mofetil; agents for treating or preventing inflammatory bowel disease.

Other anti-inflammatory agents useful in the present methods for treating an inflammatory disease include, but are not limited to, rituximab, adalimumab, infliximab, etanercept, TACE inhibitors, muscarinic antagonists, kinase inhibitors, cytokine inhibitors and chemokine inhibitors.

Non-limiting examples of non-steroidal anti-inflammatory agents (NSAIDs) useful in the present methods for treating an inflammatory disease include salicylates such as aspirin, amoxipirin, benorilate, choline magnesium sulfate, diflunisal, faislamine, methyl salicylate, magnesium salicylate and salicyl saliciylate; arylalkanoic acids, such as diclofenac, aceclofenac, acemetacin, bromfenac, etodolac, indometacin, nabumetone, sulindac and tolmetin; profens, such as ibuprofen, carprofen, fenbufen, fenoprofen, flurbiprofen, ketoprofen, ketorolac, loxoprofen, naproxen, tiaprofenic acid and suprofen; fenamic acids, such as mefenamic acid and meclofenamic acid; pyrazolidine derivatives, such as phenylbutazone, azapropazone, metamizole, oxyphenbutazone and sulfinprazone; oxicams, such as piroxicam, lornoxicam, meloxicam and tenoxicam; COX-2 inhibitors, such as celecoxib, rofecoxib, etoricoxib, lumiracoxib, parecoxib and valdecoxib; sulfonalides, such as nimesulfide; licofelone; omega-3 fatty acids; and PDE inhibitors.

In one embodiment, the NSAID is a profen or a salicylate.
In another embodiment, the NSAID is a COX-2 inhibitor.
In one embodiment, the additional therapeutic agent is an anti-asthmatic agent.

Non-limiting examples of anti-asthmatic agents useful in the present methods for treating asthma include beta-2 adrenoceptor angoinsts, such as salmeterol, formoterol, bambuterol, albuterol, salbutamol, levalbuterol, terbutaline and bitolterol; ephedrine; ipatropium bromide; glucocorticoids, such as ciclesonide, beclomethasone, budesonide, funisolide, futicasone, mometasone and triamcinolone; leukotriene modifiers, such as montelukast, zafirlukast, pranlukast and zileuton; mast cell stabilizers, such as cromolyn and nedocromil; anticholinergics, such as ipatropium, glycopyrrolate, atropine, oxitropium and tiotropium; methylxanthines, such as theophylline and aminophylline; an antihistamine; an IgE, such as omalizumab; methotrexate; tianeptine; steroids such as prednisone, prednisolone, methylprednisone, dexamethasone and hydrocortisone; beta-agonists, such as epinephrine, isoetharine, isoproterenol and metaproterenol; inhalation anesthetics, such as isoflurane, halothane and enflurane; magnesium sulfate; heliox, which is a mixture of helium and oxygen; and expectorants, such as guaifenesin.

In one embodiment, the inflammatory disease treated using the combination therapies of the present invention is asthma. In another embodiment, the inflammatory disease is arthritis. In still another embodiment, the inflammatory disease is rheumatoid arthritis or osteoarthritis. In yet another embodiment, the inflammatory disease is COPD. In a further embodiment, the inflammatory disease is inflammatory bowel disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Polycyclic Guanine Derivatives are administered during a time when the additional therapeutic agent(s) exert their prophylactic or therapeutic effect, or vice versa.

In another embodiment, the one or more Polycyclic Guanine Derivatives and the additional therapeutic agent(s) are administered in doses commonly employed when such agents are used as monotherapy for treating a Condition.

In another embodiment, the one or more Polycyclic Guanine Derivatives and the additional therapeutic agent(s) are administered in doses lower than the doses commonly employed when such agents are used as monotherapy for treating a Condition.

In still another embodiment, the one or more Polycyclic Guanine Derivatives and the additional therapeutic agent(s) act synergistically and are administered in doses lower than the doses commonly employed when such agents are used as monotherapy for treating a Condition.

In one embodiment, the one or more Polycyclic Guanine Derivatives and the additional therapeutic agent(s) are present in the same composition. In one embodiment, this composition is suitable for oral administration. In another embodiment, this composition is suitable for intravenous administration.

The one or more Polycyclic Guanine Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Polycyclic Guanine Derivatives and the additional therapeutic agent(s) may inhibit the resistance of a Condition to these agents.

In another embodiment, the additional therapeutic agent is an agent useful for reducing any potential side effect of a Polycyclic Guanine Derivative. Such potential side effects include, but are not limited to, nausea, vomiting, headache, fever, lethargy, muscle aches, diarrhea, general pain, and pain at an injection site.

In one embodiment, the additional therapeutic agent is used at its known therapeutically effective dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Polycyclic Guanine Derivative(s) and the other agent(s) for treating diseases or conditions listed above can be administered simultaneously or sequentially. This particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Polycyclic Guanine Derivatives and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

Compositions and Administration

In one embodiment, the invention provides methods for treating a Condition in a patient, comprising administering to the patient a composition comprising an effective amount of one or more Polycyclic Guanine Derivatives or a pharmaceutically acceptable salt, solvate, ester or prodrug thereof, and a pharmaceutically acceptable carrier. In another embodiment, the invention provides methods for treating a Condition in a patient, comprising administering to the patient more than one composition, each comprising an effective amount of one or more Polycyclic Guanine Derivatives or a pharmaceutically acceptable salt, solvate, ester or prodrug thereof, and a pharmaceutically acceptable carrier.

For preparing pharmaceutical compositions from the Polycyclic Guanine Derivatives, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A.

Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the Polycyclic Guanine Deriative is administered orally.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of one or more Polycyclic Guanine Derivatives and an additional therapeutic agent, the two active components may be co-administered simultaneously or sequentially, or a single pharmaceutical composition comprising one or more Polycyclic Guanine Derivatives and an additional therapeutic agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of the advantageous effect of the combination.

In one embodiment, the components of a combination therapy regime are to be administered simultaneously, they can be administered in a single composition with a pharmaceutically acceptable carrier.

In another embodiment, when the components of a combination therapy regime are to be administered separately or sequentially, they can be administered in separate compositions, each containing a pharmaceutically acceptable carrier.

The components of the combination therapy can be administered individually or together in any conventional dosage form such as capsule, tablet, powder, cachet, suspension, solution, suppository, nasal spray, etc.

Kits

In one aspect, the present invention provides a kit comprising an effective amount of one or more Polycyclic Guanine Derivatives, or a pharmaceutically acceptable salt or solvate of the compound and a pharmaceutically acceptable carrier, vehicle or diluent.

In another aspect the present invention provides a kit comprising an amount of one or more Polycyclic Guanine Derivatives, or a pharmaceutically acceptable salt or solvate of the compound and an amount of at least one additional therapeutic agent listed above, wherein the combined amounts are effective for treating or preventing diabetes, a diabetic complication impaired glucose tolerance or impaired fasting glucosein a patient.

When the components of a combination therapy regime are to be administered in more than one composition, they can be provided in a kit comprising in a single package, one or more containers, each comprising one or more Polycyclic Guanine Derivatives in a pharmaceutically acceptable carrier, and a separate container comprising an additional therapeutic agent in a pharmaceutically acceptable carrier, with the active components of each composition being present in amounts such that the combination is therapeutically effective.

EXAMPLES

The following examples exemplify illustrative examples of compounds of the present invention and are not to be construed as limiting the scope of the disclosure. Alternative mechanistic pathways and analogous structures within the scope of the invention may be apparent to those skilled in the art.

General Methods

Solvents, reagents, and intermediates that are commercially available were used as received unless otherwise indicated. Reagents and intermediates that are not commercially available were prepared in the manner described below. $^1$H NMR spectra were obtained on a Varian 400 MHz or Bruker 300 MHz instrument and are reported as ppm down field from

Example 1

Preparation of Compound 2a

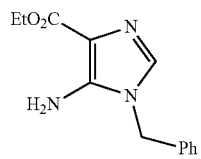

2a

A 2-L three-necked round-bottomed flask equipped with a mechanical stirrer was charged with ethyl cyanoglyoxylate-2-oxime (40.0 g, 0.281 mol) and saturated aqueous NaHCO$_3$ (300 mL). With vigorous stirring, water (300 mL) was added, followed by portionwise addition of sodium dithionite (200 g, 1.15 mol) over 45 minutes. After stirring for 15 minutes, the solution was extracted with CH$_2$Cl$_2$ (4×250 mL) and the combined organic extracts were dried over sodium sulfate, filtered and concentrated in vacuo to provide a yellow oil. To a stirred solution of this yellow oil in CH$_3$CN (150 mL) was added triethyl orthoformate (42.6 mL, 0.256 mol). The reaction mixture was heated to reflux and allowed to stir at this temperature for 30 minutes, then cooled to room temperature. Benzylamine (31.1 mL, 0.285 mol) was then added and the resulting reaction was heated to reflux and allowed to stir at this temperature for 30 minutes, then cooled to room temperature and concentrated in vacuo. The brown viscous oil was triturated with EtOAc (150 mL) and the resulting suspension was stirred overnight. The precipitate was collected, washed with cold EtOAc (2×100 mL), air-dried for 1 hour and further dried in a vacuum oven at 50° C. to provide compound 2a (23.7 g, 34%) as an off-white solid.

Example 2

Preparation of Compound 2b

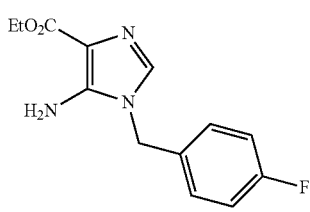

2b

Using the method described in Example 1 and substituting 4-fluorobenzylamine for benzylamine, compound 2b was synthesized as an off-white solid.

Example 3

Preparation of Compound 2c

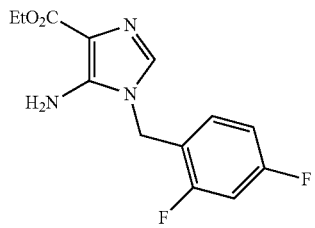

2c

Using the method described in Example 1 and substituting 2,4-difluorobenzylamine for benzylamine, compound 2b was synthesized as an off-white solid.

Example 4

Preparation of Compound 2d

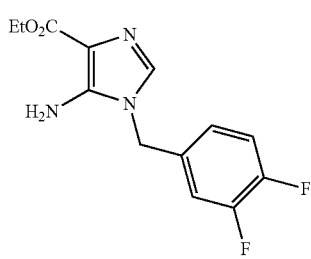

2d

Using the method described in Example 1 and substituting 3,4-difluorobenzylamine for benzylamine, compound 2b was synthesized as an off-white solid.

Example 5

Preparation of Compound 2e

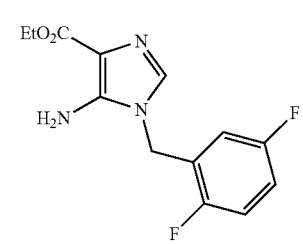

2e

Using the method described in Example 1 and substituting 2,5-difluorobenzylamine for benzylamine, compound 2b was synthesized as an off-white solid.

Example 6

Preparation of Compound 3a

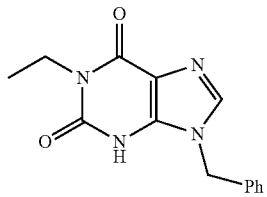

3a

A 2-L three-necked round-bottomed flask equipped with a magnetic stir bar was charged with ethyl 5-amino-1-benzyl-1H-imidazole-4-carboxylate (2a) (50.0 g, 0.204 mol), ethyl isocyanate (64 mL, 0.816 mol), triethylamine (142 ml, 1.02 mol) and toluene (450 mL). The reaction mixture was heated under reflux for 18 hours, cooled to room temperature and concentrated in vacuo to a black solid. To a mechanical stirred solution of this solid in MeOH (600 mL) was added sodium methoxide (55.1 g, 1.02 mol) portionwise over 5 minutes. The reaction mixture was heated under reflux for 1 hour, cooled to room temperature, concentrated in vacuo and diluted with water (600 mL). The aqueous mixture was washed with $CH_2Cl_2$ (3×1 L) and acidified to pH 6 using 2 N HCl (475 mL). The resulting precipitate was filtered and the filter cake washed with water (3×250 mL) and diethyl ether (2×200 mL). The solid was dried in a vacuum oven at 45° C. for 18 hours to provide compound 3a (38.7 g, 70%) as a light brown solid.

Example 7

Preparation of Compound 3b

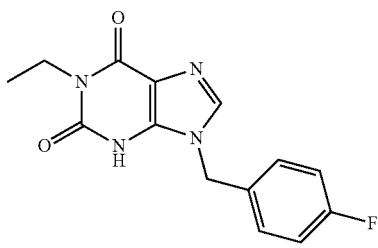

3b

Using the method described in Example 6 and substituting compound 2b for compound 2a, compound 3b was synthesized as an off-white solid.

Example 8

Preparation of Compound 3c

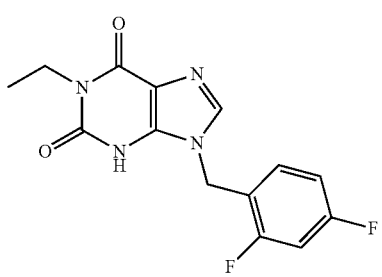

3c

Using the method described in Example 6 and substituting compound 2c for compound 2a, compound 3c was synthesized as an off-white solid.

Example 9

Preparation of Compound 3d

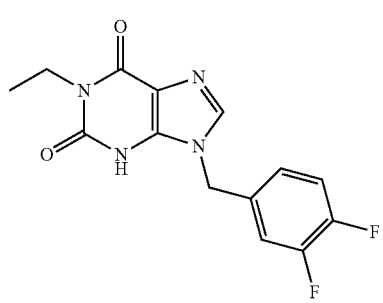

3d

Using the method described in Example 6 and substituting compound 2d for compound 2a, compound 3d was synthesized as an off-white solid.

Example 10

Preparation of Compound 3e

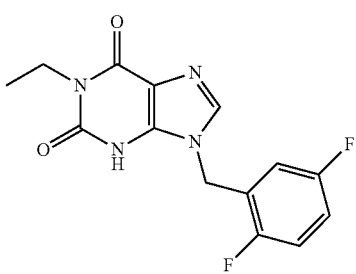

3e

Using the method described in Example 6 and substituting compound 2e for compound 2a, compound 3e was synthesized as an off-white solid.

Example 11

Preparation of Compound 4a

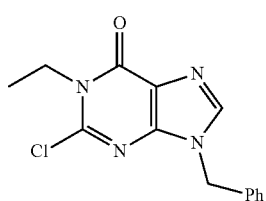

4a

A 1-L three-necked round-bottomed flask equipped with a mechanical stirrer was charged with 9-benzyl-1-ethyl-1H- purine-2,6(3H,9H)-dione (3a) (38.7 g, 0.143 mol) and phosphorus oxychloride (387 mL, 4.15 mol). The mixture was heated under reflux for 18 hours, more phosphorus oxychloride (100 mL, 1.07 mol) was added and the reaction was heated to reflux for an additional 4 hours. The reaction mixture was concentrated in vacuo and the resulting brown oil was carefully poured into a mixture of ice/water (1 L) and $CH_2Cl_2$ (500 mL). After adjustment of the mixture to pH 7-8 using solid $NaHCO_3$, the layers were separated and the aqueous phase was extracted with $CH_2Cl_2$ (3×1 L). The combined organic extracts were dried over $Na_2SO_4$, filtered and concentrated in vacuo. The brown residue was purified using column chromatography (silica gel, 97:3, $CH_2Cl_2$/MeOH) to provide a yellow solid. This solid was further purified using column chromatography (silica gel, 80:20, EtOAc/hexanes) to provide compound 4a (25.2 g, 61%) as a yellow solid.

Example 12

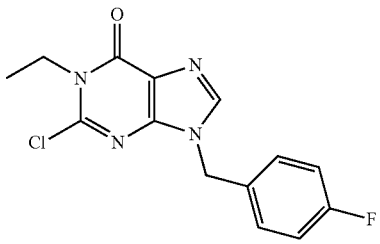

Using the method described in Example 11 and substituting compound 3b for compound 3a, compound 4b was synthesized as a yellow solid.

Example 13

Preparation of Compound 4c

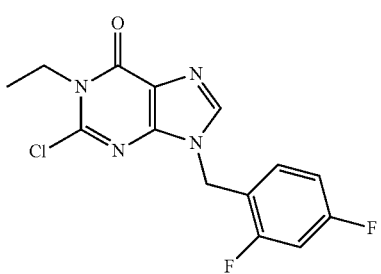

Using the method described in Example 11 and substituting compound 3c for compound 3a, compound 4c was synthesized as a yellow solid.

Example 14

Preparation of Compound 4d

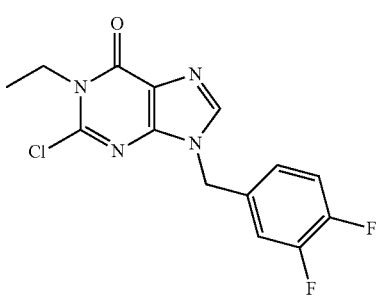

Using the method described in Example 11 and substituting compound 3d for compound 3a, compound 4d was synthesized as a yellow solid.

Example 15

Preparation of Compound 4e

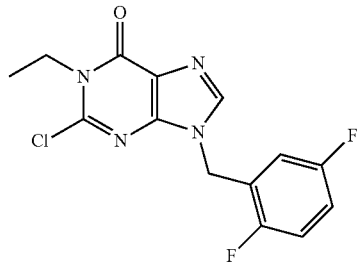

Using the method described in Example 11 and substituting compound 3e for compound 3a, compound 4e was synthesized as a yellow solid.

Example 16

Preparation of Compound 6a

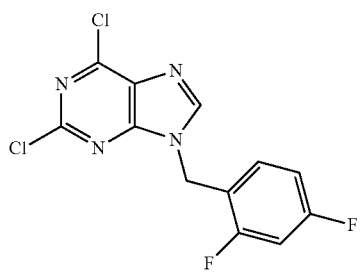

A 2-L three-necked round-bottomed flask equipped with a mechanical stirrer was charged with 2,6-dichloropurine (5) (30.0 g, 0.159 mol), potassium carbonate (110 g, 0.794 mol) and dry DMF (600 mL). The suspension was stirred vigorously as 2,4-difluorobenzyl bromide (39.4 g, 0.190 mol) was added via addition funnel over 0.5 hours. After stirring at room temperature for 18 hours, EtOAc (1 L) and water (1.7 L) was added and the layers separated. The aqueous layer was extracted with EtOAc (2×500 mL) and the combined organic extracts were washed with brine (3×700 mL), dried over $Na_2SO_4$, filtered and concentrated in vacuo. The resulting residue was triturated with EtOAc (200 mL) and stirred for 15 hours. The precipitate was collected, washed with cold 20% EtOAc in hexanes and air-dried overnight to provide compound 6a (16.6 g, 33%) as a white solid. The filtrate was concentrated in vacuo and The residue obtained was purified using CombiFlash chromatography (silica gel, 50:50, hexanes/EtOAc) to provide additional product 6a (14.4 g, 29%) as a white solid.

Example 17

Preparation of Compound 6b

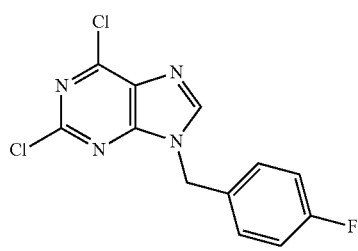

6b

Using the method described in Example 16 and substituting 4-fluorobenzyl bromide for 2,4-difluorobenzyl bromide, compound 6b was synthesized as a white solid.

Example 18

Preparation of Compound 6c

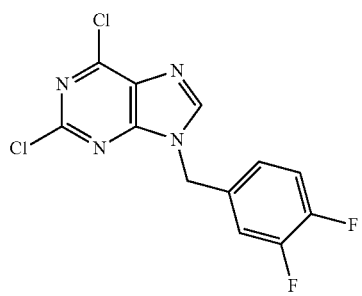

6c

Using the method described in Example 16 and substituting 3,4-difluorobenzyl bromide for 2,4-difluorobenzyl bromide, compound 6b was synthesized as a white solid.

Example 19

Preparation of Compound 7a

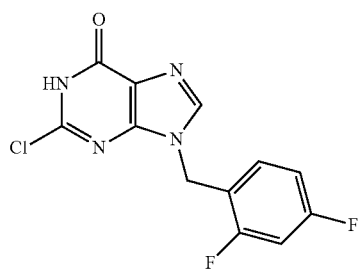

7a

A 2-L three-necked round-bottomed flask equipped with a mechanical stirrer was charged with 2,6-dichloro-9-(2,4-difluorobenzyl)-9H-purine (6a) (31.0 g, 0.098 mol) and 0.2 N NaOH solution (984 mL). The reaction mixture was heated under reflux for 16 hours, filtered while hot through a sintered glass funnel and the filtrate allowed to cool to room temperature. The filtrate was acidified with glacial acetic acid (100 mL) and stirred at 0° C. for 5 hours. The precipitate was collected, washed with cold water (3×200 mL) and air-dried for 1 hour. Further drying in a vacuum oven at 55° C. for 16 hours provided 7a (25.1 g, 86%) as a white solid.

Example 20

Preparation of Compound 7b

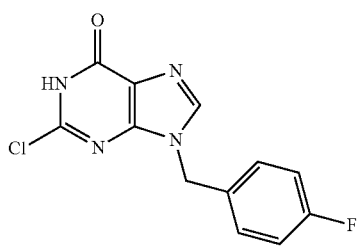

7b

Using the method described in Example 19 and substituting compound 6b for compound 6a, compound 7b was synthesized as an off-white solid.

Example 21

Preparation of Compound 7c

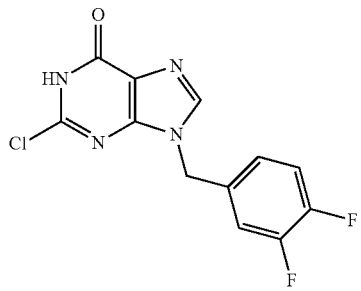

7c

Using the method described in Example 19 and substituting 6c for compound 6a, compound 7c was synthesized as an off-white solid.

Example 22

Preparation of Compound 8a

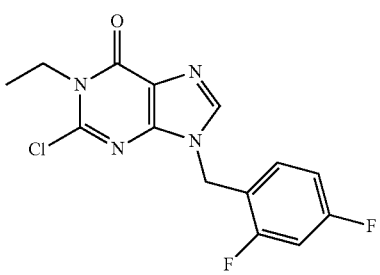

8a

A 2-L three-necked round-bottomed flask equipped with a mechanical stirrer was charged with 2-chloro-9-(2,4-difluorobenzyl)-1H-purin-6(9H)-one (7a) (25.0 g, 0.084 mol), potassium carbonate (58.3 g, 0.421 mol) and N,N-dimethylacetamide (700 mL). The suspension was stirred under an inert atmosphere and iodoethane (15.8 g, 0.101 mol) was added. After stirring 16 hours at room temperature, the mixture was diluted with water (1 L) and then extracted with EtOAc (3×750 mL). The combined organic layers were washed with brine (3×750 mL), dried over $Na_2SO_4$ and filtered. The resulting brown solid was purified using column chromatography (silica gel, 10:90, hexanes, EtOAc) to provide compound 8a (13.4 g, 49%) as an off-white solid.

Example 23

Preparation of Compound 8b

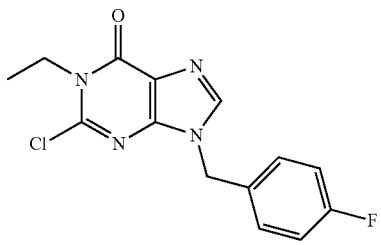

8b

Using the method described in Example 22 and substituting compound 7b for compound 7a, compound 8b was synthesized as an off-white solid.

Example 24

Preparation of Compound 8c

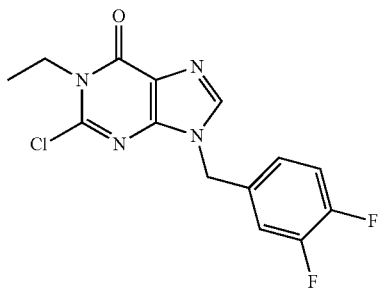

8c

Using the method described in Example 22 and substituting compound 7c for compound 7a, compound 8c was synthesized as an off-white solid.

Example 25

Preparation of Compound 9a

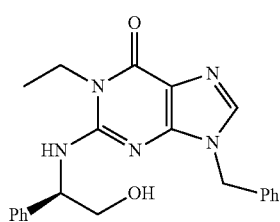

9a

To a stirred solution of 9-benzyl-2-chloro-1-ethyl-1H-purin-6(9H)-one (4a) (925 mg, 3.20 mmol) in NMP (35 mL) under nitrogen atmosphere was added (R)-2-amino-2-phenylethanol (659 mg, 4.80 mmol) and DIPEA (1.1 mL, 6.40 mmol). The reaction mixture was place in an oil bath at 130° C. overnight, cooled to room temperature and poured into ice/water (500 mL). The mixture was stirred for 3 hours and the precipitate was collected and air-dried. The filter cake was dissolved in $CH_2Cl_2$ (200 mL), washed with brine (250 mL) and concentrated in vacuo to provide compound 9a (1.13 g, 90%) as an off-white solid.

Example 26

Preparation of Compound 9b

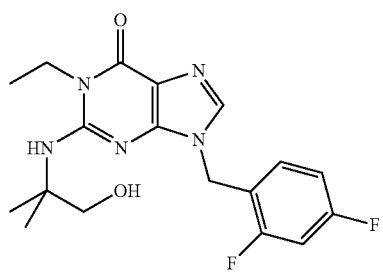

9b

Using the method described in Example 25 and substituting compound 4c for compound 4a, and 2-amino-2,2,-dimethylethanol for (R)-2-amino-2-phenylethanol, compound 9b was synthesized as a light brown solid.

Example 27

Preparation of Compound 9c

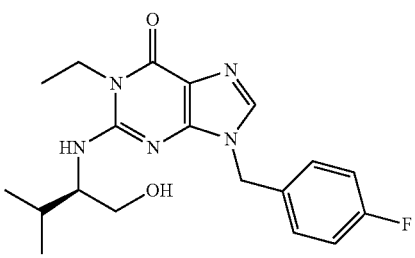

9c

Using the method described in Example 25 and substituting compound 4b for compound 4a, and (R)-2-amino-2-isopropylethanol for (R)-2-amino-2-phenylethanol, compound 9c was synthesized as an off-white solid.

Example 28

Preparation of Compound 9d

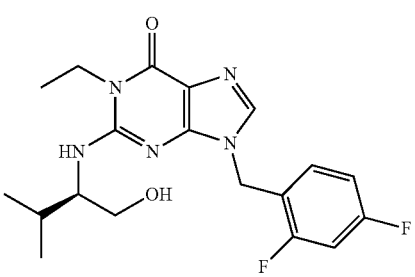

9d

Using the method described in Example 25 and substituting compound 4c for compound 4a, and (R)-2-amino-2-isopropylethanol for (R)-2-amino-2-phenylethanol, compound 9d was synthesized as an off-white solid.

Example 29

Preparation of Compound 9e

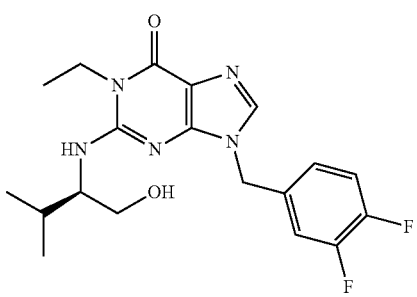
9c

Using the method described in Example 28 and substituting compound 4d for compound 4a, compound 9e was synthesized as an off-white solid.

Example 30

Preparation of Compound 9f

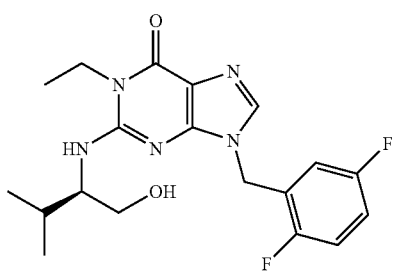
9f

Using the method described in Example 28 and substituting compound 4e for compound 4a, compound 9f was synthesized as an off-white solid.

Example 31

Preparation of Compound 10a

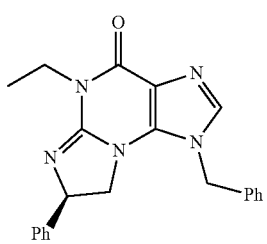
10a

To a stirred solution of (R)-9-benzyl-1-ethyl-2-(2-hydroxy-1-phenylethylamino)-1H-purin-6(9H)-one (9a) (1.13 g, 2.89 mmol) in CH$_2$Cl$_2$ (75 mL) at −10° C. was added thionyl chloride (1.04 g, 8.69 mmol) dropwise. The reaction mixture was stirred at −10° C. for 10 minutes, then allowed to warm to room temperature for 2 hours and concentrated in vacuo. The residue obtained was partitioned between sat. NaHCO$_3$ (100 mL) and CH$_2$Cl$_2$ (100 mL) and the layers separated. The aqueous phase was extracted with CH$_2$Cl$_2$ (100 mL) and the combined organic extracts were dried over Na$_2$SO$_4$, filtered and concentrated in vacuo to provide compound 10a (0.869 g, 81%) as an off-white solid.

Example 32

Preparation of Compound 10b

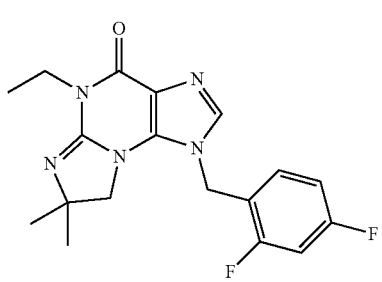
10b

Using the method described in Example 31 and substituting compound 9b for compound 9a, compound 10b was synthesized as an off-white solid.

Example 33

Preparation of Compound 10c

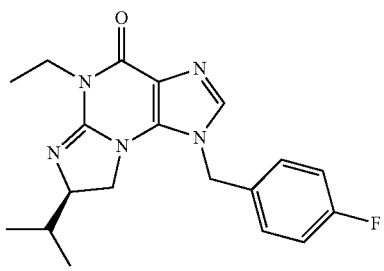
10c

Using the method described in Example 25 and substituting compound 9c for compound 9a, compound 10c was synthesized as an off-white solid.

Example 34

Preparation of Compound 10d

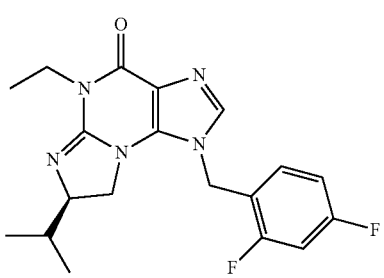
10d

Using the method described in Example 25 and substituting compound 9d for compound 9a, compound 10d was synthesized as an off-white solid.

Example 35

Preparation of Compound 10e

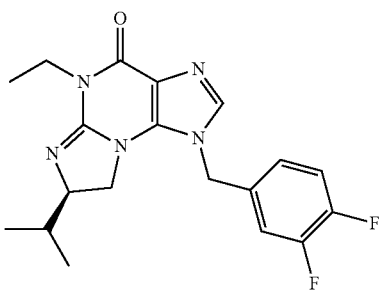

Using the method described in Example 25 and substituting compound 9e for compound 9a, compound 10e was synthesized as an off-white solid.

Example 36

Preparation of Compound 10f

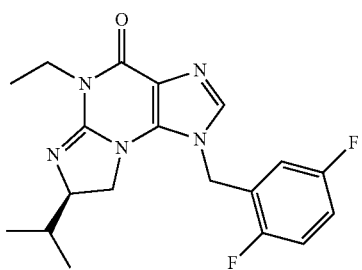

Using the method described in Example 25 and substituting compound 9f for compound 9a, compound 10f was synthesized as an off-white solid.

Example 37

Preparation of Compound 11a

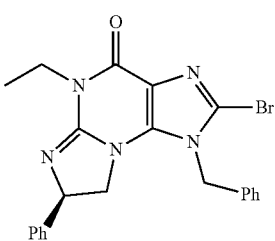

To a stirred solution of (R)-1-benzyl-5-ethyl-7-phenyl-7,8-dihydro-1H-imidazo[2,1-b]purin-4(5H)-one (10a) (0.869 g, 2.34 mmol) in $CH_2Cl_2$ (25 mL) at −10° C. was added N-bromosuccinimide (0.416 g, 2.34 mmol). The reaction mixture was stirred at −10° C. for 2 hours, warmed to room temperature and concentrated in vacuo. The residue obtained was purified using CombiFlash chromatography (silica gel, 80:10, ether/isopropanol) to provide compound 11a (1.10 g, >99%) as an off-white solid.

Example 38

Preparation of Compound 11b

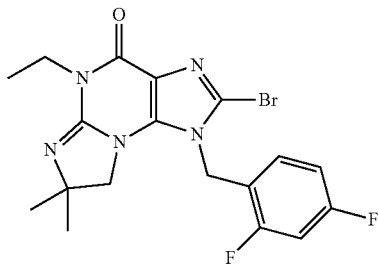

Using the method described in Example 37 and substituting compound 10b for compound 10a, compound 11b was synthesized as an off-white solid.

Example 39

Preparation of Compound 11c

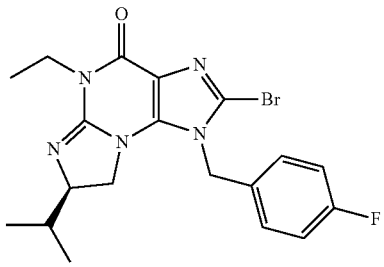

Using the method described in Example 37 and substituting compound 10c for compound 10a, compound 11c was synthesized as an off-white solid.

Example 40

Preparation of Compound 11d

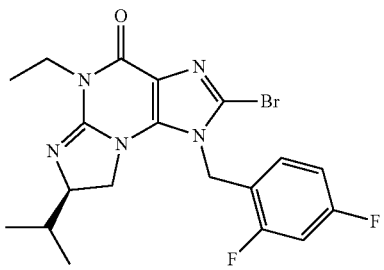

Using the method described in Example 37 and substituting compound 10d for compound 10a, compound 11e was synthesized as an off-white solid.

Example 41

Preparation of Compound 11e

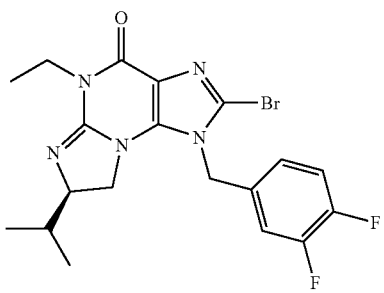
11e

Using the method described in Example 37 and substituting compound 10e for compound 10a, compound 11e was synthesized as an off-white solid.

Example 42

Preparation of Compound 11f

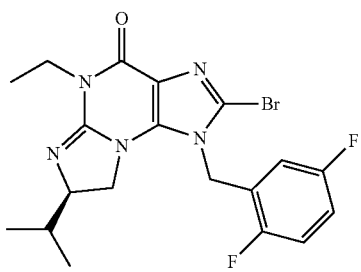
11f

Using the method described in Example 37 and substituting compound 10f for compound 10a, compound 11f was synthesized as an off-white solid.

Example 43

Preparation of Compound 43a

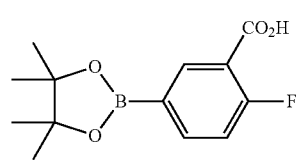
43a

A 100 mL round-bottomed flask, equipped with a Dean-Stark apparatus, was charged with 5-borono-2-fluorobenzoic acid (1.00 g, 5.43 mmol), anhydrous toluene (50 mL) and pinacol (0.706 g, 5.98 mmol). The mixture was heated under reflux for 16 hours, cooled to room temperature, then concentrated in vacuo. The residue obtained was triturated with hexanes (200 mL) to provide compound 43a (1.33 g, 92%) as a white solid.

Example 44

Preparation of Compound 14a

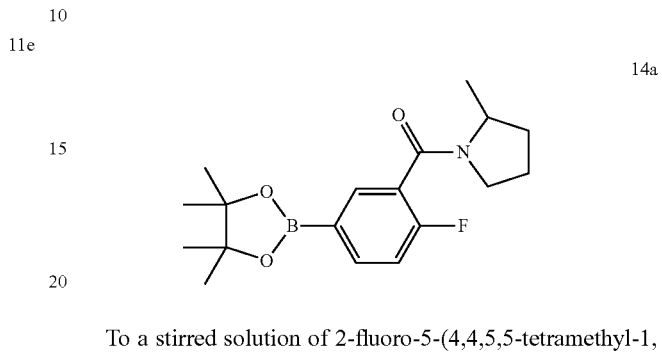
14a

To a stirred solution of 2-fluoro-5-(4,4,5,5-tetramethyl-1,3,2-dioxaborolan-2-yl)benzoic acid (43a) (133 mg, 0.500 mmol) in anhydrous DMF (3 mL) was added HOBt (84 mg, 0.625 mmol), EDC.HCl (120 mg, 0.625 mmol) and DIPEA (162 mg, 1.25 mmol). The reaction mixture was stirred for 30 minutes then 2-methylpyrrolidine (36 mg, 0.416 mmol) was added and the reaction was allowed to stir for an additional 16 hours. The reaction mixture was diluted with EtOAc (30 mL) and sat. $NH_4Cl$ (20 mL) and the layers separated. The aqueous phase was extracted with EtOAc (20 mL) and the combined organic extracts were washed with brine (3×20 mL), dried over $Na_2SO_4$, filtered and concentrated in vacuo to provide compound 14a (146 mg, 87%) as a pale yellow oil.

Example 45

Preparation of Compound 14b

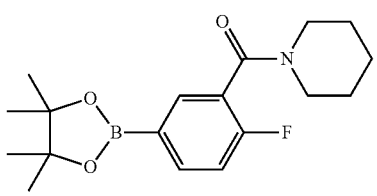
14b

Using the method described in Example 44 and substituting piperidine for 2-methylpyrrolidine, compound 14b was synthesized as a light brown yellow oil.

Example 46

Preparation of Compound 14c

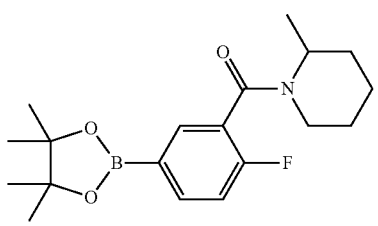
14c

Using the method described in Example 44 and substituting 2-methylpiperidine for 2-methylpyrrolidine, compound 14c was synthesized as a pale yellow oil.

Example 47

Preparation of Compound 47a

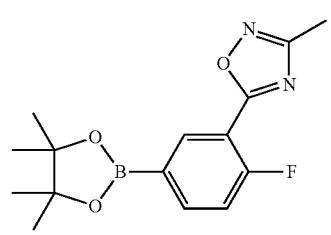

47a

A 10 mL sealed tube was charged with 2-fluoro-5-(4,4,5,5-tetramethyl-1,3,2-dioxaborolan-2-yl)benzoic acid (43a) (200 mg, 0.752 mmol), HOBt (122 mg, 0.902 mmol), EDC.HCl (166 mg, 0.864 mmol), and CH$_3$CN (5 mL). The mixture was stirred at room temperature for 30 minutes and methylamidoxime (56 mg, 902 mmol, see *Organic Process Research & Development* 2006, 10, 36-45) and powdered 4 Å molecular sieves was added. The sealed tube was placed in an oil bath at 85° C. for 2 days, then cooled to room temperature and poured into saturated NaHCO$_3$ (200 mL). The aqueous solution was extracted with EtOAc (2×125 mL) and the combined organic extracts were dried over Na$_2$SO$_4$, filtered and concentrated in vacuo. The crude product was purified using CombiFlash chromatography (silica gel, 50:50, CH$_2$Cl$_2$/EtOAc) to provide compound 47a (86 mg, 38%) as an off-white solid.

Example 48

Preparation of Compound 45

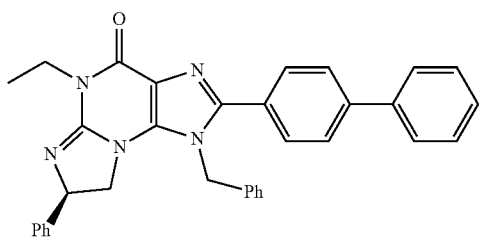

A 10 mL sealed tube was charged with (R)-1-benzyl-2-bromo-5-ethyl-7-phenyl-7,8-dihydro-1H-imidazo[2,1-b]purin-4(5H)-one (11a) (100 mg, 0.222 mmol), biphenyl-4-ylboronic acid (65 mg, 0.333 mmol), Pd(PPh$_3$)$_4$ (25 mg, 0.022 mmol), Na$_2$CO$_3$ (35 mg, 0.333 mmol), argon-degassed dimethoxyethane (2 mL) and argon-degassed water (0.5 mL). The tube was flushed with argon, sealed, and placed in an oil bath at 100° C. and allowed to remain at this temperature for about 15 hours. The reaction mixture was then cooled to room temperature, diluted with brine (5 mL) and CH$_2$Cl$_2$ (5 mL) and the layers separated. The aqueous phase was extracted with CH$_2$Cl$_2$ (5 mL) and the combined organic extracts were dried over Na$_2$SO$_4$, filtered and concentrated in vacuo. The residue obtained was purified using CombiFlash chromatography (silica gel, 95:5, CH$_2$Cl$_2$/MeOH) to provide an oil which was further purified using semi-preparative HPLC (Luna C18, CH$_3$CN/water with 0.05% TFA) to provide a solid. This solid was dissolved in a mixture of CH$_3$CN and water and the resulting solution freeze-dried overnight to provide compound 45 (64 mg, 55%) as a white solid: $^1$H NMR (300 MHz, DMSO-d$_6$) δ 7.80-7.76 (m, 4H), 7.66-7.52 (m, 4H), 7.51-7.43 (m, 2H), 7.42-7.18 (m, 7H), 7.10 (d, J=7.1 Hz, 2H), 5.59-5.39 (m, 2H), 5.09 (t, J=7.7 Hz, 1H), 4.37 (t, J=9.3 Hz, 1H), 4.10-3.87 (m, 2H), 3.81 (t, J=8.2 Hz, 1H), 1.20 (t, J=6.9, 3H); APCI MS m/z 524 [M+H]$^+$.

Example 49

Preparation of Compound 43

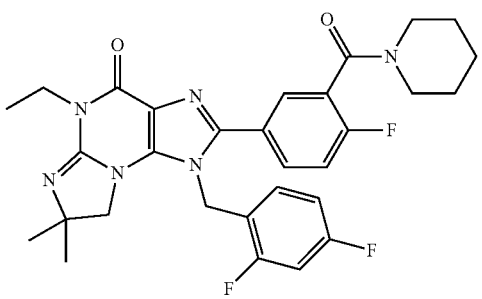

43

Using the method described in Example 48 and substituting compound 11b for compound 11a, and compound 14b for biphenyl-4-ylboronic acid, compound 43 was synthesized as an off-white solid: $^1$H NMR (300 MHz, CDCl$_3$) δ 7.54 (dd, J=6.2, 2.3 Hz, 1H), 7.47-7.40 (m, 1H), 7.12 (t, J=8.7 Hz, 1H), 6.97-6.86 (m, 2H), 6.78-6.68 (m, 1H), 5.28 (s, 2H), 4.08 (q, J=7.0 Hz, 2H), 3.75-3.66 (m, 2H), 3.57 (s, 2H), 3.27-3.20 (m, 2H), 1.70-1.54 (m, 6H), 1.31-1.25 (m, 9H); ESI MS m/z 565 [M+H]$^+$.

Example 50

Preparation of Compound 46

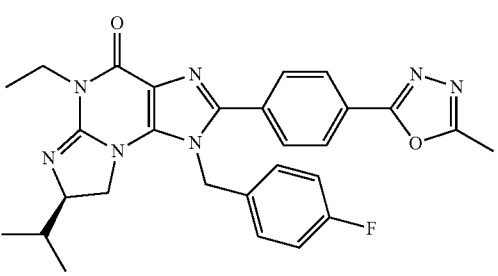

46

Using the method described in Example 48 and substituting compound 11c for compound 11a, and compound 47a for biphenyl-4-ylboronic acid, a crude compound was synthesized as an off-white solid, then dissolved in CH$_3$CN and water and the resulting solution freeze-dried overnight to provide compound 46 (59 mg, 50%) as a white solid: $^1$H NMR (300 MHz, CDCl$_3$) δ 8.04 (d, J=8.6 Hz, 2H), 7.67 (d, J=8.6 Hz, 2H), 7.20-7.12 (m, 2H), 7.11-7.02 (m, 2H), 5.39 (d, J=17.6 Hz, 2H), 4.27-4.13 (m, 1H), 4.09-3.90 (m, 2H), 3.90-3.79 (m, 1H), 3.52 (dd, J=8.0, 6.2 Hz, 1H), 2.62 (s, 3H), 1.80-1.66 (m, 1H), 1.30 (t, J=7.0 Hz, 3H), 0.81 (d, J=6.8 Hz, 3H), 0.72 (d, J=6.8 Hz, 3H); ESI MS m/z 514 [M+H]$^+$.

Example 51

Preparation of Compound 16

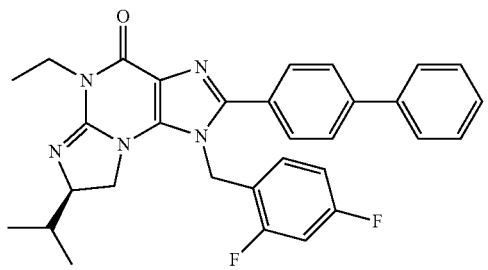

16

Using the method described in Example 48 and substituting compound 11d for compound 11a, compound 16 was synthesized as an off-white solid: $^1$H NMR (300 MHz, CDCl$_3$) δ 7.65-7.57 (m, 6H), 7.47-7.42 (m, 3H), 6.95-6.85 (m, 3H), 5.40 (s, 2H), 4.24-4.17 (m, 1H), 4.04-3.93 (m, 2H), 3.89-3.83 (m, 1H), 3.54 (dd, J=7.8, 6.2 Hz, 1H), 1.79-1.72 (m, 1H), 1.30 (t, J=7.0 Hz, 3H), 0.84 (d, J=6.8 Hz, 3H), 0.74 (d, J=6.8 Hz, 3H); APCI MS m/z 526 [M+H]$^+$.

Example 52

Preparation of Compound 47

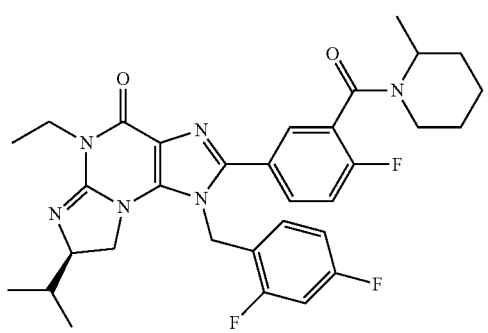

47

Using the method described in Example 48 and substituting substituting compound 11d for compound 11a, and compound 14c for biphenyl-4-ylboronic acid, a residue was obtained as an off-white solid. The residue obtained was purified using CombiFlash chromatography (silica gel, 90:10 CH$_2$Cl$_2$/MeOH) to provide a crude oil which was further purified using semi-preparative HPLC (Luna C18, CH$_3$CN/water with 0.05% TFA) to provide an oil. This oil was dissolved in CH$_3$CN and water and the resulting solution freeze-dried overnight to provide compound 47 (74 mg, 35%) as a white solid: $^1$H NMR (300 MHz, CDCl$_3$) δ 7.60-7.47 (m, 2H), 7.17-7.07 (m, 1H), 6.96-6.87 (m, 2H), 6.71 (m, 1H), 5.31 (s, 2H), 5.01-4.54 (m, 1H), 4.24-4.13 (m, 1H), 4.03-3.77 (m, 4H), 3.54 (m, 1H), 3.24-2.76 (m, 2H), 1.78-1.60 (m, 6H), 1.31-1.24 (m, 6H), 0.94 (d, J=6.6 Hz, 3H), 0.74 (d, J=6.6 Hz, 3H); ESI MS m/z 593 [M+H]$^+$.

Example 53

Preparation of Compound 48

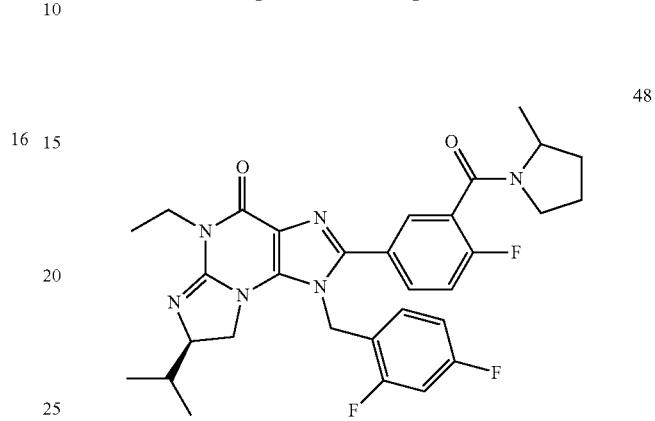

48

Using the method described in Example 48 and substituting compound 11d for compound 11a, and compound 14a for biphenyl-4-ylboronic acid a residue was obtained as an off-white solid. The residue obtained was purified using CombiFlash chromatography (silica gel, 90:10 CH$_2$Cl$_2$/MeOH) to provide a crude oil which was further purified using semi-preparative HPLC (Luna C18, CH$_3$CN/water with 0.05% TFA) to provide a colorless oil. This oil was dissolved in CH$_3$CN and water and the resulting solution freeze-dried overnight to provide compound 48 (67 mg, 31%) as an off-white solid: $^1$H NMR (300 MHz, CDCl$_3$) δ 7.63-7.41 (m, 2H), 7.15-7.11 (m, 1H), 6.95-6.89 (m, 2H), 6.88-6.72 (m, 1H), 5.32 (s, 2H), 4.32-4.15 (m, 2H), 4.04-3.83 (m, 3H), 3.70-3.35 (m, 3H), 2.13-1.72 (m, 4H), 1.33-1.26 (m, 6H), 0.91-0.73 (M, 7H); ESI MS m/z 579 [M+H]$^+$.

Example 54

Preparation of Compound 49

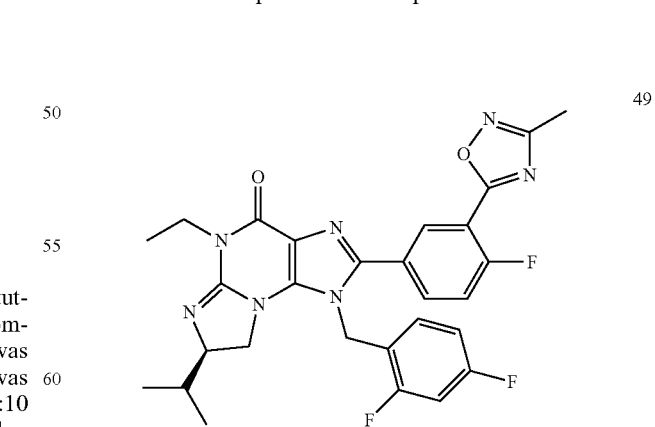

49

Using the method described in Example 48 and substituting substituting compound 11d for compound 11a, and compound 47a for biphenyl-4-ylboronic acid, a residue was obtained as an off-white solid. The residue obtained was purified using CombiFlash chromatography (silica gel, 97:3 CH$_2$Cl$_2$/MeOH) to provide a crude oil which was further purified using semi-preparative HPLC (Luna C18, CH$_3$CN/water with 0.05% TFA) to provide a solid. This solid was dissolved in CH$_3$CN and water and the resulting solution freeze-dried overnight to provide compound 49 (40 mg, 33%) as an off-white solid: $^1$H NMR (300 MHz, CDCl$_3$) δ 8.20 (dd, J=6.5, 2.3 Hz, 1H), 7.85-7.77 (m, 1H), 7.33 (dd, J=9.8, 8.9 Hz, 1H), 7.01-6.89 (m, 2H), 6.85-6.74 (m, 1H), 5.38 (s, 2H), 4.29-4.13 (m, 1H), 4.07-3.86 (m, 3H), 3.60 (dd, J=7.6, 6.4 Hz, 1H), 2.47 (s, 3H), 1.85-1.71 (m, 1H), 1.31 (t, J=7.0 Hz, 3H), 0.87 (d, J=6.8 Hz, 3H), 0.78 (d, J=6.8 Hz, 3H); ESI MS m/z 550 [M+H]$^+$.

Example 55

Preparation of Compound 50

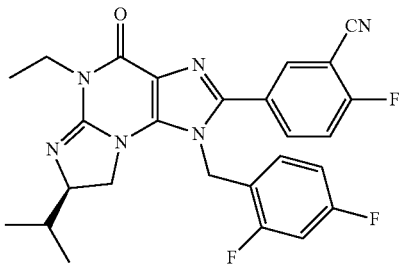

Using the method described in Example 48 and substituting substituting compound 11d for compound 11a, and 3-cyano-4-fluorophenylboronic acid for biphenyl-4-ylboronic acid, a residue was obtained as an off-white solid. The residue obtained was purified using CombiFlash chromatography (silica gel, 1:3 CH$_2$Cl$_2$/EtOAc) to provide compound 50 (280 mg, 80%) as an off-white solid.

Example 56

Preparation of Compound 51

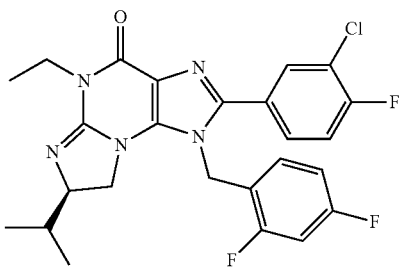

Using the method described in Example 48 and substituting compound 11d for compound 11a, and 3-chloro-4-fluorophenylboronic acid for biphenyl-4-ylboronic acid, a residue was obtained as yellow solid. The residue obtained was purified using CombiFlash chromatography (silica gel, 95:5 CH$_2$Cl$_2$/MeOH) to provide compound 51 (1.50 g, 79%) as a light yellow solid.

Example 57

Preparation of Compound 52

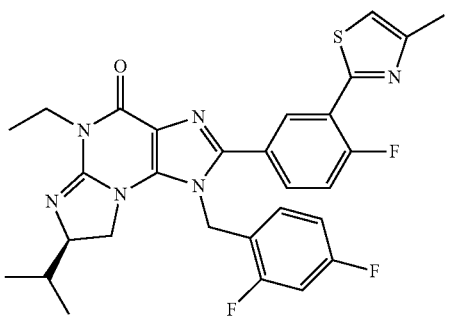

A 10 mL microwave vial was charged with (R)-5-(1-(2,4-difluorobenzyl)-5-ethyl-7-isopropyl-4-oxo-4,5,7,8-tetrahydro-1H-imidazo[2,1-b]purin-2-yl)-2-fluorobenzonitrile (50) (275 mg, 0.558 mmol), MeOH (5 mL), and ammonium sulfide solution in water (20 wt %, 600 μL, 1.67 mmol). The reaction mixture was stirred in a microwave at 85° C. for 15 minutes, cooled to room temperature and concentrated in vacuo. The residue obtained was diluted with EtOAc (200 mL) and brine (250 mL) and the layers separated. The aqueous phase was extracted with EtOAc (200 mL) and the combined organic extracts were dried over Na$_2$SO$_4$, filtered and concentrated in vacuo. The crude product was purified using CombiFlash chromatography (silica gel, 96:4, CH$_2$Cl$_2$/MeOH) to provide (R)-5-(1-(2,4-difluorobenzyl)-5-ethyl-7-isopropyl-4-oxo-4,5,7,8-tetrahydro-1H-imidazo[2,1-b]purin-2-yl)-2-fluorobenzothioamide (118 mg, 40%) as a yellow solid.

A 10 mL sealed tube was charged with the above thioamide (115 mg, 0.218 mmol), CH$_3$CN (5 mL) and chloroacetone (19 μL, 0.240 mmol). The sealed tube was placed in an oil bath at 85° C. for 16 hours, then cooled to room temperature and diluted with CH$_2$Cl$_2$ (100 mL) and brine (200 mL). After separating the layers, the aqueous phase was extracted with CH$_2$Cl$_2$ (100 mL) and the combined organic extracts were dried over Na$_2$SO$_4$, filtered and concentrated in vacuo. The crude product was purified using CombiFlash chromatography (silica gel, 96:4, CH$_2$Cl$_2$/MeOH) and semi-preparative HPLC (Luna C18, CH$_3$CN/water with 0.05% TFA) to provide a solid. This solid was dissolved in a mixture of CH$_3$CN and water and the resulting solution freeze-dried overnight to provide compound 52 (46 mg, 37%) as a white solid: $^1$H NMR (300 MHz, CDCl$_3$) δ 8.38 (dd, J=6.9, 2.4 Hz, 1H), 7.71-7.63 (m, 1H), 7.30-7.19 (m, 1H), 7.02-6.89 (m, 3H), 6.88-6.77 (m, 1H), 5.40 (s, 2H), 4.28-4.14 (m, 1H), 4.09-3.94 (m, 2H), 3.95-3.85 (m, 1H), 3.59 (dd, J=7.7, 6.3 Hz, 1H), 2.43

(s, 3H), 1.85-1.71 (m, 1H), 1.31 (t, J=7.0 Hz, 3H), 0.86 (d, J=6.8 Hz, 3H), 0.77 (d, J=6.8 Hz, 3H); ESI MS m/z 565 [M+H]⁺.

Example 58

Preparation of Compound 53

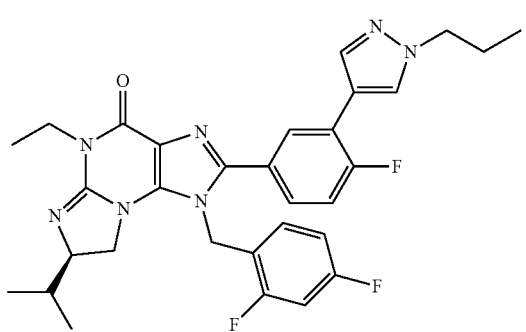

A 10 mL sealed tube was charged with (R)-2-(3-chloro-4-fluorophenyl)-1-(2,4-difluorobenzyl)-5-ethyl-7-isopropyl-7,8-dihydro-1H-imidazo[2,1-b]purin-4(5H)-one (51) (150 mg, 0.299 mmol), 1-propyl-4-(4,4,5,5-tetramethyl)-1,3,2-dioxaborolan-2-yl (106 mg, 0.448 mmol), $K_3PO_4$ (127 mg, 0.598 mmol), $Pd_2(dba)_3$ (2.74 mg, 2.99 µmol), X-Phos (5.70 mg, 12.0 µmol), and argon-degassed n-butanol (1.2 mL). The tube was placed in an oil bath at 100° C. for 16 hours, cooled to room temperature and diluted with $CH_2Cl_2$ (250 mL). The organic mixture was washed with brine (2×100 mL), dried over $Na_2SO_4$, filtered and concentrated in vacuo. The residue obtained was purified using CombiFlash chromatography (silica gel, 50:50, hexanes/EtOAc) to provide a crude oil. This oil was dissolved in a mixture of $CH_3CN$ and water and the resulting solution freeze-dried overnight to provide compound 53 (52 mg, 30%) as a white solid: ¹H NMR (300 MHz, DMSO-d₆) δ 8.11 (d, J=1.8 Hz, 1H), 7.78-7.68 (m, 2H), 7.40-7.22 (m, 3H), 7.12-6.96 (m, 2H), 5.46 (s, 2H), 4.17-3.80 (m, 6H), 3.77-3.64 (m, 1H), 1.89-1.73 (m, 2H), 1.72-1.58 (m, 1H), 1.17 (t, J=6.9 Hz, 3H), 0.88-0.79 (m, 6H), 0.75 (d, J=6.6 Hz, 3H); ESI MS m/z 576 [M+H]⁺.

Example 59

Preparation of Compound 54

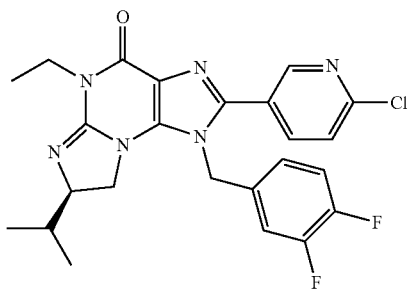

The title compound was prepared from (R)-2-bromo-1-(3,4-difluorobenzyl)-5-ethyl-7-isopropyl-7,8-dihydro-1H-imidazo[2,1-b]purin-4(5H)-one (11e) (500 mg, 1.11 mmol) and 2-chloropyridine-5-boronic acid (174 mg, 1.11 mmol) heating for 6 hours according to the procedure described in Example 48. The residue obtained was purified using CombiFlash chromatography (silica gel, 95:5, $CH_2Cl_2$/MeOH) and semi-preparative HPLC (Luna C18, $CH_3CN$/water with 0.05% TFA) to provide a solid. This solid was dissolved in a mixture of $CH_3CN$ and water and the resulting solution freeze-dried overnight to provide compound 54 (160 mg, 30%) as a white solid: ¹H NMR (300 MHz, CDCl₃) δ 8.43 (d, J=2.0 Hz, 1H), 7.91 (dd, J=8.3, 2.5 Hz, 1H), 7.39 (d, J=8.3 Hz, 1H), 7.30-7.20 (m, 1H), 6.97-6.87 (m, 1H), 6.83-6.74 (m, 1H), 5.41-5.29 (m, 2H), 4.27-4.13 (m, 1H), 4.07-3.92 (m, 2H), 3.84 (dd, J=9.6, 8.1 Hz, 1H), 3.53 (dd, J=8.0, 6.6 Hz, 1H), 1.84-1.69 (m, 1H), 1.30 (t, J=7.0 Hz, 3H), 0.85 (d, J=6.8 Hz, 3H), 0.77 (d, J=6.8 Hz, 3H); ESI MS m/z. 485 [M+H]⁺.

Example 60

Preparation of Compound 55

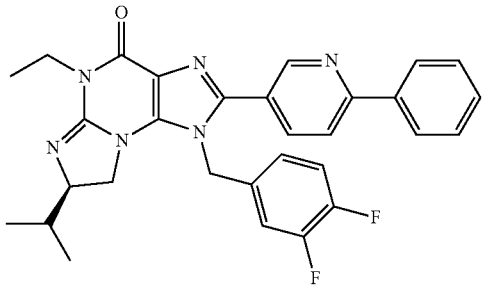

The title compound was prepared from (R)-2-(6-chloropyridin-3-yl)-1-(3,4-difluorobenzyl)-5-ethyl-7-isopropyl-7,8-dihydro-1H-imidazo[2,1-b]purin-4(5H)-one (54) (65 mg, 0.134 mmol) and phenylboronic acid (20 mg, 0.161 mmol) heating for 4 hours according to the procedure described in Example 48. The residue obtained was purified using CombiFlash chromatography (silica gel, 96:4, $CH_2Cl_2$/MeOH) to provide a solid. The solid was dissolved in a mixture of $CH_3CN$ and water and the resulting solution freeze-dried overnight to provide compound 23 (61 mg, 86%) as a yellow solid: ¹H NMR (300 MHz, CDCl₃) δ 8.72 (d, J=1.8 Hz, 1H), 8.07-7.97 (m, 3H), 7.81 (d, J=8.3 Hz, 1H), 7.53-7.42 (m, 3H), 7.33-7.21 (m, 1H), 7.01-6.91 (m, 1H), 6.87-6.79 (m, 1H), 5.39 (d, J=18.0 Hz, 2H), 4.29-4.15 (m, 1H), 4.10-3.92 (m, 2H), 3.85 (t, J=8.8 Hz, 1H), 3.59-3.49 (m, 1H), 1.82-1.69 (m, 1H), 1.31 (t, J=7.0 Hz, 3H), 0.85 (d, J=6.8 Hz, 3H), 0.76 (d, J=6.8 Hz, 3H); ESI MS m/z 527 [M+H]⁺.

Example 61

Preparation of Compound 18

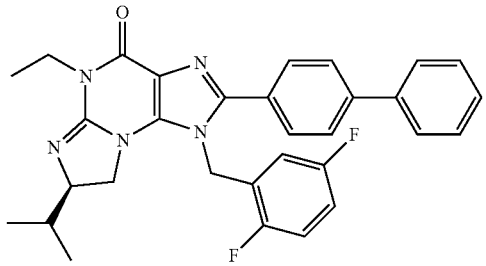

The title compound was prepared from (R)-2-bromo-1-(2,5-difluorobenzyl)-5-ethyl-7-isopropyl-7,8-dihydro-1H-imidazo[2,1-b]purin-4(5H)-one (110 (91 mg, 0.200 mmol) and biphenyl-4-ylboronic acid (48 mg, 0.240 mmol) heating for 3 hours according to the procedure described in Example 48. The residue obtained was purified using CombiFlash chromatography (silica gel, 95:5 CH$_2$Cl$_2$/MeOH) to provide a solid. The solid was dissolved in a mixture of CH$_3$CN and water and the resulting solution freeze-dried overnight to provide compound 18 (57 mg, 54%) as a white solid: $^1$H NMR (300 MHz, CDCl$_3$) δ 7.63-7.58 (m, 6H), 7.44-7.36 (m, 3H), 7.08 (m, 2H), 6.58 (m, 1H), 5.42 (s, 2H), 4.24-4.05 (m, 1H), 4.03-3.93 (m, 2H), 3.89-3.83 (m, 1H), 3.54 (dd, J=7.8, 6.3 Hz, 1H), 1.79-1.72 (m, 1H), 1.30 (t, J=7.0 Hz, 3H), 0.84 (d, J=6.7 Hz, 3H), 0.74 (d, J=6.7 Hz, 3H); ESI MS m/z 526 [M+H]$^+$.

Example 62

Preparation of Compound 62A

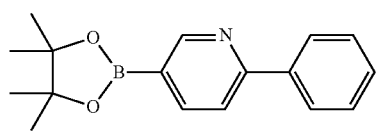
62A

Step A—Preparation of 5-Chloro-2-phenylpyridine

A 100-mL, round-bottomed flask, fitted with a reflux condenser was charged with 2,5-dichloropyridine (1.00 g, 6.76 mmol), phenylboronic acid (1.07 g, 8.78 mmol), [1,4-bis(diphenylphosphino)butane]palladium(II) dichloride (0.204 g, 0.338 mmol), argon-degassed toluene/ethanol (4:1, 17 mL) and argon-degassed aqueous 1 N sodium carbonate (6.6 mL). The mixture was heated to reflux for 3 h, cooled to room temperature and diluted with water (15 mL) and EtOAc (100 mL). The layers separated and the aqueous phase was extracted with EtOAc (100 mL). The combine organic extracts were dried over Na$_2$SO$_4$, filtered and concentrated. Purification by flash column chromatography (silica gel, 50:50 hexanes/CH$_2$Cl$_2$) provided 5-chloro-2-phenylpyridine (0.959 g, 75%) as a white solid.

Step B—Preparation of Compound 62A

A 150 mL sealed tube was charged with bis(dibenzylideneacetone)palladium (87 mg, 0.152 mmol), tricyclohexylphosphine (102 mg, 0.364 mmol) and nitrogen-degassed 1,4-dioxane (32 mL). After stirring at room temperature for 30 min under nitrogen, bis(pinacolato)diboron (1.41 g, 5.56 mmol), KOAc (0.744 g, 7.59 mmol) and 5-chloro-2-phenylpyridine (0.959 g, 5.06 mmol, from Step A)=was added to the reaction mixture. The tube was sealed and place in an oil bath at 80° C. for 16 h. The mixture was cooled to room temperature, diluted with brine (50 mL) and CH$_2$Cl$_2$ (100 mL) and the layers were separated. The aqueous phase was extracted with CH$_2$Cl$_2$ (100 mL) 4nd the combined organics washed with brine (150 mL), dried over Na$_2$SO$_4$, filtered and concentrated. Purification by flash column chromatography (silica gel, 50:50 CH$_2$Cl$_2$/EtOAc) provided compound 62A (0.569 g, 40%) as a white solid.

Example 63

Preparation of Compound 60

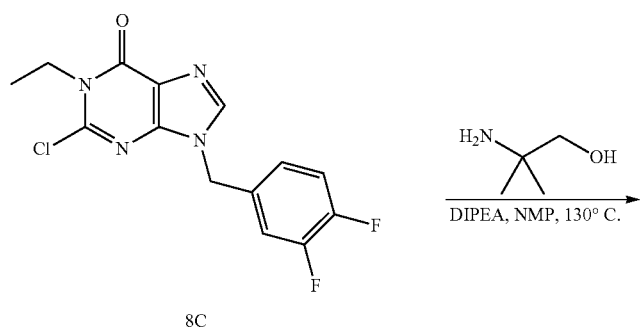
8C

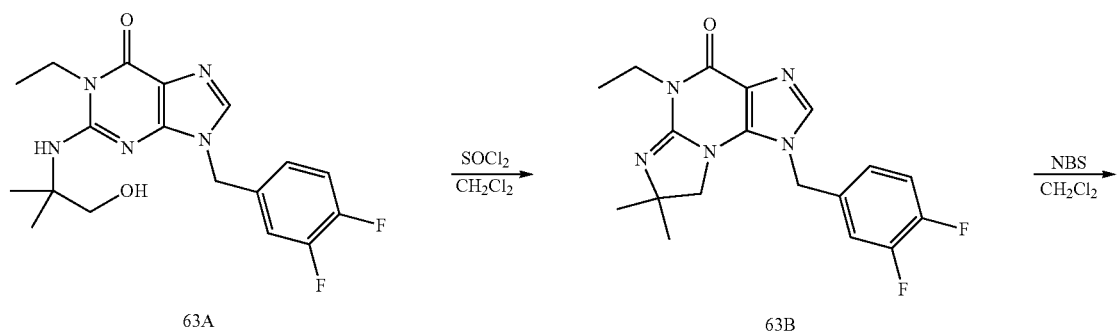
63A     63B

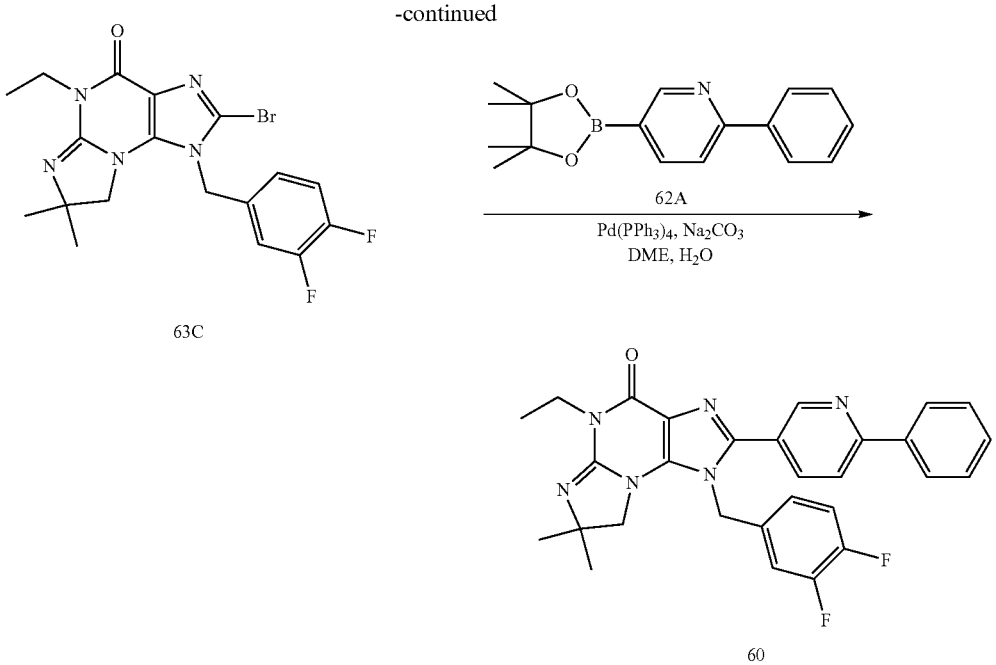

Step A—Preparation of Compound 63A

To a stirred solution of compound 8C (6.70 g, 20.6 mmol) in NMP (125 mL) was added 2-amino-2-methylpropan-1-ol (4.59 g, 51.5 mmol) and DIPEA (8.00 g, 61.9 mmol). The resulting reaction was heated to 130° C. and allowed to stir at this temperature for 16 hours, then cooled to room temperature and poured into water (500 mL). The resulting solution was stirred for 3 hours and the precipitate formed was collected by filtration, washed with water (200 mL) and air-dried for 1 hour. Further drying in a vacuum oven at 50° C. provided compound 63A (6.62 g, 85%) as a white solid.

Step B—Preparation of Compound 63B

To a stirred solution of compound 63A (6.62 g, 17.5 mmol) in $CH_2Cl_2$ (400 mL) was added thionyl chloride (6.26 g, 52.6 mmol). The resulting reaction was stirred at room temperature for 20 hours, then concentrated in vacuo and the residue obtained was partitioned between saturated $NaHCO_3$ (400 mL) and $CH_2Cl_2$ (400 mL). The layers were separated and the aqueous phase was extracted with $CH_2Cl_2$ (3×200 mL). The combined organic extracts were dried over $Na_2SO_4$, filtered and concentrated in vacuo to provide compound 63B (6.85 g, >99%) as a white solid.

Step C—Preparation of Compound 63C

To a stirred solution of compound 63B (6.85 g, 19.0 mmol) in $CH_2Cl_2$ (240 mL) was added NBS (3.39 g, 19.0 mmol). The resulting reaction was allowed to stir for 3 hours at room temperature, then was diluted with brine (200 mL) and the layers were separated. The organic phase was washed with brine (3×100 mL), dried over $Na_2SO_4$, filtered and concentrated in vacuo. The resulting residue was purified using flash column chromatography (silica gel, 95:5 $CH_2Cl_2$/MeOH) to provide compound 63C (7.15 g, 93%) as a white solid.

Step D—Preparation of Compound 60

A 10 mL sealed tube was charged with compound 63C (110 mg, 0.251 mmol), compound 62A (85 mg, 0.301 mmol, from Example 62), $Na_2CO_3$ (53 mg, 0.502 mmol), $Pd(PPh_3)_4$ (29 mg, 0.025 mmol) and argon-degassed dimethoxyethane/water (2:1, 5 mL). The tube was placed in an oil bath at 100° C. and allowed to remain at this temperature for 16 hours, then the tube was removed from the heat bath and allowed to cool room temperature. The cooled reaction mixture was diluted with brine (50 mL) and $CH_2Cl_2$ (50 mL), then separated and the aqueous phase was extracted with $CH_2Cl_2$ (2×50 mL). The combined organic extracts were dried over $Na_2SO_4$, filtered and concentrated in vacuo. The residue obtained was purified using flash column chromatography (silica gel, 20:80, $CH_2Cl_2$/EtOAc) to provide a crude oil which was further purified using semi-preparative HPLC (Luna C18, $CH_3CN$/water with 0.05% TFA) to provide a solid product. This solid product was dissolved in a mixture of $CH_3CN$ and water and the resulting solution was freeze-dried for about 15 hours to provide compound 60 (49 mg, 38%) as an off-white solid: m.p. 124-128° C.; $^1H$ NMR (300 MHz, $CDCl_3$) δ 8.70 (s, 1H), 8.03-7.98 (m, 3H), 7.80 (d, J=8.4 Hz, 1H), 7.50-7.44 (m, 3H), 7.28 (m, 1H), 6.98-6.93 (m, 1H), 6.84-6.81 (m, 1H), 5.36 (s, 2H), 4.09 (q, J=6.9 Hz, 2H), 3.55 (s, 2H), 1.30 (t, J=6.9 Hz, 3H), 1.25 (s, 6H); ESI MS m/z 513 $[M+H]^+$.

Example 64

$P2X_7$ Inhibition Assay

The ability of the PDGs to inhibit $P2X_7$ inhibitory can be determined using a $P2X_7$-HEK-293 stable cell line in $Ca^{++}$ flux assay that can be carried out as described in Cheewatrakoolpong et al., *Biochem. Biophys. Res. Commun.* 332:17-27 (2005).

Using this method, illustrative Polycyclic Guanine Derivatives of the present invention were tested and measured $IC_{50}$ values ranged from about 10 nM to about 1 mM.

Example 65

Whole Blood IL-1β Assay

Selected Polycyclic Guanine Derivatives were assessed for their ability to inhibit ATP-mediated IL-1β production in LPS-stimulated whole blood cultures. Test compounds (10 μl) were diluted in RPMI containing 20 mM HEPES and DMSO and the resulting solutions were then added to human or mouse whole blood (80 μl) in 96-well plates and incubated for 30 minutes at 37° C. The final DMSO concentration did not exceed 0.5%. LPS was added (5 μl) for a final concentration of 200 ng/ml and blood was incubated for 3 hours at 37° C. ATP was added (50 and blood was incubated for 2 hours. Following the addition of RPMI/HEPES (100 μl), the plates were centrifuged and the resulting supernatants were collected. IL-1β concentrations were then measured using commercially available ELISA kits. This assay was also performed as described above using rat blood in place of human or mouse, with the modification that rat blood was used at a final concentration of 50%, DMSO did not exceed 0.125% and 3'-O-(4-benzoyl)benzoyl ATP was used instead of ATP.

Using this method, illustrative Polycyclic Guanine Derivatives of the present invention were tested and results indicate that the Polycyclic Guanine Derivatives are inhibitors of IL-1β levels with inhibition of as great as 98% being attained in this model.

Example 66

Rheumatoid Arthritis Model

Anti-collagen antibody-induced arthritis was induced essentially as described in Terato et al., *Autoimmunity* 22:137-147 (1995) and Terato et al., *J. Immunol.* 148:2103-2108 (1992). In our studies, female BALB/cJ mice (Jackson Laboratory, Bar Harbor, Me.) at 6-8 weeks of age were injected i.p. with 4 mg of an anti-collagen antibody mixture (MD Biosciences, St. Paul, Minn.) and then injected i.p. with 50 mg LPS (MD Biosciences) three days later to induce arthritis.

Using this method, illustrative Polycyclic Guanine Derivatives of the present invention were tested and results show that the Polycyclic Guanine Derivatives inhibit the development of anti-collagen antibody-induced arthritis in an accepted animal model and accordingly, are useful for treating or preventing rheumatoid arthritis.

Example 67

Monoiodoacetate (MIA)-Induced Osteoarthritis Model

Monoiodoacetate-induced osteoarthritis pain was induced using the method described in Bove et al., *Osteoarthritis Cartilage* 11:821-830 (2003). Briefly, the model was initiated by a single injection of 1 mg MIA (Sigma) into the right knee joint of male Wistar rat (Charles River) at 150-175 g. The left knee was injected similarly with saline as control. The difference in weight-bearing between left and right hind limbs was measured with an incapacitance tester (Linton Instrumentation) as a readout for pain. Five 5-second readings were recorded when the rat was in the proper position in the chamber. Before the actual experiment was carried out on day 14 after MIA injection, rats were subjected to at least 2 training sessions for weight-bearing measurements. The efficacy of selected Polycyclic Guanine Derivatives was determined by calculating the difference in weight-bearing readouts between pre- and post-dosing.

Using this method, illustrative Polycyclic Guanine Derivatives of the present invention were tested and results show that the Polycyclic Guanine Derivatives inhibit the weight-bearing response up to about 50% with some test compounds showing efficacy equal to that of celecoxib and naproxen. Accordingly, the Polycyclic Guanine Derivatives are useful for treating osteoarthritis.

Example 68

Cigarette Smoke-Induced Mouse Model of COPD

Female AKR/J mice (6-7 wk old) were exposed nose-only to room air or cigarette smoke (600 mg/m$^3$ total suspended particulate). Mice received two 1-hour exposures, 3 hours apart, for three consecutive days. Test compounds were dosed p.o. in 0.4% methylcellulose. On the fourth day, the test animals were sacrificed and their lungs were lavaged with saline. Total cell number and differential cell counts were determined in the lavage fluid. The efficacy of a test compound was determined by the difference in lung lavage cell counts between smoke-exposed mice treated with compound and smoke-exposed mice treated with vehicle.

Using this method, illustrative Polycyclic Guanine Derivatives of the present invention were tested and shown to inhibit cell infiltration into the lungs of the test animals. Accordingly, the Polycyclic Guanine Derivatives are useful for treating COPD.

Example 69

L5 and L6 Spinal Nerve Ligation (SNL) of the Rat Sciatic Nerve

Peripheral neuropathy was caused by ligating the L5 and L6 spinal nerves of the right sciatic nerve as described (Kim, S. H. et al., *Pain* 50:355-363) with modifications. Briefly, male Sprague Dawley rats (125-150 g, Charles River) were anaesthetized with chloral hydrate (400 mg/kg, i.p.), placed in a prone position and the right paraspinal muscles separated from the spinal processes at the L4-S2 levels. The L5 transverse process was carefully removed so as to identify the L4-L5 spinal nerves. The right L5 and L6 spinal nerves were isolated and tightly ligated with 7/0 silk thread. Complete hemostasis was confirmed and the wound sutured.

Example 70

Induction of Diabetes in Rats

Insulin-dependent diabetes was induced through chemical pancreatectomy (Xiong, Y., et al., *Life Sci.* 77:149-159) by a single injection of streptozocin (STZ; 60 mg/kg, i.p.) dissolved in 0.05 M citrate buffer pH 4.5, in male Sprague Dawley rats (Harlan; 175-200 g; food and water ad libitum before STZ injection). Diabetes was confirmed one week later by measurement of blood glucose levels with a glucose-oxidase test strip and a reflectance meter (Optium Xceed, Abbott) on a sample of blood obtained from a tail prick. Only rats with blood glucose levels >300 mg/dl were recruited into pharmacological studies.

Example 71

Chronic Constriction Injury (CCI) of the Sciatic Nerve in Rats

Surgery was performed according to the method described by Bennett & Xie (Bennett, G. J. et al, *Pain* 33:87-107). Male Sprague Dawley rats (150-175 g, Charles River) were anaesthetized with chloral hydrate (400 mg/kg, i.p.) and the common sciatic nerve was exposed at the level of the mid-thigh. At about 1 cm, proximally to the nerve trifurcation, four loose ligatures (4/0 silk), 1 mm spaced, were tied around the nerve such that the circulation through the superficial epineural vasculature was retarded but did not arrest. All operations were completed by closing the muscle in layers and allowing the animals to recover for 7 days.

Example 72

Measurement of Tactile Allodynia in SNL and STZ-Induced Diabetic Neuropathy Models Behavioral tests were conducted during the light cycle to avoid circadian rhythm fluctuation, by an observer blinded to the treatment. Tactile sensitivity was evaluated using a series of calibrated Semmes-Weinstein von Frey filaments (Stoelting, Ill.), with a bending force ranging from 0.25 to 15 g. Rats were placed in a transparent plastic box endowed with a metal mesh floor and were habituated to this environment before experiment initiation. The von Frey filaments were applied perpendicularly to the mid plantar surface of the hind paws and the mechanical allodynia was determined by sequentially increasing and decreasing the stimulus strength ("up-down" paradigm of filament presentation). The 50% paw withdrawal threshold was determined by the non-parametric Dixon test (Chaplan, S. R. et al, *J. Neurosci. Methods* 53:55-638). Only paw licking after stimulation was considered to be a pain-like response. For the SNL model, only those rats showing a threshold smaller than 4 g (commonly considered in the literature as the tactile allodynia threshold) on the ispilateral side to the lesion were included in the behavioral studies. For the STZ model, the tactile allodynia threshold was evaluated on both hind paws and the average of the 2 values was taken. Only rats showing a value lower than 6 g were included in pharmacological studies. For compound evaluation, the behavioural tests were performed on day 14, post SNL- or STZ-induced neuropathy.

Using this method, illustrative Polycyclic Guanine Derivatives of the present invention were tested and shown to inhibit diabetic neuropathy in the test animals. Accordingly, the Polycyclic Guanine Derivatives are useful for treating diabetic neuropathy.

Example 73

Measurement of Cold Allodynia in CCI Rats

Thermal allodynia to a cold stimulus was assessed as described (Hunter, J. C. et al., *Eur. J. Pharmacol.* 324:153-160) with modifications. The apparatus (2 Biological Instruments, Italy) consisted of a perspex with a steel plate maintained at 10° C. For the measurement of cold allodynia, each rat was placed upon the metal floor. The nociceptive endpoint was the withdrawal or the flinching of the right hindpaw. A cut-off was imposed at 25 seconds in order to avoid any possible interference with the sensitivity of the animal to respond to subsequent post treatment exposure to a cold stimulus. For each experiment, animals were first pre-screened twice with 20-minute intervals between tests to select for animals displaying clear signs of allodynia. Only rats with paw withdrawal latency on the ligated side $\leq 8$ seconds in both trials were included in the pharmacological studies.

Using this method, illustrative Polycyclic Guanine Derivatives of the present invention were tested and shown to inhibit cold allodynia in the test animals. Accordingly, the Polycyclic Guanine Derivatives are useful for treating pain.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

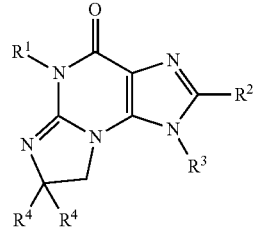

(I)

or a pharmaceutically acceptable salt, thereof, wherein:
$R^1$ is —$C_1$-$C_6$ alkyl or -alkylene-O—$C_1$-$C_6$ alkyl;
$R^2$ is alkyl, aryl, -alkylene-aryl, heterocycloalkyl or heteroaryl, any of which may be optionally substituted with $R^5$;
$R^3$ is alkyl, -alkylene-aryl, cycloalkyl, -alkylene-cycloalkyl or -alkylene-heterocycloalkyl, wherein an aryl, cycloalkyl or heterocycloalkyl group can be optionally substituted with $R^7$;
each occurrence of $R^4$ is independently H or —$C_1$-$C_6$ alkyl, or both $R^4$ groups together with the carbon atom to which they are attached, join to form a 3- to 7-membered cycloalkyl group, which can be optionally fused with a benzene ring;
$R^5$ represents from 1 to 3 groups, each independently selected from alkenyl, alkynyl, aryl, heterocycloalkyl, heteroaryl, halo, —CN, —C(O)O$R^6$, —C(O)$R^6$, —C(O)N($R^6$)$_2$, —S(O)$_2$NH$R^6$, —OH, —O-alkyl, haloalkyl, —O-haloalkyl and —NHC(O)N($R^6$)$_2$, where an aryl, heterocycloalkyl or heteroaryl group may be optionally substituted with up to 3 groups, each independently selected from —$C_1$-$C_6$ alkyl, halo, —C(O)O$R^6$ and —C(O)N($R^6$)$_2$;
each occurrence of $R^6$ is independently H, —$C_1$-$C_6$ alkyl, aryl or heterocycloalkyl, wherein an aryl or heterocycloalkyl group can be optionally substituted with up to 3 groups, each independently selected from alkyl, —O-alkyl, halo, —CN, haloalkyl, -alkylene-C(O)N($R^8$)$_2$, —C(O)N($R^8$)$_2$, —C(O)O$R^8$, —C(O)-heterocycloalkyl, —C(O)-alkyl or —N($R^8$)$_2$;
$R^7$ represents from 1 to 3 groups, each independently selected from —$C_1$-$C_6$ alkyl, halo, aryl, —N($R^8$)$_2$, —C(O)O$R^8$, —C(O)N($R^8$)$_2$ and haloalkyl; and
each occurrence of $R^8$ is independently H, —$C_1$-$C_6$ alkyl or aryl, provided that when one of $R^4$ is hydrogen, and the other is ethyl or propyl, and $R^1$ is ethyl, then $R^2$ and $R^3$ both cannot be benzyl.
2. The compound of claim 1, wherein $R^1$ is —$C_1$-$C_6$ alkyl.
3. The compound of claim 2, wherein $R^1$ is methyl or ethyl.

4. The compound of claim 2, wherein $R^2$ is phenyl, which can be optionally substituted with $R^5$.

5. The compound of claim 2, wherein $R^2$ is pyridyl, which can be optionally substituted with $R^5$.

6. The compound of claim 2, wherein $R^2$ is piperidinyl or piperazinyl, each of which can be optionally substituted with $R^5$.

7. The compound of claim 2, wherein $R^3$ is —CH$_2$-phenyl, wherein the phenyl group can be optionally substituted with $R^7$.

8. The compound of claim 2, wherein each $R^4$ is independently selected from H, methyl, isopropyl, sec-butyl or t-butyl.

9. The compound of claim 8, wherein one occurrence of $R^4$ is H and the other is $C_1$-$C_6$ alkyl.

10. The compound of claim 9, wherein one occurrence of $R^4$ is H and the other is isopropyl.

11. The compound of claim 8, wherein each occurrence of $R^4$ is methyl.

12. The compound of claim 2, wherein both $R^4$ groups, together with the carbon atom to which they are attached, join to form a 5- or 6-membered cycloalkyl group.

13. The compound of claim 12, wherein the group formed is a 5-membered cycloalkyl group that is fused to a benzene ring.

14. The compound of claim 4, wherein $R^3$ is —CH$_2$-phenyl, and wherein the phenyl moiety of the $R^3$ group can be optionally substituted with $R^7$.

15. The compound of claim 14, wherein one occurrence of $R^4$ is H and the other is isopropyl.

16. The compound of claim 14, wherein each occurrence of $R^4$ is methyl.

17. The compound of claim 15, wherein $R^2$ is:

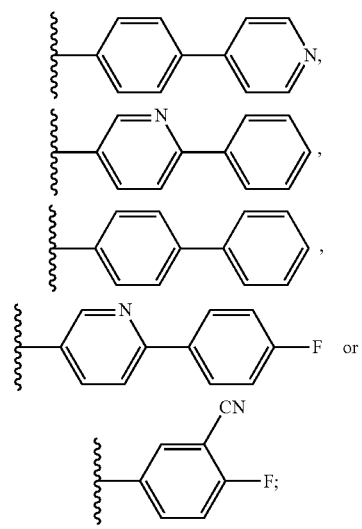

and $R^3$ is:

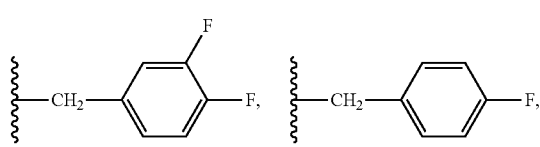

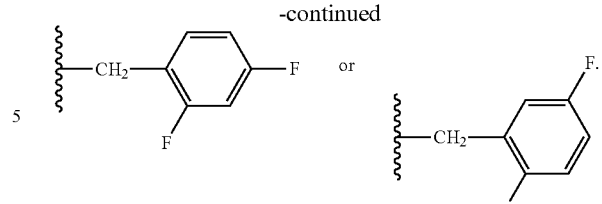

18. The compound of claim 16, wherein $R^2$ is:

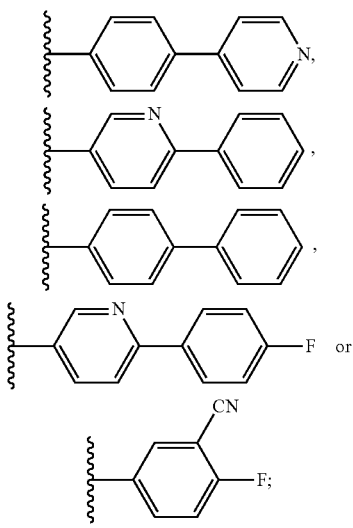

and $R^3$ is:

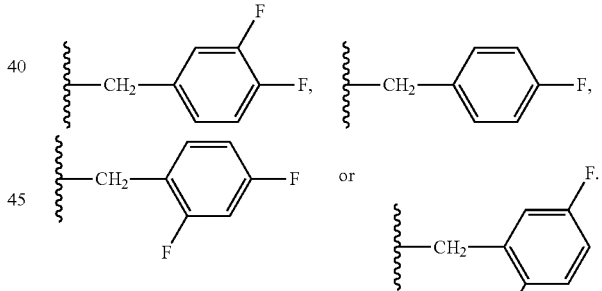

19. The compound of claim 1, having the formula:

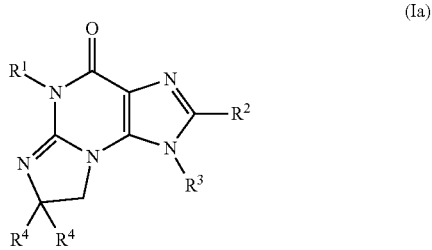

(Ia)

and pharmaceutically acceptable salts, solvates, esters and prodrugs thereof, wherein:

R¹ is —C₁-C₆ alkyl;

R² is -A-B,

A is alkyl, aryl, -alkylene-aryl, heterocycloalkyl or heteroaryl, any of which may be optionally substituted with R⁵;

B is alkyl, aryl, -alkylene-aryl, heterocycloalkyl or heteroaryl, any of which may be optionally substituted with R⁵ such that at least one of A and B is heteroaryl;

R³ is -alkylene-aryl, wherein the aryl moiety can be optionally substituted with R⁷;

each occurrence of R⁴ is independently H or —C₁-C₆ alkyl, or both R⁴ groups together with the carbon atom to which they are attached, join to form a 3- to 7-membered cycloalkyl group, which can be optionally fused with a benzene ring;

R⁵ represents from 1 to 3 groups, each independently selected from aryl, heterocycloalkyl, heteroaryl, halo, —CN, —C(O)OR⁶, —C(O)R⁶, —C(O)N(R⁶)₂, —S(O)₂NHR⁶, —OH, —O-alkyl, haloalkyl, —O-haloalkyl and —NHC(O)N(R⁶)₂, where an aryl, heterocycloalkyl or heteroaryl group may be optionally substituted with up to 3 groups, each independently selected from —C₁-C₆ alkyl, halo, —C(O)OR⁶ and —C(O)N(R⁶)₂;

each occurrence of R⁶ is independently H, —C₁-C₆ alkyl, aryl or heterocycloalkyl;

R⁷ represents from 1 to 3 groups, each independently selected from —C₁-C₆ alkyl, halo, aryl, —N(R⁸)₂, —C(O)OR⁸, —C(O)N(R⁸)₂ and haloalkyl; and each occurrence of R⁸ is independently H, —C₁-C₆ alkyl or aryl.

20. The compound of claim 19, wherein R¹ is methyl or ethyl.

21. The compound of claim 19, wherein A is 6-membered heteroaryl.

22. The compound of claim 19, wherein B is 6-membered heteroaryl.

23. The compound of claim 19, wherein R² is:

24. The compound of claim 19, wherein R³ is benzyl.

25. The compound of claim 19, wherein R³ is:

26. The compound of claim 19, wherein each occurrence of R⁴ is independently, H, methyl or isopropyl.

27. The compound of claim 26, wherein each occurrence of R⁴ is methyl.

28. The compound of claim 26, wherein one occurrence of R⁴ is H and the other is isopropyl.

29. The compound of claim 20, wherein R² is:

30. The compound of claim 29, wherein R³ is:

31. The compound of claim 30, wherein each occurrence of R⁴ is independently, H, methyl or isopropyl.

32. A compound being any of the compounds numbered 1 through 160 as set forth in the above specification, or a pharmaceutically acceptable salt, or ester thereof.

33. A composition comprising one or more compounds of claim 1, or a pharmaceutically acceptable salt, or ester thereof, and a pharmaceutically acceptable carrier.

34. A composition comprising one or more compounds of claim 19 or a pharmaceutically acceptable salt, or ester or thereof, and a pharmaceutically acceptable carrier.

* * * * *